(12) United States Patent
Altman et al.

(10) Patent No.: US 9,598,405 B2
(45) Date of Patent: Mar. 21, 2017

(54) THIAZOLE-SUBSTITUTED AMINOPYRIDINES AS SPLEEN TYROSINE KINASE INHIBITORS

(71) Applicant: Merck Sharp & Dohme Corp., Rahway, NJ (US)

(72) Inventors: Michael D. Altman, Needham, MA (US); Brian M. Andresen, Sharon, MA (US); Kenneth L. Arrington, Lansdale, PA (US); Kaleen Konrad Childers, Medfield, MA (US); Maria Emilia Di Francesco, Houston, TX (US); John Michael Ellis, Needham, MA (US); Andrew M. Haidle, Cambridge, MA (US); Yuan Liu, Belmont, MA (US); Alan B. Northrup, Reading, MA (US); Brendan O'Boyle, Boston, MA (US); Ryan D. Otte, Natick, MA (US); Michael H. Reutershan, Brookline, MA (US); Dilrukshi Vitharana, Somerville, MA (US); Hyun Chong Woo, Natick, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/653,488

(22) PCT Filed: Dec. 19, 2013

(86) PCT No.: PCT/US2013/076341
§ 371 (c)(1),
(2) Date: Jun. 18, 2015

(87) PCT Pub. No.: WO2014/100314
PCT Pub. Date: Jun. 26, 2014

(65) Prior Publication Data
US 2015/0353535 A1    Dec. 10, 2015

Related U.S. Application Data

(60) Provisional application No. 61/740,802, filed on Dec. 21, 2012.

(51) Int. Cl.
*C07D 413/04* (2006.01)
*C07D 417/14* (2006.01)
*A61K 31/444* (2006.01)
*A61K 45/06* (2006.01)

(52) U.S. Cl.
CPC .......... *C07D 417/14* (2013.01); *A61K 31/444* (2013.01); *A61K 45/06* (2013.01)

(58) Field of Classification Search
CPC .................................................. C07D 413/04
USPC ........................................ 546/256; 514/333
See application file for complete search history.

(56) References Cited

U.S. PATENT DOCUMENTS

| 6,248,790 | B1 | 6/2001 | Uckun et al. |
|---|---|---|---|
| 6,432,963 | B1 | 8/2002 | Hisamichi et al. |
| 6,589,950 | B1 | 7/2003 | Collingwood et al. |
| 6,797,706 | B1 | 9/2004 | Hisamichi et al. |
| 6,911,443 | B2 | 6/2005 | Yura et al. |
| 7,060,827 | B2 | 6/2006 | Singh et al. |
| 7,122,542 | B2 | 10/2006 | Singh et al. |
| 7,803,801 | B2 | 9/2010 | Kodama et al. |
| 8,551,984 | B2 | 10/2013 | Altman et al. |
| 8,735,417 | B2 | 5/2014 | Altman et al. |
| 8,759,366 | B2 | 6/2014 | Childers et al. |
| 8,796,310 | B2 | 8/2014 | Romeo et al. |
| 8,987,456 | B2 | 3/2015 | Altman et al. |
| 9,006,444 | B2 | 4/2015 | Altman et al. |
| 9,120,785 | B2 | 9/2015 | Altman et al. |
| 9,145,391 | B2 | 9/2015 | Deschenes et al. |

(Continued)

FOREIGN PATENT DOCUMENTS

| EP | 877020 A1 | 11/1998 |
|---|---|---|
| EP | 1392684 B1 | 9/2006 |

(Continued)

OTHER PUBLICATIONS

Cywin, et al, "Discovery and SAR ov Novel [1,6]Naphthyridines as potent Inhibitors of Spleen Tyrosine Kinase (SYK)" Bioorganic & Medicinal Chemistry Letters, 2003, pp. 1415-1418, vol. 13.

(Continued)

*Primary Examiner* — Patricia L Morris
(74) *Attorney, Agent, or Firm* — Eric A. Meade; Anna L. Cocuzzo

(57) ABSTRACT

The invention provides certain thiazole-substituted aminopyridine compounds of the Formula (I) (I) or pharmaceutically acceptable salts thereof, wherein $R^1$, $R^2$, $R^3$, $R^4$, $R^5$, $R^6$, $C^y$, and the subscript t are as defined herein. The invention also provides pharmaceutical compositions comprising such compounds, and methods of using the compounds for treating diseases or conditions mediated by Spleen Tyrosine Kinase (Syk).

14 Claims, No Drawings

(56) References Cited

U.S. PATENT DOCUMENTS

| | | |
|---|---|---|
| 9,216,173 B2 | 12/2015 | Altman et al. |
| 9,242,984 B2 | 1/2016 | Machacek et al. |
| 9,290,490 B2 | 3/2016 | Altman et al. |
| 2004/0029902 A1 | 2/2004 | Singh et al. |
| 2004/0054179 A1 | 3/2004 | Yura et al. |
| 2006/0135543 A1 | 6/2006 | Singh et al. |
| 2006/0178407 A1 | 8/2006 | Argade et al. |
| 2006/0211657 A1 | 9/2006 | Singh et al. |
| 2006/0234483 A1 | 10/2006 | Arak et al. |
| 2006/0247262 A1 | 11/2006 | Baenteli et al. |
| 2007/0004626 A1 | 1/2007 | Masuda et al. |
| 2007/0129362 A1 | 6/2007 | Bhamidipati et al. |
| 2007/0197782 A1 | 8/2007 | Clough et al. |
| 2010/0311965 A1 | 12/2010 | Sawa et al. |
| 2012/0277192 A1 | 11/2012 | Altman et al. |
| 2013/0225548 A1 | 8/2013 | Fujihara et al. |
| 2015/0148327 A1 | 5/2015 | Haidle et al. |
| 2015/0166486 A1 | 6/2015 | Haidle et al. |
| 2015/0175575 A1 | 6/2015 | Lim et al. |
| 2015/0284381 A1 | 10/2015 | Andresen et al. |
| 2015/0299125 A1 | 10/2015 | Haidle et al. |
| 2015/0329531 A1 | 11/2015 | Machacek |
| 2016/0060255 A1 | 3/2016 | Anthony et al. |
| 2016/0060256 A1 | 3/2016 | Arrington et al. |

FOREIGN PATENT DOCUMENTS

| | | |
|---|---|---|
| EP | 2441755 A1 | 4/2012 |
| JP | 2004203748 | 12/2002 |
| WO | 97/12871 A1 | 4/1997 |
| WO | 02/096905 A1 | 12/2002 |
| WO | 03/057659 A1 | 7/2003 |
| WO | 03/078404 A1 | 9/2003 |
| WO | 2004/087698 A2 | 10/2004 |
| WO | 2005/013996 A2 | 2/2005 |
| WO | 2005/026158 A1 | 3/2005 |
| WO | 2005/033103 A1 | 4/2005 |
| WO | 2006/004865 A1 | 1/2006 |
| WO | 2006/028833 A1 | 3/2006 |
| WO | 2006/050480 A2 | 5/2006 |
| WO | 2006/068770 A1 | 6/2006 |
| WO | 2006/078846 A1 | 7/2006 |
| WO | 2006/129100 A1 | 12/2006 |
| WO | 2006/133426 A2 | 12/2006 |
| WO | 2006/135915 A2 | 12/2006 |
| WO | 2007/009681 A1 | 1/2007 |
| WO | 2007/009773 A1 | 1/2007 |
| WO | 2007/028445 A1 | 3/2007 |
| WO | 2007/042298 A1 | 4/2007 |
| WO | 2007/042299 A1 | 4/2007 |
| WO | 2007/070872 A1 | 6/2007 |
| WO | 2007/085540 A1 | 8/2007 |
| WO | 2007/107469 A1 | 9/2007 |
| WO | 2007/120980 A2 | 10/2007 |
| WO | 2009/031011 A2 | 3/2009 |
| WO | 2009/084695 A1 | 7/2009 |
| WO | 2009/097287 A1 | 8/2009 |
| WO | 2009/102468 A1 | 8/2009 |
| WO | 2009/131637 A2 | 10/2009 |
| WO | 2009/136995 A2 | 11/2009 |
| WO | 2009/145856 A1 | 12/2009 |
| WO | 2010/027500 A1 | 3/2010 |
| WO | 2010/068257 A1 | 6/2010 |
| WO | 2010/068258 A1 | 6/2010 |
| WO | 2011/086085 A1 | 7/2011 |
| WO | 2012/041476 | 4/2012 |
| WO | 2012/057262 A1 | 5/2012 |
| WO | 2012/154518 A1 | 11/2012 |
| WO | 2012/154520 A1 | 11/2012 |
| WO | 2013/192088 A1 | 12/2013 |
| WO | 2014/031438 A2 | 2/2014 |

OTHER PUBLICATIONS

International Search Report of PCT/US13/76341 mailed Apr. 28, 2014.

Written Opinion of PCT/US13/76341 mailed Apr. 28, 2014.

Yamamoto, et al, "The Orally Available Spleen Tyrosine Kinase inhibitor (2-[7-(3,4-Dimethoxyphenyl)-imidazo[1,2-c]pyrimidin-5-ylamino]-nicotinamide Dihydrochloride (BAY 61-3606) Blocks Antigen-Induced Airway Inflammation in Rodents", The Journal of Pharmacology and Experimental Therapeutics, 2003, pp. 1174-1181, vol. 306(3).

THIAZOLE-SUBSTITUTED AMINOPYRIDINES AS SPLEEN TYROSINE KINASE INHIBITORS

CROSS REFERENCE TO RELATED APPLICATIONS

This application is a U.S. National Phase application under 35 U.S.C. §371 of PCT Application No. PCT/US2013/076341, filed Dec. 19, 2013, which claims priority under 35 U.S.C. §119(e) from U.S. Provisional Application No. 61/740,802, filed Dec. 21, 2012.

FIELD OF THE INVENTION

The present invention relates to certain thiazole-substituted aminopyridine compounds of the Formula (I) (also referred to herein as the "compounds of the Formula (I)" or "compounds of Formula (I)") which are inhibitors of Spleen Tyrosine Kinase (Syk) kinase activity, or are prodrugs thereof. The present invention also provides compositions comprising such compounds, and methods of using such compounds for treating conditions or disorders associated with inappropriate Syk activity, in particular in the treatment and prevention of disease states mediated by Syk. Such disease states may include inflammatory, allergic and auto-immune diseases, for example, asthma, chronic obstructive pulmonary disease (COPD), adult respiratory distress syndrome (ARDS), ulcerative colitis, Crohns disease, bronchitis, dermatitis, allergic rhinitis, psoriasis, scleroderma, urticaria, rheumatoid arthritis, idiopathic thrombocytopenic purpura (ITP), multiple sclerosis, cancer, HIV and lupus.

BACKGROUND OF THE INVENTION

Spleen Tyrosine Kinase (Syk) is a protein tyrosine kinase which has been described as a key mediator of immunoreceptor signalling in a host of inflammatory cells including mast cells, B-cells, macrophages and neutrophils. These immunoreceptors, including Fc receptors and the B-cell receptor, are important for both allergic diseases and antibody-mediated autoimmune diseases and thus pharmacologically interfering with Syk could conceivably treat these disorders.

Allergic rhinitis and asthma are diseases associated with hypersensitivity reactions and inflammatory events involving a multitude of cell types including mast cells, eosinophils, T cells and dendritic cells. Following exposure to allergen, high affinity immunoglobulin receptors for IgE and IgG become cross-linked and activate downstream processes in mast cells and other cell types leading to the release of pro-inflammatory mediators and airway spasmogens. In the mast cell, for example, IgE receptor cross-linking by allergen leads to release of mediators including histamine from pre-formed granules, as well as the synthesis and release of newly synthesized lipid mediators including prostaglandins and leukotrienes.

Syk kinase is a non-receptor linked tyrosine kinase which is important in transducing the downstream cellular signals associated with cross-linking $Fc_{epsilon}RI$ and or $Fc_{epsilon}RI$ receptors, and is positioned early in the signalling cascade. In mast cells, for example, the early sequence of $Fc_{epsilon}RI$ signalling following allergen cross-linking of receptor-IgE complexes involves first Lyn (a Src family tyrosine kinase) and then Syk. Inhibitors of Syk activity would therefore be expected to inhibit all downstream signalling cascades thereby alleviating the immediate allergic response and adverse events initiated by the release of pro-inflammatory mediators and spasmogens (Wong et al. 2004, *Expert Opin. Investig. Drugs* (2004) 13 (7) 743-762).

Recently, it has been shown that the Syk kinase inhibitor R112 (Rigel), dosed intranasally in a phase I/II study for the treatment of allergic rhinitis, gave a statistically significant decrease in $PGD_2$, a key immune mediator that is highly correlated with improvements in allergic rhinorrhea, as well as being safe across a range of indicators, thus providing the first evidence for the clinical safety and efficacy of a topical Syk kinase inhibitor. (Meltzer, Eli O.; Berkowitz, Robert B.; Grossbard, Elliott B, *Journal of Allergy and Clinical Immunology* (2005), 115(4), 791-796). In a more recent phase II clinical trial for allergic rhinitis (Clinical Trials.gov Identifier NCT0015089), R112 was shown as having a lack of efficacy versus placebo.

Rheumatoid Arthritis (RA) is an auto-immune disease affecting approximately 1% of the population. It is characterised by inflammation of articular joints leading to debilitating destruction of bone and cartilage. Recent clinical studies with Rituximab, which causes a reversible B cell depletion, (J. C. W. Edwards et al. 2004, *New Eng. J. Med.* 350: 2572-2581) have shown that targeting B cell function is an appropriate therapeutic strategy in auto-immune diseases such as RA. Clinical benefit correlates with a reduction in auto-reactive antibodies (or Rheumatoid Factor) and these studies suggest that B cell function and indeed auto-antibody production are central to the ongoing pathology in the disease.

Studies using cells from mice deficient in the Spleen Tyrosine Kinase (Syk) have demonstrated a non-redundant role of this kinase in B cell function. The deficiency in Syk is characterised by a block in B cell development (M. Turner et al. 1995 Nature 379: 298-302 and Cheng et al. 1995, *Nature* 378: 303-306). These studies, along with studies on mature B cells deficient in Syk (Kurasaki et al. 2000, *Immunol. Rev.* 176:19-29), demonstrate that Syk is required for the differentiation and activation of B cells. Hence, inhibition of Syk in RA patients is likely to block B cell function, and thereby reduce Rheumatoid Factor production. In addition to the role of Syk in B cell function, and of further relevance to the treatment of RA, is the requirement for Syk activity in Fc receptor (FcR) signalling. FcR activation by immune complexes in RA has been suggested to contribute to the release of multiple pro-inflammatory mediators.

SUMMARY OF THE INVENTION

The present invention provides novel compounds that are potent inhibitors of Syk, or are prodrugs thereof, as well as pharmaceutical compositions containing them. As Syk inhibitors compounds of Formula (I) are useful in the treatment and prevention of diseases and disorders mediated by the Syk protein; such diseases and disorders include, but are not limited to, asthma, COPD, rheumatoid arthritis, cancer and idiopathic thrombocytopenic purpura.

DETAILED DESCRIPTION OF THE INVENTION

Definitions

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name, and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "fluoroalkyl," "—O-alkyl," etc.

As used herein, and throughout this disclosure, the following terms, unless otherwise indicated, shall be understood to have the following meanings:

A "patient" is a human or non-human mammal. In one embodiment, a patient is a human. In another embodiment, a patient is a chimpanzee.

The term "therapeutically effective amount" as used herein, refers to an amount of the compound of Formula (I) and/or an additional therapeutic agent, or a composition thereof that is effective in producing the desired therapeutic, ameliorative, inhibitory or preventative effect when administered to a patient suffering from a disease or condition mediated by Syk. In the combination therapies of the present invention, a therapeutically effective amount can refer to each individual agent or to the combination as a whole, wherein the amounts of all agents administered are together effective, but wherein the component agent of the combination may not be present individually in an effective amount.

The term "preventing," as used herein with respect to cancer or an inflammatory disease or disorder, refers to reducing the likelihood of cancer pain or an inflammatory disease or disorder.

The term "alkyl," as used herein, refers to an aliphatic hydrocarbon group having one of its hydrogen atoms replaced with a bond having the specified number of carbon atoms. In different embodiments, an alkyl group contains from 1 to 6 carbon atoms ($C_1$-$C_6$ alkyl) or from 1 to 3 carbon atoms ($C_1$-$C_3$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched.

The term "fluoroalkyl," as used herein, refers to an alkyl group as defined above, wherein one or more of the alkyl group's hydrogen atoms has been replaced with a fluorine. In one embodiment, a fluoroalkyl group has from 1 to 6 carbon atoms. In another embodiment, a fluoroalkyl group has from 1 to 3 carbon atoms. In another embodiment, a fluoroalkyl group is substituted with from 1 to 3 F atoms. Non-limiting examples of fluoroalkyl groups include —$CH_2F$, —$CHF_2$, and —$CF_3$. The term "$C_1$-$C_3$ fluoroalkyl" refers to a fluoroalkyl group having from 1 to 3 carbon atoms.

The term "alkoxy" as used herein, refers to an —O-alkyl group, wherein an alkyl group is as defined above. Non-limiting examples of alkoxy groups include methoxy, ethoxy, n-propoxy, isopropoxy, n-butoxy and t-butoxy. An alkoxy group is bonded via its oxygen atom to the rest of the molecule.

The term "aryl," as used herein, refers to an aromatic monocyclic or multicyclic ring system comprising from about 6 to about 14 carbon atoms. In one embodiment, an aryl group contains from about 6 to 10 carbon atoms ($C_6$-$C_{10}$ aryl). In another embodiment an aryl group is phenyl. Non-limiting examples of aryl groups include phenyl and naphthyl.

The term "carbocycle," as used herein, refers to a fully saturated or partially unsaturated, monocyclic or multicyclic ring system comprising from about 3 to 12 carbon atoms. In one embodiment, the carbocyclic group contains from 4 to 12 carbon atoms. Non-limiting examples of carbocyclic groups include cycloalkyl groups, as defined herein. In specific embodiments, the carbocyclic groups are selected from cyclopropyl, cyclobutyl, cyclopentyl, cyclohexyl, bicyclo[3.2.1]octyl, and spiro[3.5]nonyl.

The term "cycloalkyl," as used herein, refers to a saturated ring containing the specified number of ring carbon atoms, and no heteroatom. In a like manner the term "$C_3$-$C_6$ cycloalkyl" refers to a saturated ring having from 3 to 6 ring carbon atoms. Non-limiting examples of monocyclic cycloalkyls include cyclopropyl, cyclobutyl, cyclopentyl, and cyclohexyl.

The term "halo," as used herein, means —F, —Cl, —Br or —I. In one embodiment, a halo group is —F or —Cl. In another embodiment, a halo group is —F.

The term "heteroaryl," as used herein, refers to an aromatic monocyclic or multicyclic ring system comprising about 5 to about 14 ring atoms, wherein from 1 to 3 of the ring atoms is independently N, O, or S and the remaining ring atoms are carbon atoms. In one embodiment, a heteroaryl group has 5 to 10 ring atoms. In another embodiment, a heteroaryl group is monocyclic ring system and has 5 or 6 ring atoms. In another embodiment, a heteroaryl group is a bicyclic ring system. A heteroaryl group is joined via a ring carbon atom. The term "heteroaryl" also includes a heteroaryl as defined above fused to a heterocycle as defined below. The term "heteroaryl" also encompasses a heteroaryl group, as defined above, which is fused to a benzene, a cyclohexadiene or a cyclohexene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furyl, pyrrolyl, triazolyl, 1,2,4-thiadiazolyl, pyrazinyl, pyridazinyl, indolyl, quinoxalinyl, phthalazinyl, oxindolyl, imidazo[1,2-a]pyridinyl, imidazo [2,1-b]thiazolyl, and the like. In one embodiment, a heteroaryl group is a 5-membered heteroaryl. In another embodiment, a heteroaryl group is a 6-membered heteroaryl.

The term "heterocyclyl" or "heterocycle"," as used herein, refers to a non-aromatic saturated or partially saturated monocyclic or multicyclic ring system containing 3 to 11 ring atoms, wherein from 1 to 4 of the ring atoms are independently O, S, or N, and the remainder of the ring atoms are carbon atoms. In one embodiment, a heterocyclyl group is monocyclic and has from 3 to 7 ring atoms. In another embodiment, a heterocyclyl group is monocyclic and has from about 4 to 7 ring atoms. In another embodiment, a heterocyclyl group is bicyclic and has from 7 to 11 ring atoms. In still another embodiment, a heterocyclyl group is monocyclic and has 5 or 6 ring atoms. In one embodiment, a heterocyclyl group is monocyclic. In another embodiment, a heterocyclyl group is bicyclic. A heterocyclyl group can be joined to the rest of the molecule via a ring carbon or ring nitrogen atom. The nitrogen or sulfur atom of the heterocyclyl can be optionally oxidized to the corresponding N-oxide, S-oxide or S,S-dioxide. Non-limiting examples of monocyclic heterocyclic rings include oxetanyl, piperidyl, pyrrolidinyl, piperazinyl, morpholinyl, thiomorpholinyl, thiazolidinyl, dihydropyranyl, pyran, 1,4-dioxanyl, tetrahydrofuranyl, tetrahydrothiophenyl, delta-lactam, delta-lactone, and the like.

The term "substituted" means that one or more hydrogens on the atoms of the designated are replaced with a selection from the indicated group, provided that the atoms' normal valencies under the existing circumstances are not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

When any substituent or variable occurs more than one time in any constituent or the compound of Formula (I), its definition on each occurrence is independent of its definition at every other occurrence, unless otherwise indicated.

The term "in purified form," as used herein, refers to the physical state of a compound after the compound is isolated from a synthetic process (e.g., from a reaction mixture), a natural source, or a combination thereof. The term "in purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

The compounds of Formula (I) may contain one or more stereogenic centers and can thus occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention.

All stereoisomers (for example, geometric isomers, optical isomers and the like) of the present compounds (including those of the salts and solvates of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

The compounds of Formula (I) can form salts which are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Such acidic and basic salts used within the scope of the invention are pharmaceutically acceptable (i.e., non-toxic, physiologically acceptable) salts. Salts of the compounds of Formula (I) may be formed, for example, by reacting a compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Prop-* erties, Selection and Use. (2002) Zurich: Wiley-VCH; S. Berge et al, *Journal of Pharmaceutical Sciences* (1977) 66f) 1-19; P. Gould, *International J of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

The present invention further includes the compounds of Formula (I) in all their isolated forms. For example, the above-identified compounds are intended to encompass all forms of the compounds such as, any solvates, hydrates, stereoisomers, and tautomers thereof.

As used herein, the term "composition" is intended to encompass a product comprising the specified ingredients in the specified amounts, as well as any product which results, directly or indirectly, from combination of the specified ingredients in the specified amounts.

In the compounds of generic Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula (I). For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula (I) can be prepared without undue experimentation by conventional techniques well known to those skilled in the art or by processes analogous to those described in the examples herein using appropriate isotopically-enriched reagents and/or intermediates.

Compounds of the Invention

The present invention provides a compound of Formula (I) or a pharmaceutically acceptable salt thereof, wherein $R^1$, $R^2$, $R^3$, $R^4$, $R^5$, $R^6$, $C^y$, and the subscript t are as set forth below. Described below are embodiments of the compound of Formula (I). The compound of the Formulas (IA) (shown below) is an embodiment of the compound of Formula (I).

In embodiment no. 1, the invention provides a compound of Formula (I),

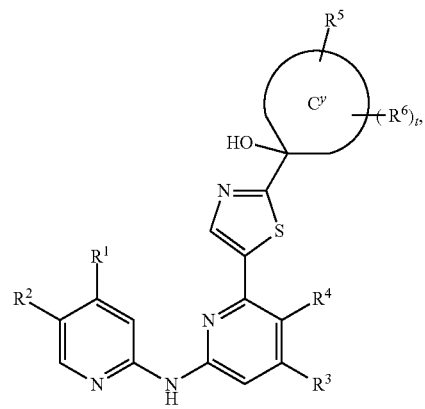

(I)

or a pharmaceutically acceptable salt thereof, wherein $R^1$ is selected from the group consisting of:
(a) $C_1$-$C_6$ alkyl;
(b) $C_1$-$C_3$ alkoxy;
(c) $C_1$-$C_3$ fluoroalkyl;
(d) —(CH$_2$)$_r$CO$_2$R$^b$,
(e) —O(CH$_2$)$_s$N(R$^c$)$_2$,
(f) hydroxyl;
(g) halo;
(h) H;
(i) —C(O)—$C_1$-$C_6$ alkyl;
(j) $C_3$-$C_6$ cycloalkyl;
(k) a 5-membered heteroaryl containing 1-3 heteroatoms selected from group consisting of N, O, and S, and wherein said heteroaryl is unsubstituted or substituted by 1 to 2 moieties selected from the group consisting of $C_1$-$C_3$ alkyl or —CH$_2$-phenyl, wherein said phenyl is unsubstituted or methoxy; and
(l) a group of the formula

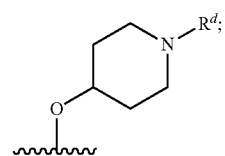

$R^2$ is selected from the group consisting of H and halo;
$R^3$ is selected from the group consisting of
(a) H;
(b) $C_1$-$C_3$ alkyl;
(c) —N(R$^c$)$_2$;
(d) —N(H)C(O)—$C_1$-$C_4$ alkyl;
(e) —CH$_2$—O—$C_1$-$C_3$ alkyl;
$R^4$ is selected from the group consisting of H or halo;
$R^5$ is selected from the group consisting of
(a) —C(O)OR$^A$; and
(b) —C(O)N(R$^c$)$_2$;
each $R^6$ is a moiety independently selected from the group consisting of fluoro and $C_1$-$C_3$ alkyl;
ring $C^y$ is a saturated, mono- or bicyclic carbocyclic ring system containing 4 to 12 carbon atoms;
$R^b$ is H or $C_1$-$C_3$ alkyl;
each $R^c$ is independently H, $C_1$-$C_3$ alkyl, or —C(O)—O—$C_1$-$C_6$ alkyl;
$R^d$ is H or —C(O)—O—$C_1$-$C_6$ alkyl;
the subscript r is 0, 1, or 2;

the subscript s is 1, 2, 3, or 4;

the subscript t is 0, 1, 2, 3, 4, or 5;

$R^A$ is independently selected from the group consisting of:

(a) H;

(b) $C_1$-$C_5$ alkyl;

(c) a group of the formula -M-$R^{CH}$, wherein

M is a bond or —$(CH_2)_{n1}$—, wherein the subscript n1 is 1 or 2;

$R^{CH}$ is (a) aryl or $C_3$-$C_6$ cycloalkyl optionally substituted with 1-3 groups independently selected from halo, $C_1$-$C_4$ alkyl, or $C_1$-$C_4$ alkoxy; or (b) a 5- to 6-membered monocyclic heterocycle containing 1 or 2 heteroatoms independently selected from the group consisting of N and O, wherein said heterocycle of $R^{CH}$ is optionally substituted with 1 or 2 groups independently selected from the group consisting of oxo and $C_1$-3 alkyl;

(d) a group of the formula —$(CH_2)_{n1}$—$R^m$ or —$(CH_2)_2$—O—$(CH_2)_2$—$R^m$ wherein $R^m$ is —$CO_2R^{m1}$, —$C(O)N(R^{m2})_2$, or —$O(CO)R^{m1}$;

$R^{m1}$ is $C_1$-$C_4$ alkyl; and $R^{m2}$2 is H or $C_1$-$C_4$ alkyl;

(e) a group of the formula —$(CH_2)_2$—$R^n$, $R^n$ is —OH, —O—($C_1$-$C_4$ alkyl), —O—$(CH_2)_2$—O—($C_1$-$C_4$ alkyl), —$NH_2$, —$N(H)(C_1$-$C_4$ alkyl) or —$N(C_1$-$C_4$ alkyl)$_2$;

(f) a group of the formula

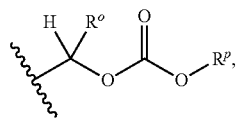

wherein $R^o$ is H or $C_1$-$C_4$ alkyl; and $R^p$ is $C_1$-$C_4$ alkyl, $C_3$-$C_6$ cycloalkyl, or phenyl; and, (g) a group of the formula

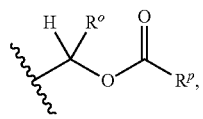

wherein $R^o$ and $R^p$ are as set forth above.

In embodiment no. 2, the invention provides a compound of the Formula (I), wherein $R^1$ is selected from the group consisting of —$CF_3$, —$CH_3$, —$C(CH_3)_3$, —$OCH_3$, —OC(H)(CH_3)_2$, —$OCH_2CH_2CH_2NH_2$, —$OCH_2CH_2CH_2N(H)C(O)OC(CH_3)_3$, H, —$CO_2H$, —$CO_2CH_3$, —$CH_2CO_2H$, —$CH_2CO_2CH_3$, —OH, F, Cl, —O—$C(O)C(CH_3)_3$,

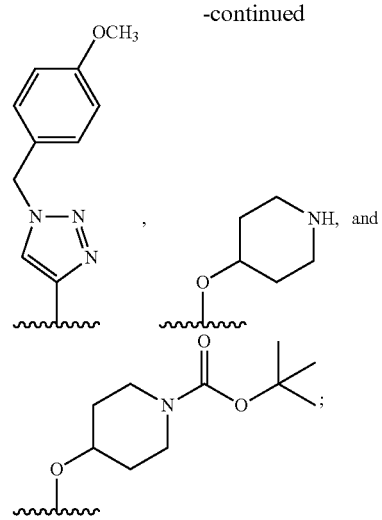

and the remaining variables are as described in embodiment no. 1.

In embodiment no. 3, the invention provides a compound of the Formula (I), wherein $R^2$ is H, F, or Cl; and the remaining variables are as described in embodiment no. 1 or 2.

In embodiment no. 4, the invention provides a compound of the Formula (I), wherein $R^3$ is H, —$CH_3$, —$CH_2OCH_3$, —$NH_2$, or —N(H)—C(O)CH_3$ and the remaining variables are as described in any one of embodiment nos. 1-3.

In embodiment no. 5, the invention provides a compound of the Formula (I), wherein $R^4$ is H, and the remaining variables are as described in any one of embodiment nos. 1-4.

In embodiment no. 6, the invention provides a compound of the Formula (I), wherein the moiety

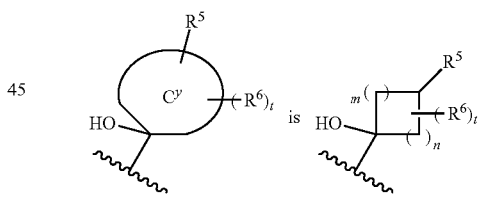

and the subscripts m and n are independently 0, 1, 2, or 3, with the proviso that m and n are not both 0, and the remaining variables are as described in any one of embodiment nos. 1-5.

In embodiment no. 7, the invention provides a compound of the Formula (I), wherein the moiety

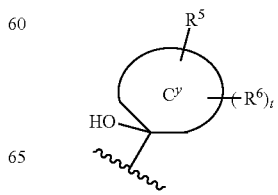

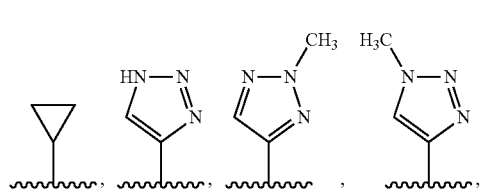

selected from the group consisting of

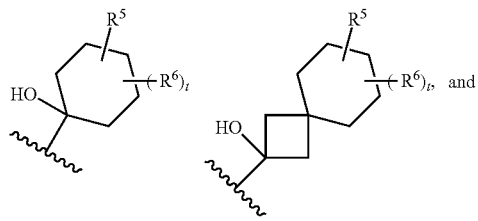

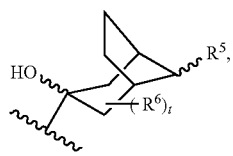

and, and the remaining variables are as described in any one of embodiment nos. 1-5.

In embodiment no. 8, the invention provides a compound of the Formula (I), wherein the moiety

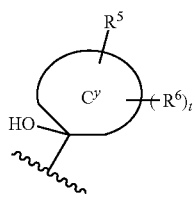

is selected from a group consisting of:

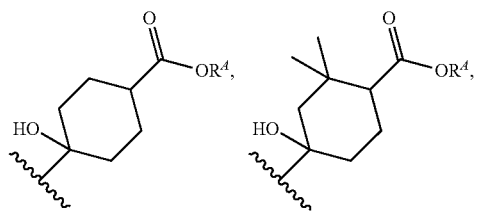

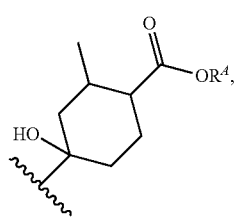

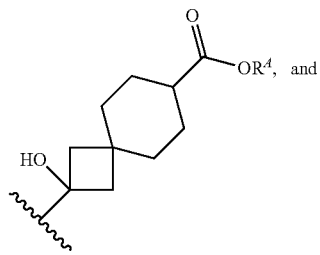

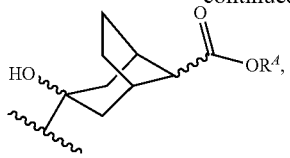

and, and the remaining variables are as described in any one of embodiment nos. 1-5.

In embodiment no. 9, the invention provides a compound of the Formula (I), wherein $R^4$ is H or $C_1$-$C_3$ alkyl, and the remaining variables are as set forth in any one of embodiment nos. 1-8.

In embodiment no. 10, the compound of the Formula (I) has the Formula (IA), wherein $R^4$ is H, and the remaining variables are as set forth in any one of embodiment nos. 1-8.

In embodiment no. 11, the compound of the Formula (I) has the Formula (IA),

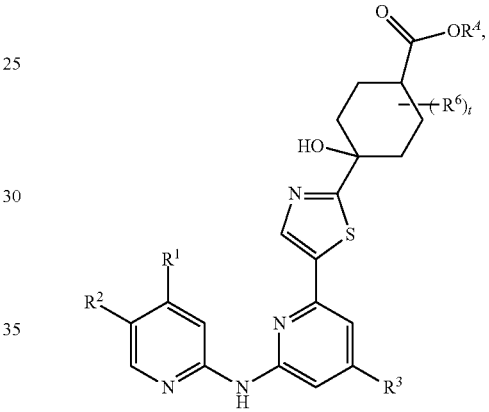

wherein $R^1$ is —CH$_3$, —CF$_3$, or

$R^2$ is H or F;
$R^3$ is H or —CH$_3$;
$R^4$ is H or $C_1$-$C_3$ alkyl;
$R^6$ is —CH$_3$; and
the subscript t is 0, 1, or 2.

In embodiment no. 12, the compound of the Formula (I) has the Formula (IA), wherein $R^4$ is H, and the remaining variables are as set forth in embodiment no. 11.

In embodiment no. 13, the compound is selected from any one of the compounds described in Examples 1-6, or a pharmaceutically acceptable salt thereof.

In embodiment no. 14, the compound is selected from any one of the following compounds or a pharmaceutically acceptable salt thereof:
4-(5-(6-((4-cyclopropylpyridin-2-yl)amino)-4-methylpyridin-2-yl)thiazol-2-yl)-4-hydroxy-2,2-dimethylcyclohexanecarboxylic acid;
methyl 4-(5-{6-[(4-cyclopropylpyridin-2-yl)amino]-4-methylpyridin-2-yl}-1,3-thiazol-2-yl)-4-hydroxy-2,2-dimethylcyclohexanecarboxylate;

4-hydroxy-2,2-dimethyl-4-[5-(4-methyl-6-{[4-(trifluoromethyl)pyridin-2-yl]amino}pyridin-2-yl)-1,3-thiazol-2-yl]cyclohexanecarboxylic acid;

4-[5-(4-amino-6-{[4-(trifluoromethyl)pyridin-2-yl]amino}pyridin-2-yl)-1,3-thiazol-2-yl]-4-hydroxy-2,2-dimethylcyclohexanecarboxylic acid;

methyl 4-{5-[4-(acetylamino)-6-{[4-(trifluoromethyl)pyridin-2-yl]amino}pyridin-2-yl]-1,3-thiazol-2-yl}-4-hydroxy-2,2-dimethylcyclohexanecarboxylate;

methyl 4-[5-(4-amino-6-{[4-(trifluoromethyl)pyridin-2-yl]amino}pyridin-2-yl)-1,3-thiazol-2-yl]-4-hydroxy-2,2-dimethylcyclohexanecarboxylate;

cis-4-(5-(6-((4-(1H-1,2,3-triazol-4-yl)pyridin-2-yl)amino)-4-methylpyridin-2-yl)thiazol-2-yl)-4-hydroxycyclohexanecarboxylic acid;

cis-4-hydroxy-4-{5-[6-({4-[1-(4-methoxybenzyl)-1H-1,2,3-triazol-4-yl]pyridin-2-yl}amino)-4-methylpyridin-2-yl]-1,3-thiazol-2-yl}cyclohexanecarboxylic acid;

cis-4-(5-{6-[(4-{3-[(tert-butoxycarbonyl)amino]propoxy}pyridin-2-yl)amino]-4-methylpyridin-2-yl}-1,3-thiazol-2-yl)-4-hydroxycyclohexanecarboxylic acid;

cis-4-hydroxy-4-[5-(4-methyl-6-{[4-(1-methyl-1H-1,2,3-triazol-4-yl)pyridin-2-yl]amino}pyridin-2-yl)-1,3-thiazol-2-yl]cyclohexanecarboxylic acid;

ethyl cis-4-hydroxy-4-[5-(4-methyl-6-{[4-(1-methyl-1H-1,2,3-triazol-4-yl)pyridin-2-yl]amino}pyridin-2-yl)-1,3-thiazol-2-yl]cyclohexanecarboxylate;

ethyl cis-4-hydroxy-4-[5-(4-methyl-6-{[4-(2-methyl-2H-1,2,3-triazol-4-yl)pyridin-2-yl]amino}pyridin-2-yl)-1,3-thiazol-2-yl]cyclohexanecarboxylate;

cis-4-[5-(6-{[4-(carboxymethyl)pyridin-2-yl]amino}-4-methylpyridin-2-yl)-1,3-thiazol-2-yl]-4-hydroxycyclohexanecarboxylic acid;

2-({6-[2-(cis-4-carboxy-1-hydroxycyclohexyl)-1,3-thiazol-5-yl]-4-methylpyridin-2-yl}amino)pyridine-4-carboxylic acid;

ethyl cis-4-hydroxy-4-[5-(6-{[4-(2-methoxy-2-oxoethyl)pyridin-2-yl]amino}-4-methylpyridin-2-yl)-1,3-thiazol-2-yl]cyclohexanecarboxylate;

methyl 2-[(6-{2-[cis-4-(ethoxycarbonyl)-1-hydroxycyclohexyl]-1,3-thiazol-5-yl}-4-methylpyridin-2-yl)amino]pyridine-4-carboxylate;

cis-4-[5-(6-{[4-(3-aminopropoxyl)pyridin-2-yl]amino}-4-methylpyridin-2-yl)-1,3-thiazol-2-yl]-4-hydroxycyclohexanecarboxylic acid;

cis-4-hydroxy-4-[5-(4-methyl-6-{[[4-(piperidin-4-yloxy)pyridin-2-yl]amino}pyridin-2-yl)-1,3-thiazol-2-yl]cyclohexanecarboxylic acid;

ethyl cis-4-hydroxy-4-[5-(4-methyl-6-{[4-(1H-1,2,3-triazol-4-yl)pyridin-2-yl]amino}pyridin-2-yl)-1,3-thiazol-2-yl]cyclohexanecarboxylate;

ethyl cis-4-hydroxy-4-{5-[6-({4-[1-(4-methoxybenzyl)-1H-1,2,3-triazol-4-yl]pyridin-2-yl}amino)-4-methylpyridin-2-yl]-1,3-thiazol-2-yl}cyclohexanecarboxylate;

4-hydroxy-2,2-dimethyl-4-[5-(4-methyl-6-{[4-(trifluoromethyl)pyridin-2-yl]amino}pyridin-2-yl)-1,3-thiazol-2-yl]cyclohexanecarboxylic acid;

4-(5-{6-[(4-tert-butylpyridin-2-yl)amino]pyridin-2-yl}-1,3-thiazol-2-yl)-4-hydroxy-2,2-dimethylcyclohexanecarboxylic acid;

4-hydroxy-2,2-dimethyl-4-[5-(6-{[4-(trifluoromethyl)pyridin-2-yl]amino}pyridin-2-yl)-1,3-thiazol-2-yl]cyclohexanecarboxylic acid;

4-(5-{6-[(5-fluoro-4-methylpyridin-2-yl)amino]pyridin-2-yl}-1,3-thiazol-2-yl)-4-hydroxy-2,2-dimethylcyclohexanecarboxylic acid;

4-(5-{6-[(4-chloropyridin-2-yl)amino]pyridin-2-yl}-1,3-thiazol-2-yl)-4-hydroxy-2,2-dimethylcyclohexanecarboxylic acid;

4-(5-{6-[(5-fluoropyridin-2-yl)amino]pyridin-2-yl}-1,3-thiazol-2-yl)-4-hydroxy-2,2-dimethylcyclohexanecarboxylic acid;

4-(5-{6-[(5-chloro-4-methylpyridin-2-yl)amino]pyridin-2-yl}-1,3-thiazol-2-yl)-4-hydroxy-2,2-dimethylcyclohexanecarboxylic acid;

4-hydroxy-2,2-dimethyl-4-(5-{6-[(4-methylpyridin-2-yl)amino]pyridin-2-yl}-1,3-thiazol-2-yl)cyclohexanecarboxylic acid;

4-(5-{6-[(5-chloro-4-methylpyridin-2-yl)amino]-4-methylpyridin-2-yl}-1,3-thiazol-2-yl)-4-hydroxy-2,2-dimethylcyclohexanecarboxylic acid;

4-hydroxy-4-(5-{6-[(4-methoxypyridin-2-yl)amino]-4-methylpyridin-2-yl}-1,3-thiazol-2-yl)-2,2-dimethylcyclohexanecarboxylic acid;

4-(5-{6-[(5-fluoro-4-methylpyridin-2-yl)amino]-4-methylpyridin-2-yl}-1,3-thiazol-2-yl)-4-hydroxy-2,2-dimethylcyclohexanecarboxylic acid;

4-(5-{6-[(4-tert-butylpyridin-2-yl)amino]-4-methylpyridin-2-yl}-1,3-thiazol-2-yl)-4-hydroxy-2,2-dimethylcyclohexanecarboxylic acid;

4-hydroxy-2,2-dimethyl-4-(5-{4-methyl-6-[(4-methylpyridin-2-yl)amino]pyridin-2-yl}-1,3-thiazol-2-yl)cyclohexanecarboxylic acid;

cis-2-hydroxy-2-(5-(4-methyl-6-((4-(trifluoromethyl)pyridin-2-yl)amino)pyridin-2-yl)thiazol-2-yl)spiro[3.5]nonane-carboxylic acid;

trans-2-hydroxy-2-[5-(4-methyl-6-{[4-(trifluoromethyl)pyridin-2-yl]amino}pyridin-2-yl)-1,3-thiazol-2-yl]spiro[3.5]nonane-7-carboxylic acid;

trans-3-hydroxy-3-[5-(4-methyl-6-{[4-(trifluoromethyl)pyridin-2-yl]amino}pyridin-2-yl)-1,3-thiazol-2-yl]bicyclo[3.2.1]octane-8-carboxylic acid;

cis-3-hydroxy-3-[5-(4-methyl-6-{[4-(trifluoromethyl)pyridin-2-yl]amino}pyridin-2-yl)-1,3-thiazol-2-yl]bicyclo[3.2.1]octane-8-carboxylic acid;

cis-4-hydroxy-4-[5-(4-methyl-6-{[4-(1-methylethoxyl)pyridin-2-yl]amino}pyridin-2-yl)-1,3-thiazol-2-yl]cyclohexanecarboxylic acid;

cis-4-hydroxy-4-[5-(4-methyl-6-{[4-(trifluoromethyl)pyridin-2-yl]amino}pyridin-2-yl)-1,3-thiazol-2-yl]cyclohexanecarboxylic acid;

4-hydroxy-4-{5-[4-(methoxymethyl)-6-{[4-(trifluoromethyl)pyridin-2-yl]amino}pyridin-2-yl]-1,3-thiazol-2-yl}-2,2-dimethylcyclohexanecarboxylic acid;

methyl 4-hydroxy-4-{5-[4-(methoxymethyl)-6-{[4-(trifluoromethyl)pyridin-2-yl]amino}pyridin-2-yl]-1,3-thiazol-2-yl}-2,2-dimethylcyclohexanecarboxylate;

4-(5-(6-((5-fluoro-4-methylpyridin-2-yl)amino)-4-methylpyridin-2-yl)thiazol-2-yl)-4-hydroxy-2-methylcyclohexanecarboxylic acid; and 4-hydroxy-4-(5-(6-((4-hydroxypyridin-2-yl)amino)-4-methylpyridin-2-yl)thiazol-2-yl)-2-methylcyclohexanecarboxylic acid.

In embodiment no. 15, the compound is selected from any one of the following compounds or a pharmaceutically acceptable salt thereof:

(1S,4R)-4-(5-(6-((4-cyclopropylpyridin-2-yl)amino)-4-methylpyridin-2-yl)thiazol-2-yl)-4-hydroxy-2,2-dimethylcyclohexanecarboxylic acid;

(1R,4S)-4-(5-{6-[(4-cyclopropylpyridin-2-yl)amino]-4-methylpyridin-2-yl}-1,3-thiazol-2-yl)-4-hydroxy-2,2-dimethylcyclohexanecarboxylic acid;

methyl (1R,4S)-4-(5-{6-[(4-cyclopropylpyridin-2-yl)amino]-4-methylpyridin-2-yl}-1,3-thiazol-2-yl)-4-hydroxy-2,2-dimethylcyclohexanecarboxylate;

methyl (1S,4R)-4-(5-{6-[(4-cyclopropylpyridin-2-yl)amino]-4-methylpyridin-2-yl}-1,3-thiazol-2-yl)-4-hydroxy-2,2-dimethylcyclohexanecarboxylate;

4-hydroxy-2,2-dimethyl-4-[5-(4-methyl-6-{[4-(trifluoromethyl)pyridin-2-yl]amino}pyridin-2-yl)-1,3-thiazol-2-yl]cyclohexanecarboxylic acid;

(1R,4S)-4-[5-(4-amino-6-{[4-(trifluoromethyl)pyridin-2-yl]amino}pyridin-2-yl)-1,3-thiazol-2-yl]-4-hydroxy-2,2-dimethylcyclohexanecarboxylic acid;

(1S,4R)-4-[5-(4-amino-6-{[4-(trifluoromethyl)pyridin-2-yl]amino}pyridin-2-yl)-1,3-thiazol-2-yl]-4-hydroxy-2,2-dimethylcyclohexanecarboxylic acid;

methyl 4-{5-[4-(acetylamino)-6-{[4-(trifluoromethyl)pyridin-2-yl]amino}pyridin-2-yl]-1,3-thiazol-2-yl}-4-hydroxy-2,2-dimethylcyclohexanecarboxylate;

methyl 4-[5-(4-amino-6-{[4-(trifluoromethyl)pyridin-2-yl]amino}pyridin-2-yl)-1,3-thiazol-2-yl]-4-hydroxy-2,2-dimethylcyclohexanecarboxylate;

cis-4-(5-(6-((4-(1H-1,2,3-triazol-4-yl)pyridin-2-yl)amino)-4-methylpyridin-2-yl)thiazol-2-yl)-4-hydroxycyclohexanecarboxylic acid;

cis-4-hydroxy-4-{5-[6-({4-[1-(4-methoxybenzyl)-1H-1,2,3-triazol-4-yl]pyridin-2-yl}amino)-4-methylpyridin-2-yl]-1,3-thiazol-2-yl}cyclohexanecarboxylic acid;

cis-4-(5-{6-[(4-{3-[(tert-butoxycarbonyl)amino]propoxy}pyridin-2-yl)amino]-4-methylpyridin-2-yl}-1,3-thiazol-2-yl)-4-hydroxycyclohexanecarboxylic acid;

cis-4-hydroxy-4-[5-(4-methyl-6-{[4-(1-methyl-1H-1,2,3-triazol-4-yl)pyridin-2-yl]amino}pyridin-2-yl)-1,3-thiazol-2-yl]cyclohexanecarboxylic acid;

ethyl cis-4-hydroxy-4-[5-(4-methyl-6-{[4-(1-methyl-1H-1,2,3-triazol-4-yl)pyridin-2-yl]amino}pyridin-2-yl)-1,3-thiazol-2-yl]cyclohexanecarboxylate;

ethyl cis-4-hydroxy-4-[5-(4-methyl-6-{[4-(2-methyl-2H-1,2,3-triazol-4-yl)pyridin-2-yl]amino}pyridin-2-yl)-1,3-thiazol-2-yl]cyclohexanecarboxylate;

cis-4-[5-(6-{[4-(carboxymethyl)pyridin-2-yl]amino}-4-methylpyridin-2-yl)-1,3-thiazol-2-yl]-4-hydroxycyclohexanecarboxylic acid;

2-({6-[2-(cis-4-carboxy-1-hydroxycyclohexyl)-1,3-thiazol-5-yl]-4-methylpyridin-2-yl}amino)pyridine-4-carboxylic acid;

ethyl cis-4-hydroxy-4-[5-(6-{[4-(2-methoxy-2-oxoethyl)pyridin-2-yl]amino}-4-methylpyridin-2-yl)-1,3-thiazol-2-yl]cyclohexanecarboxylate;

methyl 2-[(6-{2-[cis-4-(ethoxycarbonyl)-1-hydroxycyclohexyl]-1,3-thiazol-5-yl}-4-methylpyridin-2-yl)amino]pyridine-4-carboxylate;

cis-4-[5-(6-{[4-(3-aminopropoxyl)pyridin-2-yl]amino}-4-methylpyridin-2-yl)-1,3-thiazol-2-yl]-4-hydroxycyclohexanecarboxylic acid;

cis-4-hydroxy-4-[5-(4-methyl-6-{[4-(piperidin-4-yloxy)pyridin-2-yl]amino}pyridin-2-yl)-1,3-thiazol-2-yl]cyclohexanecarboxylic acid;

ethyl cis-4-hydroxy-4-[5-(4-methyl-6-{[4-(1H-1,2,3-triazol-4-yl)pyridin-2-yl]amino}pyridin-2-yl)-1,3-thiazol-2-yl]cyclohexanecarboxylate;

ethyl cis-4-hydroxy-4-{5-[6-({4-[1-(4-methoxybenzyl)-1H-1,2,3-triazol-4-yl]pyridin-2-yl}amino)-4-methylpyridin-2-yl]-1,3-thiazol-2-yl}cyclohexanecarboxylate;

(1S,4R)-4-hydroxy-2,2-dimethyl-4-[5-(4-methyl-6-{[4-(trifluoromethyl)pyridin-2-yl]amino}pyridin-2-yl)-1,3-thiazol-2-yl]cyclohexanecarboxylic acid;

(1S,4R)-4-hydroxy-2,2-dimethyl-4-[5-(4-methyl-6-{[4-(trifluoromethyl)pyridin-2-yl]amino}pyridin-2-yl)-1,3-thiazol-2-yl]cyclohexanecarboxylic acid;

(1R,4S)-4-(5-{6-[(4-tert-butylpyridin-2-yl)amino]pyridin-2-yl}-1,3-thiazol-2-yl)-4-hydroxy-2,2-dimethylcyclohexanecarboxylic acid;

(1S,4R)-4-(5-{6-[(4-tert-butylpyridin-2-yl)amino]pyridin-2-yl}-1,3-thiazol-2-yl)-4-hydroxy-2,2-dimethylcyclohexanecarboxylic acid;

(1R,4S)-4-hydroxy-2,2-dimethyl-4-[5-(6-{[4-(trifluoromethyl)pyridin-2-yl]amino}pyridin-2-yl)-1,3-thiazol-2-yl]cyclohexanecarboxylic acid;

(1S,4R)-4-hydroxy-2,2-dimethyl-4-[5-(6-{[4-(trifluoromethyl)pyridin-2-yl]amino}pyridin-2-yl)-1,3-thiazol-2-yl]cyclohexanecarboxylic acid;

(1R,4S)-4-(5-{6-[(5-fluoro-4-methylpyridin-2-yl)amino]pyridin-2-yl}-1,3-thiazol-2-yl)-4-hydroxy-2,2-dimethylcyclohexanecarboxylic acid;

(1S,4R)-4-(5-{6-[(5-fluoro-4-methylpyridin-2-yl)amino]pyridin-2-yl}-1,3-thiazol-2-yl)-4-hydroxy-2,2-dimethylcyclohexanecarboxylic acid;

(1R,4S)-4-(5-{6-[(4-chloropyridin-2-yl)amino]pyridin-2-yl}-1,3-thiazol-2-yl)-4-hydroxy-2,2-dimethylcyclohexanecarboxylic acid;

(1S,4R)-4-(5-{6-[(4-chloropyridin-2-yl)amino]pyridin-2-yl}-1,3-thiazol-2-yl)-4-hydroxy-2,2-dimethylcyclohexanecarboxylic acid;

(1R,4S)-4-(5-{6-[(5-fluoropyridin-2-yl)amino]pyridin-2-yl}-1,3-thiazol-2-yl)-4-hydroxy-2,2-dimethylcyclohexanecarboxylic acid;

(1S,4R)-4-(5-{6-[(5-fluoropyridin-2-yl)amino]pyridin-2-yl}-1,3-thiazol-2-yl)-4-hydroxy-2,2-dimethylcyclohexanecarboxylic acid;

(1R,4S)-4-(5-{6-[(5-chloro-4-methylpyridin-2-yl)amino]pyridin-2-yl}-1,3-thiazol-2-yl)-4-hydroxy-2,2-dimethylcyclohexanecarboxylic acid;

(1S,4R)-4-(5-{6-[(5-chloro-4-methylpyridin-2-yl)amino]pyridin-2-yl}-1,3-thiazol-2-yl)-4-hydroxy-2,2-dimethylcyclohexanecarboxylic acid;

(1R,4S)-4-hydroxy-2,2-dimethyl-4-(5-{6-[(4-methylpyridin-2-yl)amino]pyridin-2-yl}-1,3-thiazol-2-yl)cyclohexanecarboxylic acid;

(1S,4R)-4-hydroxy-2,2-dimethyl-4-(5-{6-[(4-methylpyridin-2-yl)amino]pyridin-2-yl}-1,3-thiazol-2-yl)cyclohexanecarboxylic acid;

(1R,4S)-4-(5-{6-[(5-chloro-4-methylpyridin-2-yl)amino]-4-methylpyridin-2-yl}-1,3-thiazol-2-yl)-4-hydroxy-2,2-dimethylcyclohexanecarboxylic acid;

(1S,4R)-4-(5-{6-[(5-chloro-4-methylpyridin-2-yl)amino]-4-methylpyridin-2-yl}-1,3-thiazol-2-yl)-4-hydroxy-2,2-dimethylcyclohexanecarboxylic acid;

(1R,4S)-4-hydroxy-4-(5-{6-[(4-methoxypyridin-2-yl)amino]-4-methylpyridin-2-yl}-1,3-thiazol-2-yl)-2,2-dimethylcyclohexanecarboxylic acid;

(1S,4R)-4-hydroxy-4-(5-{6-[(4-methoxypyridin-2-yl)amino]-4-methylpyridin-2-yl}-1,3-thiazol-2-yl)-2,2-dimethylcyclohexanecarboxylic acid;

(1R,4S)-4-(5-{6-[(5-fluoro-4-methylpyridin-2-yl)amino]-4-methylpyridin-2-yl}-1,3-thiazol-2-yl)-4-hydroxy-2,2-dimethylcyclohexanecarboxylic acid;

(1S,4R)-4-(5-{6-[(5-fluoro-4-methylpyridin-2-yl)amino]-4-methylpyridin-2-yl}-1,3-thiazol-2-yl)-4-hydroxy-2,2-dimethylcyclohexanecarboxylic acid;

(1R,4S)-4-(5-{6-[(4-tert-butylpyridin-2-yl)amino]-4-methylpyridin-2-yl}-1,3-thiazol-2-yl)-4-hydroxy-2,2-dimethylcyclohexanecarboxylic acid;

(1S,4R)-4-(5-{6-[(4-tert-butylpyridin-2-yl)amino]-4-methylpyridin-2-yl}-1,3-thiazol-2-yl)-4-hydroxy-2,2-dimethylcyclohexanecarboxylic acid;

(1R,4S)-4-hydroxy-2,2-dimethyl-4-(5-{4-methyl-6-[(4-methylpyridin-2-yl)amino]pyridin-2-yl}-1,3-thiazol-2-yl)cyclohexanecarboxylic acid;

(1S,4R)-4-hydroxy-2,2-dimethyl-4-(5-{4-methyl-6-[(4-methylpyridin-2-yl)amino]pyridin-2-yl}-1,3-thiazol-2-yl)cyclohexanecarboxylic acid;

cis-2-hydroxy-2-(5-(4-methyl-6-((4-(trifluoromethyl)pyridin-2-yl)amino)pyridin-2-yl)thiazol-2-yl)spiro[3.5]nonane-carboxylic acid;

trans-2-hydroxy-2-[5-(4-methyl-6-{[4-(trifluoromethyl)pyridin-2-yl]amino}pyridin-2-yl)-1,3-thiazol-2-yl]spiro[3.5]nonane-7-carboxylic acid;

trans-3-hydroxy-3-[5-(4-methyl-6-{[4-(trifluoromethyl)pyridin-2-yl]amino}pyridin-2-yl)-1,3-thiazol-2-yl]bicyclo[3.2.1]octane-8-carboxylic acid;

cis-3-hydroxy-3-[5-(4-methyl-6-{[4-(trifluoromethyl)pyridin-2-yl]amino}pyridin-2-yl)-1,3-thiazol-2-yl]bicyclo[3.2.1]octane-8-carboxylic acid;

cis-4-hydroxy-4-[5-(4-methyl-6-{[4-(1-methylethoxyl)pyridin-2-yl]amino}pyridin-2-yl)-1,3-thiazol-2-yl]cyclohexanecarboxylic acid;

cis-4-hydroxy-4-[5-(4-methyl-6-{[4-(trifluoromethyl)pyridin-2-yl]amino}pyridin-2-yl)-1,3-thiazol-2-yl]cyclohexanecarboxylic acid;

(1R,4S)-4-hydroxy-4-{5-[4-(methoxymethyl)-6-{[4-(trifluoromethyl)pyridin-2-yl]amino}pyridin-2-yl]-1,3-thiazol-2-yl}-2,2-dimethylcyclohexanecarboxylic acid;

(1S,4R)-4-hydroxy-4-{5-[4-(methoxymethyl)-6-{[4-(trifluoromethyl)pyridin-2-yl]amino}pyridin-2-yl]-1,3-thiazol-2-yl}-2,2-dimethylcyclohexanecarboxylic acid;

methyl (1R,4S)-4-hydroxy-4-{5-[4-(methoxymethyl)-6-{[4-(trifluoromethyl)pyridin-2-yl]amino}pyridin-2-yl]-1,3-thiazol-2-yl}-2,2-dimethylcyclohexanecarboxylate;

methyl (1S,4R)-4-hydroxy-4-{5-[4-(methoxymethyl)-6-{[4-(trifluoromethyl)pyridin-2-yl]amino}pyridin-2-yl]-1,3-thiazol-2-yl}-2,2-dimethylcyclohexanecarboxylate;

rel-(1S,2R,4R)-4-(5-(6-((5-fluoro-4-methylpyridin-2-yl)amino)-4-methylpyridin-2-yl)thiazol-2-yl)-4-hydroxy-2-methylcyclohexanecarboxylic acid;

rel-(1S,2R,4S)-4-(5-(6-((5-fluoro-4-methylpyridin-2-yl)amino)-4-methylpyridin-2-yl)thiazol-2-yl)-4-hydroxy-2-methylcyclohexanecarboxylic acid; and rel-(1S,2R)-4-hydroxy-4-(5-(6-((4-hydroxypyridin-2-yl)amino)-4-methylpyridin-2-yl)thiazol-2-yl)-2-methylcyclohexanecarboxylic acid.

The invention also provides a compound of Formula (I) or a pharmaceutically acceptable salt thereof in purified form.

Uses of the Compounds

Compounds of Formula (I) or its pharmaceutically acceptable salts and pharmaceutical compositions containing such compounds can be used to treat or prevent a variety of conditions or diseases mediated by Spleen tyrosine kinase (Syk). Such conditions and diseases include, but are not limited to: (1) arthritis, including rheumatoid arthritis, juvenile arthritis, psoriatic arthritis and osteoarthritis; (2) asthma and other obstructive airways diseases, including chronic asthma, late asthma, severe asthma, asthma exacerbations, airway hyper-responsiveness, bronchitis, bronchial asthma, allergic asthma, intrinsic asthma, extrinsic asthma, dust asthma, adult respiratory distress syndrome, recurrent airway obstruction, and chronic obstruction pulmonary disease including emphysema; (3) autoimmune diseases or disorders, including those designated as single organ or single cell-type autoimmune disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia including idiopathic thrombopenic purpura, sympathetic ophthalmia, myasthenia gravis, Graves' disease, primary biliary cirrhosis, chronic aggressive hepatitis, ulcerative colitis and membranous glomerulopathy, those designated as involving systemic autoimmune disorder, for example systemic lupus erythematosis, immune thrombocytopenic purpura, rheumatoid arthritis, Sjogren's syndrome, Reiter's syndrome, polymyositis-dermatomyositis, systemic sclerosis, polyarteritis nodosa, multiple sclerosis and bullous pemphigoid, and additional autoimmune diseases, which can be B-cell (humoral) based or T-cell based, including Cogan's syndrome, ankylosing spondylitis, Wegener's granulomatosis, autoimmune alopecia, Type I or juvenile onset diabetes, and thyroiditis; (4) cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma and leukemia (including but not limited to acute myelogenous leukemia, chronic myelogenous leukemia, mantle cell lymphoma, NHL B cell lymphomas (e.g., precursor B-ALL, marginal zone B cell lymphoma, chronic lymphocytic leukemia, diffuse large B cell lymphoma, Burkitt lymphoma, mediastinal large B-cell lymphoma), Hodgkin lymphoma, NK and T cell lymphomas; TEL-Syk and ITK-Syk fusion driven tumors) myelomas including multiple myeloma, myeloproliferative disorders kidney cancer, lung cancer, muscle cancer, bone cancer, bladder cancer, brain cancer, melanoma including oral and metastatic melanoma, Kaposi's sarcoma, proliferative diabetic retinopathy, and angiogenic-associated disorders including solid tumors, and pancreatic cancer; (5) diabetes, including Type I diabetes and complications from diabetes; (6) eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization; (7) intestinal inflammations, allergies or conditions including Crohn's disease and/or ulcerative colitis, inflammatory bowel disease, coeliac diseases, proctitis, eosinophilic gastroenteritis, and mastocytosis; (8) neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemica, renal ischemia, heart attacks, cardiac hypertrophy, atherosclerosis and arteriosclerosis, organ hypoxia; (9) platelet aggregation and diseases associated with or caused by platelet activation, such as arteriosclerosis, thrombosis, intimal hyperplasia and restenosis following vascular injury; (10) conditions associated with cardiovascular diseases, including restenosis, acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, conditions requiring the fitting of prosthetic devices, and the like; (11) skin diseases, conditions or disorders including atopic dermatitis, eczema, psoriasis, scleroderma, pruritus and other pruritic conditions; (12) allergic reactions including anaphylaxis, allergic rhinitis, allergic dermatitis, allergic urticaria, angioedema, allergic asthma, or allergic reaction to insect bites, food, drugs, or pollen; (13) transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, and xeno transplantation; (14) low grade scarring including scleroderma, increased fibrosis, cystic fibrosis, keloids, post-surgical scars, pulmonary fibrosis, vascular spasms, migraine, reperfusion injury, and post-myocardial infarction.

The invention thus provides compounds of Formula (I) and pharmaceutically acceptable salts thereof for use in therapy, and particularly in the treatment of diseases and conditions mediated by inappropriate Syk activity. The inappropriate Syk activity referred to herein is any Syk activity that deviates from the normal Syk activity expected in a particular patient. Inappropriate Syk activity may take the form of, for instance, an abnormal increase in activity, or an aberration in the timing and or control of Syk activity. Such inappropriate activity may result then, for example, from overexpression or mutation of the protein kinase leading to inappropriate or uncontrolled activation.

In a further embodiment, the present invention is directed to methods of regulating, modulating, or inhibiting Syk for the prevention and/or treatment of disorders related to unregulated Syk activity.

In a further embodiment, the present invention provides a method of treatment of a patient suffering from a disorder mediated by Syk activity, which comprises administering to said patient an effective amount of a compound of Formula (I) or a pharmaceutically acceptable salt, solvate, or a physiologically functional derivative thereof. In a further embodiment, the present invention provides for the use of a compound of Formula (I), or a pharmaceutically acceptable salt or solvate thereof, or a physiologically functional derivative thereof, in the preparation of a medicament for the treatment of a disorder mediated by Syk activity.

In a further embodiment said disorder mediated by Syk activity is asthma. In a further embodiment said disorder is rheumatoid arthritis. In yet another embodiment, said disorder is cancer. In a further embodiment said disorder is ocular conjunctivitis.

Yet another aspect of the present invention provides a method for treating diseases caused by or associated with Fc receptor signaling cascades, including FceRI and/or FcgRI-mediated degranulation as a therapeutic approach towards the treatment or prevention of diseases characterized by, caused by and/or associated with the release or synthesis of chemical mediators of such Fc receptor signaling cascades or degranulation. In addition, Syk is known to play a critical role in immunotyrosine-based activation motif (ITAM) signaling, B cell receptor signaling, T cell receptor signaling and is an essential component of integrin beta (1), beta (2), and beta (3) signaling in neutrophils. Thus, compounds of the present invention can be used to regulate Fc receptor, ITAM, B cell receptor and integrin signaling cascades, as well as the cellular responses elicited through these signaling cascades. Non-limiting examples of cellular responses that may be regulated or inhibited include respiratory burst, cellular adhesion, cellular degranulation, cell spreading, cell migration, phagocytosis, calcium ion flux, platelet aggregation and cell maturation.

Compositions and Administration

While it is possible that, for use in therapy, a compound of Formula (I), as well as pharmaceutically acceptable salts thereof, may be administered as the raw chemical, it is possible to present the active ingredient as a pharmaceutical composition. Accordingly, the invention further provides a pharmaceutical composition, which comprises a compound of Formula (I) and pharmaceutically acceptable salts thereof, and a pharmaceutically acceptable carrier. The compounds of the Formula (I) and pharmaceutically acceptable salts thereof, are as described above. The carriers must be acceptable in the sense of being compatible with the other ingredients of the formulation and not deleterious to the recipient thereof. In accordance with another aspect of the invention there is also provided a process for the preparation of a pharmaceutical composition including admixing a compound of the Formula (I), or a pharmaceutically acceptable salt thereof, with one or more pharmaceutically acceptable carriers.

Pharmaceutical compositions of the present invention may be presented in unit dose forms containing a predetermined amount of active ingredient per unit dose. Such a unit may contain, for example, 5 g to 1 g, preferably 1 mg to 700 mg, more preferably 5 mg to 100 mg of a compound of the Formula (I), depending on the condition being treated, the route of administration and the age, weight and condition of the patient. Such unit doses may therefore be administered more than once a day. Preferred unit dosage compositions are those containing a daily dose or sub-dose (for administration more than once a day), as herein above recited, or an appropriate fraction thereof, of an active ingredient. Furthermore, such pharmaceutical compositions may be prepared by any of the methods well known in the pharmacy art.

Pharmaceutical compositions of the present invention may be adapted for administration by any appropriate route, for example by the oral (including buccal or sublingual), rectal, topical, inhaled, nasal, ocular, or parenteral (including intravenous and intramuscular) route. Such compositions may be prepared by any method known in the art of pharmacy, for example by bringing into association the active ingredient with the carrier(s) or excipient(s). Dosage forms include tablets, troches, dispersions, suspensions, solutions, capsules, creams, ointments, aerosols, and the like.

In a further embodiment, the present invention provides a pharmaceutical composition adapted for administration by the oral route, for treating, for example, rheumatoid arthritis.

In a further embodiment, the present invention provides a pharmaceutical composition adapted for administration by the nasal route, for treating, for example, allergic rhinitis.

In a further embodiment, the present invention provides a pharmaceutical composition adapted for administration by the inhaled route, for treating, for example, asthma, COPD or ARDS.

In a further embodiment, the present invention provides a pharmaceutical composition adapted for administration by the ocular route, for treating, diseases of the eye, for example, conjunctivitis.

In a further embodiment, the present invention provides a pharmaceutical composition adapted for administration by the parenteral (including intravenous) route, for treating, for example, cancer.

Pharmaceutical compositions of the present invention which are adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The formulation can also be prepared to prolong or sustain the release, for example, by coating or embedding particulate material in polymers, wax or the like.

The compounds of Formula (I) and pharmaceutically acceptable salts thereof can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of Formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Dosage forms for inhaled administration may conveniently be formulated as aerosols or dry powders.

For compositions suitable and/or adapted for inhaled administration, it is preferred that the compound or salt of Formula (I) is in a particle-size-reduced form, and more preferably the size-reduced form is obtained or obtainable by micronisation. The preferable particle size of the size-reduced (e.g., micronised) compound or salt or solvate is defined by a D50 value of about 0.5 to about 10 microns (for example as measured using laser diffraction).

Aerosol formulations, e.g., for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g., co-solvents and/or surfactants to improve the dispersion characteristics and homogeneity of suspension formulations. Solution formulations may also require the addition of co-solvents such as ethanol. Other excipient modifiers may also be incorporated to improve, for example, the stability and/or taste and/or fine particle mass characteristics (amount and/or profile) of the formulation.

For pharmaceutical compositions suitable and/or adapted for inhaled administration, it is preferred that the pharmaceutical composition is a dry powder inhalable composition. Such a composition can comprise a powder base such as lactose, glucose, trehalose, mannitol or starch, the compound of Formula (I) or salt or solvate thereof (preferably in particle-size-reduced form, e.g., in micronised form), and optionally a performance modifier such as L-leucine or another amino acid, and/or metals salts of stearic acid such as magnesium or calcium stearate. Preferably, the dry powder inhalable composition comprises a dry powder blend of lactose and the compound of Formula (I) or salt thereof. The lactose is preferably lactose hydrate e.g., lactose monohydrate and/or is preferably inhalation-grade and/or fine-grade lactose. Preferably, the particle size of the lactose is defined by 90% or more (by weight or by volume) of the lactose particles being less than 1000 microns (micrometers) (e.g., 10-1000 microns e.g., 30-1000 microns) in diameter, and/or 50% or more of the lactose particles being less than 500 microns (e.g., 10-500 microns) in diameter. More preferably, the particle size of the lactose is defined by 90% or more of the lactose particles being less than 300 microns (e.g., 10-300 microns e.g., 50-300 microns) in diameter, and/or 50% or more of the lactose particles being less than 100 microns in diameter. Optionally, the particle size of the lactose is defined by 90% or more of the lactose particles being less than 100-200 microns in diameter, and/or 50% or more of the lactose particles being less than 40-70 microns in diameter. It is preferable that about 3 to about 30% (e.g., about 10%) (by weight or by volume) of the particles are less than 50 microns or less than 20 microns in diameter. For example, without limitation, a suitable inhalation-grade lactose is E9334 lactose (10% fines) (Borculo Domo Ingredients, Hanzeplein 25, 8017 J D Zwolle, Netherlands).

Optionally, in particular for dry powder inhalable compositions, a pharmaceutical composition for inhaled administration can be incorporated into a plurality of sealed dose containers (e.g., containing the dry powder composition) mounted longitudinally in a strip or ribbon inside a suitable inhalation device. The container is rupturable or peel-openable on demand and the dose of e.g., the dry powder composition can be administered by inhalation via the device such as the DISKUS® device (GlaxoSmithKline). Other dry powder inhalers are well known to those of ordinary skill in the art, and many such devices are commercially available, with representative devices including Aerolizer® (Novartis), Airmax™ (IVAX), ClickHaler® (Innovata Biomed), Diskhaler® (GlaxoSmithKline), Accuhaler (GlaxoSmithKline), Easyhaler® (Orion Pharma), Eclipse™ (Aventis), FlowCaps® (Hovione), Handihaler® (Boehringer Ingelheim), Pulvinal® (Chiesi), Rotahaler® (GlaxoSmithKline), SkyeHaler™ or Certihaler™ (SkyePharma), Twisthaler (Schering Corporation), Turbuhaler® (AstraZeneca), Ultrahaler® (Aventis), and the like.

Dosage forms for ocular administration may be formulated as solutions or suspensions with excipients suitable for ophthalmic use.

Dosage forms for nasal administration may conveniently be formulated as aerosols, solutions, drops, gels or dry powders.

Pharmaceutical compositions adapted for administration by inhalation include fine particle dusts or mists, which may be generated by means of various types of metered, dose pressurised aerosols, nebulizers or insufflators.

For pharmaceutical compositions suitable and/or adapted for intranasal administration, the compound of Formula (I) or a pharmaceutically acceptable salt or solvate thereof may be formulated as a fluid formulation for delivery from a fluid dispenser. Such fluid dispensers may have, for example, a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. A particularly preferred fluid dispenser is of the general type illustrated in FIGS. 30-40 of WO-A-2005/044354.

The following are examples of representative pharmaceutical dosage forms for the compounds of this invention:

| Injectable Suspension (I.M.) | mg/mL |
| --- | --- |
| Compound of Formula (I) | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Tablet | mg/tablet |
| --- | --- |
| Compound of Formula (I) | 25 |
| Microcrystalline Cellulose | 415 |
| Providone | 14.0 |
| Pregelatinized Starch | 43.5 |
| Magnesium Stearate | 2.5 |
| | 500 |

| Capsule | mg/capsule |
|---|---|
| Compound of Formula (I) | 25 |
| Lactose Powder | 573.5 |
| Magnesium Stearate | 1.5 |
| | 600 |

| Aerosol | Per canister |
|---|---|
| Compound of Formula (I) | 24 mg |
| Lecithin, NF Liquid Concentrate | 1.2 mg |
| Trichlorofluoromethane, NF | 4.025 gm |
| Dichlorodifluoromethane, NF | 12.15 gm |

It will be appreciated that when the compound of the present invention is administered in combination with other therapeutic agents normally administered by the inhaled, intravenous, oral or intranasal route, that the resultant pharmaceutical composition may be administered by the same routes.

It should be understood that in addition to the ingredients particularly mentioned above, the compositions may include other agents conventional in the art having regard to the type of formulation in question, for example those suitable for oral administration may include flavouring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of Formula (I) for the treatment of diseases or conditions associated with inappropriate Syk activity, will generally be in the range of 5 µg to 100 mg/kg body weight of recipient (patient) per day and more usually in the range of 5 µg to 10 mg/kg body weight per day. This amount may be given in a single dose per day or more usually in a number (such as two, three, four, five or six) of sub-doses per day such that the total daily dose is the same. An effective amount of a salt or solvate, thereof, may be determined as a proportion of the effective amount of the compound of Formula (I) per se.

The compositions of the invention can further comprise one or more additional therapeutic agents, as discussed in further detail below. Accordingly, in one embodiment, the present invention provides compositions comprising: (i) a compound of Formula (I) or a pharmaceutically acceptable salt thereof; (ii) one or more additional therapeutic agents, that are not compounds of Formula (I); and (iii) a pharmaceutically acceptable carrier, wherein the amounts in the composition are together effective to treat one of the disease or conditions discussed above.

Combination Therapy

The compounds of Formula (I) or their pharmaceutically acceptable salts may be used in combination, either in a single formulation or co-administered as separate formulations with at least one additional therapeutic agent to treat or prevent the diseases and conditions described herein. For the treatment of the inflammatory diseases, rheumatoid arthritis, psoriasis, inflammatory bowel disease, COPD, asthma and allergic rhinitis, these additional therapeutic agents include, but are not limited to: (1) TNF-α inhibitors such as infliximab (Remicade®), etanercept (Enbrel®), adalimumab (Humira®), certolizumab pegol (Cimzia®), and golimumab (Simponi®); (2) non-selective COX-I/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, etodolac, azapropazone, pyrazolones such as phenylbutazone, salicylates such as aspirin); (3) COX-2 inhibitors (such as meloxicam, celecoxib, rofecoxib, valdecoxib and etoricoxib); (4) other agents for treatment of rheumatoid arthritis including methotrexate, leflunomide, sulfasalazine, azathioprine, cyclosporin, tacrolimus, penicillamine, bucillamine, actarit, mizoribine, lobenzarit, ciclesonide, hydroxychloroquine, d-penicillamine, aurothiomalate, auranofin or parenteral or oral gold, cyclophosphamide, Lymphostat-B, BAFF/APRIL inhibitors and CTLA-4-Ig or mimetics thereof; (5) leukotriene biosynthesis inhibitor, 5-lipoxygenase (5-LO) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast, cilomilast, AWD-12-281 (Elbion), and PD-168787 (Pfizer); (8) antihistaminic H1 receptor antagonists such as cetirizine, levocetirizine, loratadine, desloratadine, fexofenadine, astemizole, azelastine, levocabastine, olopatidine, methapyrilene and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (10) anticholinergic agents such as ipratropium bromide, tiotropium bromide, oxitropium bromide, aclidinium bromide, glycopyrrolate, (R,R)-glycopyrrolate, pirenzepine, and telenzepine; (11) β-adrenoceptor agonists such as metaproterenol, isoproterenol, isoprenaline, albuterol, formoterol (particularly the fumarate salt), salmeterol (particularly the xinafoate salt), terbutaline, orciprenaline, bitolterol mesylate, fenoterol, and pirbuterol, or methylxanthanines including theophylline and aminophylline, sodium cromoglycate; (12) insulin-like growth factor type I (IGF-1) mimetic; (13) glucocorticosteroids, especially inhaled glucocorticoid with reduced systemic side effects, such as prednisone, prednisolone, flunisolide, triamcinolone acetonide, beclomethasone dipropionate, budesonide, fluticasone propionate, ciclesonide and mometasone furoate; (14) kinase inhibitors such as inhibitors of the Janus Kinases (JAK 1 and/or JAK2 and/or JAK 3 and/or TYK2) such as tofacitinib (Pfizer), baricitinib (Incyte), VX-509 (Vertex), ASP-015K (Astellas), GLPG0634 (Galapagos), SB-1578 (SBIO), and AC-430 (Ambit Biosciences); p38 MAPK and IKK2; (15) B-cell targeting biologics such as rituximab (Rituxan®); (16) selective costimulation modulators such as abatacept (Orencia); (17) interleukin inhibitors, such as IL-1 inhibitor anakinra (Kineret) and IL-6 inhibitor tocilizumab (Actemra).

The present invention also provides for so-called "triple combination" therapy, comprising a compound of Formula (I) or a pharmaceutically acceptable salt thereof together with beta$_2$-adrenoreceptor agonist and an anti-inflammatory corticosteroid. Preferably this combination is for treatment and/or prophylaxis of asthma, COPD or allergic rhinitis. The beta$_2$-adrenoreceptor agonist and/or the anti-inflammatory corticosteroid can be as described above and/or as described in WO 03/030939 A1. Representative examples of such a "triple" combination are a compound of Formula (I) or a pharmaceutically acceptable salt thereof in combination with the components of Advair® (salmeterol xinafoate and fluticasone propionate), Symbicort® (budesonide and formoterol fumarate), or Dulera® (mometasone furoate and formoterol fumarate).

For the treatment of cancer a compound of Formula (I) may be combined with an one or more additional therapeutic agents which are anticancer agents. Examples of such agents can be found in *Cancer Principles and Practice of Oncology* by V. T. Devita and S. Hellman (editors), 6th edition (Feb. 15, 2001), Lippincott Williams & Wilkins Publishers. A person of ordinary skill in the art would be able to discern which combinations of agents would be useful based on the particular characteristics of the drugs and the cancer involved. Such anticancer agents include, but are not limited to, the following: (1) an estrogen receptor modulator such as diethylstibestral, tamoxifen, raloxifene, idoxifene, LY353381, LY117081, toremifene, fluoxymestero, and SH646; (2) other hormonal agents including aromatase inhibitors (e.g., aminoglutethimide, tetrazole anastrozole, letrozole and exemestane), luteinizing hormone release hormone (LHRH) analogues, ketoconazole, goserelin acetate, leuprolide, megestrol acetate and mifepristone; (3) an androgen receptor modulator such as finasteride and other 5α-reductase inhibitors, nilutamide, flutamide, bicalutamide, liarozole, and abiraterone acetate; (4) a retinoid receptor modulator such as bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide; (5) an antiproliferative agent such as antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, aminopterin, 5-fluorouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, swainsonine, lometrexol, dexrazoxane, methioninase, and 3-aminopyridine-2-carboxaldehyde thiosemicarbazone; (6) a prenyl-protein transferase inhibitor including farnesyl-protein transferase (FPTase), geranylgeranyl-protein transferase type I (GGPTase-I), and geranylgeranyl-protein transferase type-II (GGPTase-II, also called Rab GGPTase); (7) an HMG-CoA reductase inhibitor such as lovastatin, simvastatin, pravastatin, atorvastatin, fluvastatin and rosuvastatin; (8) an angiogenesis inhibitor such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, erythropoietin (epoietin-α), granulocyte-CSF (filgrastin), granulocyte, macrophage-CSF (sargramostim), pentosan polysulfate, cyclooxygenase inhibitors, steroidal anti-inflammatories, carboxyamidotriazole, combretastatin A-4, squalamine, 6-O-chloroacetyl-carbonyl)-fumagillol, thalidomide, angiostatin, troponin-1, angiotensin II antagonists, heparin, carboxypeptidase U inhibitors, and antibodies to VEGF, endostatin, ukrain, ranpirnase, IM862, acetyldinanaline, 5-amino-1-[[3,5-dichloro-4-(4-chlorobenzoyl)phenyl]-methyl]-1H-1,2,3-triazole-4-carboxamide, CM101, squalamine, combretastatin, RPI4610, NX31838, sulfated mannopentaose phosphate, and 3-[(2,4-dimethylpyrrol-5-yl)methylene]-2-indolinone (SU5416); (9) PPAR-γ agonists, PPAR-δ agonists, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782, 856), and (2R)-7-(3-(2-chloro-4-(4-fluorophenoxyl)phenoxy)propoxy)-2-ethylchromane-2-carboxylic acid (disclosed in U.S. Ser. No. 60/235,708 and 60/244,697); (9) an inhibitor of inherent multidrug resistance including inhibitors of p-glycoprotein (P-gp), such as LY335979, XR9576, OC144-093, R101922, VX853 and PSC833 (valspodar); (10) an inhibitor of cell proliferation and survival signaling such as inhibitors of EGFR (for example gefitinib and erlotinib), inhibitors of ERB-2 (for example trastuzumab), inhibitors of IGF 1R such as MK-0646 (dalotuzumab), inhibitors of CD20 (rituximab), inhibitors of cytokine receptors, inhibitors of MET, inhibitors of PI3K family kinase (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779 and Ariad AP23573); (11) a bisphosphonate such as etidronate, pamidronate, alendronate, risedronate, zoledronate, ibandronate, incadronate or cimadronate, clodronate, EB-1053, minodronate, neridronate, piridronate and tiludronate; (12) γ-secretase inhibitors, (13) agents that interfere with receptor tyrosine kinases (RTKs) including inhibitors of c-Kit, Eph, PDGF, Flt3 and c-Met; (14) an agent that interferes with a cell cycle checkpoint including inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032; (15) BTK inhibitors such as PCI32765, AVL-292 and AVL-101; (16) PARP inhibitors including iniparib, olaparib, AGO14699, ABT888 and MK4827; (16) ERK inhibitors; (17) mTOR inhibitors such as sirolimus, ridaforolimus, temsirolimus, everolimus; and (18) cytotoxic/cytostatic agents.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, chlorambucil, cyclophosphamide, ifosfamide, mechlorethamine, melphalan, uracil mustard, thiotepa, busulfan, carmustine, lomustine, streptozocin, tasonermin, lonidamine, carboplatin, altretamine, dacarbazine, procarbazine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum (II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, doxorubicin, daunorubicin, idarubicin, anthracenedione, bleomycin, mitomycin C, dactinomycin, plicatomycin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin.

An example of a hypoxia activatable compound is tirapazamine.

Examples of proteasome inhibitors include but are not limited to lactacystin and bortezomib.

Examples of microtubule inhibitors/microtubule-stabilising agents include vincristine, vinblastine, vindesine, vinzolidine, vinorelbine, vindesine sulfate, 3',4'-didehydro-4'-deoxy-8'-norvincaleukoblastine, podophyllotoxins (e.g., etoposide (VP-16) and teniposide (VM-26)), paclitaxel, docetaxol, rhizoxin, dolastatin, mivobulin isethionate, auristatin, cemadotin, RPR109881, BMS184476, vinflunine, cryptophycin, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS 188797.

Some examples of topoisomerase inhibitors are topotecan, hycaptamine, irinotecan, rubitecan, 6-ethoxypropionyl-3',4'-O-exo-benzylidene-chartreusin, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, 2,3-(methylenedioxy)-5-methyl-7-hydroxy-8-methoxybenzo[c]-phenanthridinium, 5-(3-aminopropylamino)-7,10-dihydroxy-2-(2-hydroxyethylaminomethyl)-6H-pyrazolo[4,5,1-de]acridin-6-one, N-[1-[2-(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins include, but are not limited to inhibitors of KSP, inhibitors of MKLP 1, inhibitors of CENP-E, inhibitors of MCAK, inhibitors of Kifl4, inhibitors of Mphosph1 and inhibitors of Rab6-KIFL.

Examples of "histone deacetylase inhibitors" include, but are not limited to, vorinostat, trichostatin A, oxamflatin, PXD101, MG98, valproic acid and scriptaid.

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N6-[4-deoxy-4-[N2-[2,4-tetradecadienoyl]glycylamino]-L-glycero-B-L-mannoheptopyranosyl]adenine, aplidine, ecteinascidin, troxacitabine, aminopterin, 5-fluorouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, swainsonine, lometrexol, dexrazoxane, methioninase, and 3-aminopyridine-2-carboxaldehyde thiosemicarbazone.

Non-limiting examples of suitable additional therapeutic agents used in cancer therapy that may be combined with compounds of Formula (I) include, but are not limited to, abarelix; aldesleukin; alemtuzumab; alitretinoin; allopurinol; altretamine; amifostine; anastrozole; arsenic trioxide; asparaginase; azacitidine; bendamustine; bevacuzimab; bexarotene; bleomycin; bortezomib; busulfan; calusterone; capecitabine; carboplatin; carmustine; cetuximab; chlorambucil; cisplatin; cladribine; clofarabine; cyclophosphamide; cytarabine; dacarbazine; dactinomycin, actinomycin D; dalteparin; darbepoetin alfa; dasatinib; daunorubicin; degarelix; denileukin diftitox; dexrazoxane; docetaxel; doxorubicin; dromostanolone propionate; eculizumab; Elliott's B Solution; eltrombopag; epirubicin; epoetin alfa; erlotinib; estramustine; etoposide phosphate; etoposide; everolimus; exemestane; filgrastim; floxuridine; fludarabine; fluorouracil; fulvestrant; gefitinib; gemcitabine; gemtuzumab ozogamicin; goserelin acetate; histrelin acetate; hydroxyurea; ibritumomab tiuxetan; idarubicin; ifosfamide; imatinib mesylate; interferon alfa 2a; interferon alfa-2b; irinotecan; ixabepilone; lapatinib; lenalidomide; letrozole; leucovorin; leuprolide acetate; levamisole; lomustine; meclorethamine, nitrogen mustard; megestrol acetate; melphalan, L-PAM; mercaptopurine; mesna; methotrexate; methoxsalen; mitomycin C; mitotane; mitoxantrone; nandrolone phenpropionate; nelarabine; nilotinib; Nofetumomab; ofatumumab; oprelvekin; oxaliplatin; paclitaxel; palifermin; pamidronat; panitumumab; pazopanib; pegademase; pegaspargase; Pegfilgrastim; pemetrexed disodium; pentostatin; pipobroman; plerixafor; plicamycin, mithramycin); porfimer sodium; pralatrexate; procarbazine; quinacrine; Rasburicase; raloxifene hydrochloride; Rituximab; romidepsin; romiplostim; sargramostim; sargramostim; satraplatin; sorafenib; streptozocin; sunitinib maleate; tamoxifen; temozolomide; temsirolimus; teniposide; testolactone; thioguanine; thiotepa; topotecan; toremifene; tositumomab; trastuzumab; tretinoin; uracil mustard; valrubicin; vinblastine; vincristine; vinorelbine; vorinostat; and zoledronate.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like.

These combinations are of particular interest in respiratory diseases and are conveniently adapted for inhaled or intranasal delivery.

In one embodiment, the compound of Formula (I) is administered during a time when the additional therapeutic agent(s) exert their prophylactic or therapeutic effect, or vice versa.

In another embodiment, the compound of Formula (I) and the additional therapeutic agent(s) are administered in doses commonly employed when such agents are used as monotherapy for treating the disorder.

In another embodiment, the compound of Formula (I) and the additional therapeutic agent(s) are administered in doses lower than the doses commonly employed when such agents are used as monotherapy for treating the disorder.

In one embodiment, the compound of Formula (I) and the additional therapeutic agent(s) are present in the same composition, which is suitable for oral administration.

The compound of Formula (I) and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

The doses and dosage regimen of the additional therapeutic agent(s) used in the combination therapies of the present invention for the treatment or prevention of a disease or disorder can be determined by the attending clinician, taking into consideration the approved doses and dosage regimen in the package insert; the age, sex and general health of the patient; and the type and severity of the disease or condition mediated by Syk.

Another aspect of this invention is a kit comprising a therapeutically effective amount of the compound of Formula (I) or a pharmaceutically acceptable salt of said compound, optionally at least one additional therapeutic agent listed above and a pharmaceutically acceptable carrier, vehicle or diluent.

Methods of Preparing the Compounds of Formula (I)

The compounds of this invention may be made by a variety of methods, including standard chemistry. Any previously defined variable will continue to have the previously defined meaning unless otherwise indicated. Illustrative general synthetic methods are set out below and then specific compounds of the Formula (I) are prepared in the Examples.

Compounds of general Formula (I) may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) Protecting Groups in Organic Synthesis, John Wiley & Sons). These groups are removed at a convenient stage of the compound synthesis using methods that are readily apparent to those skilled in the art. The selection of protecting groups as well as the reaction conditions and order of reaction steps shall be consistent with the preparation of compounds of Formula (I). Those skilled in the art will recognize whether a stereocenter exists in compounds of Formula (I). Accordingly, the present invention includes all possible stereoisomers and includes not only mixtures of stereoisomers (such as racemic compounds) but the individual stereoisomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, Stereochemistry of Organic Compounds by E. L. Eliel, S. H. Wilen, and L. N. Mander (Wiley-Interscience, 1994).

The following solvents, reagents, protecting groups, moieties, and other designations may be referred to by their abbreviations in parenthesis:

Me=methyl; Et=ethyl; Pr=propyl; iPr=isopropyl, Bu=butyl; t-Bu32 tert-butyl; Ph=phenyl, and Ac=acetyl
μl=microliters
AcOH or HOAc=acetic acid
ACN=acetonitrile
APCI=atmospheric-pressure chemical ionization
aq=aqueous
Bn=benzyl
Boc or BOC32 tert-butoxycarbonyl
Bz=benzoyl
Boc32 tert-butoxycarbonyl
Calcd=calculated
Cbz=benzyloxycarbonyl
DCM=dichloromethane:
DMAP=4-dimethylaminopyridine
DIBAL=diisobutylaluminum hydride
DIEA or Hünig's Base=N,N-diisopropylethylamine
DMA=1,2-dimethylacetamide
DMF=dimethylformamide
DMSO=dimethyl sulfoxide
DTT=dithiothreitol
EDC=1-ethyl-3-(3-dimethylaminopropyl)carbodiimide
EDTA32 ethylenediamine tetraacetic acid
ESI=electrospray ionization
EtOAc=ethyl acetate
g=grams
GST=glutathione S-transferase
h=hour
HMDS=1,1,1,3,3,3-hexamethyldisilazane
HATU=N,N,N',N-tetramethyl-O-(7-azabenzotriazol-1-yl)uronium hexafluorophosphate
HPLC=high-performance liquid chromatography
HOBt=1-hydroxybenzotriazole
LDA=lithium diisopropylamide
LCMS=liquid chromatography mass spectrometry
min=minute
mg=milligrams
mL=milliliters
mmol=millimoles
Me=methyl
MeOH: methanol
MS=mass spectrometry
NBS=N-bromosuccimide
NMR=nuclear magnetic resonance spectroscopy
Obsvd=observed
rac=racemic mixture
RT or rt=room temperature (ambient, about 25° C.)
sat=saturated
SFC=supercritical fluid chromatography
TBSCl=t-butyldimethylsilyl chloride
TBS=t-butyldimethyl silyl
TEA=triethylamine ($Et_3N$)
TFA=trifluoroacetic acid
TFAA=trifluoroacetic anhydride
THF=tetrahydrofuran
TLC=thin layer chromatography
TMS=trimethylsilyl
Tris=tris(hydroxymethyl)aminomethane General Methods Compounds of the Formula (I) can be prepared according to one of the general synthetic schemes procedures set forth in Schemes 1-8 below, and/or by methods similar to those described in the Examples below.

Scheme 1

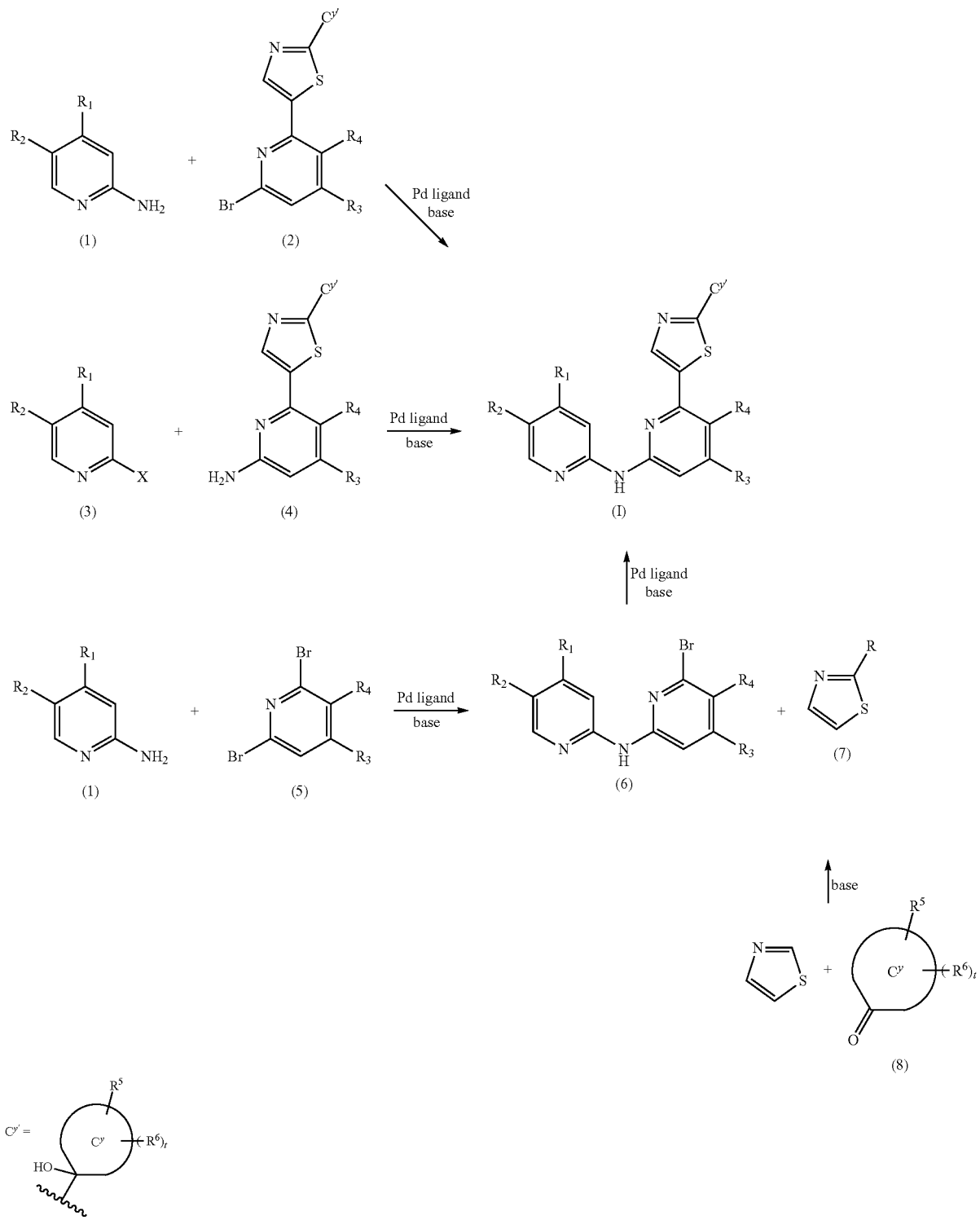

Compounds of Formula (I) are prepared by palladium-mediated coupling of substituted amino pyridines (1) with bromo pyridyl thiazoles (2) or of halo pyridines (3) with amino pyridyl thiazoles (4), as shown in Scheme 1. Alternatively, Compounds of Formula (I) are obtained by palladium-mediated coupling of substituted aminobispyridines (6) with substituted thiazoles (7). Substituted thiazoles of formula (7) are prepared by deprotonating thiazole with a strong base, such as LDA, and reacting the resultant species with an electrophile like (8). Aminobispyridines (6) are prepared by coupling of aminopyridines (1) with bis-bromo pyridines (5).

Scheme 2

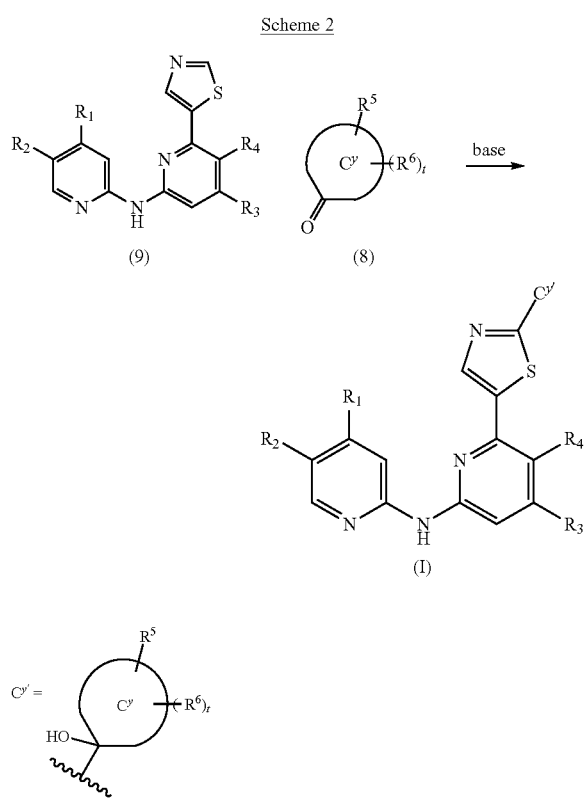

Compounds of Formula (I) are also prepared by deprotonating thiazole compounds like (9) with a strong base, such as LDA, and reacting the resultant species with an electrophile like (8), as shown in Scheme 2.

Scheme 3

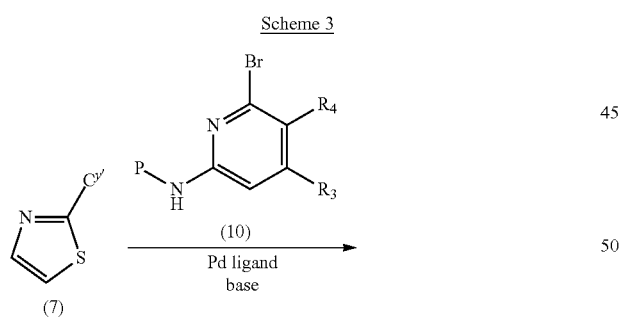

PG = protecting group

As depicted in Scheme 3, palladium-mediated coupling of the substituted thiazole (7) with an amine-protected bromopyridine (10), gives amine-protected pyridine thiazoles (11). Deprotection affords compounds of formula (4).

Scheme 4

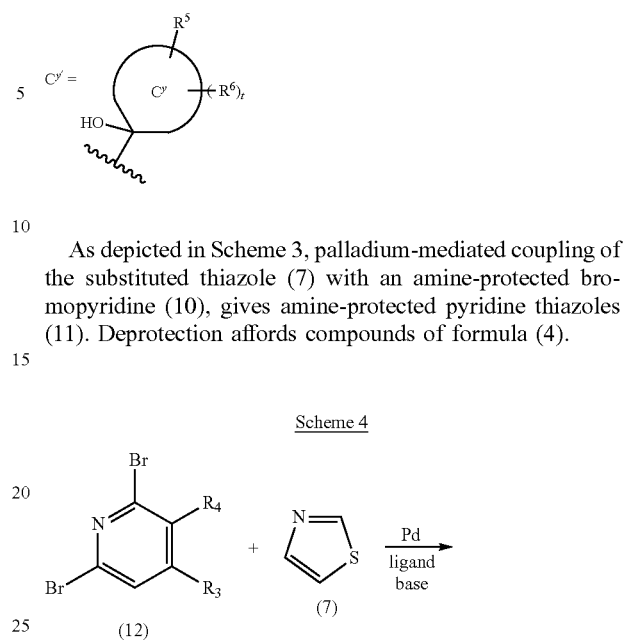

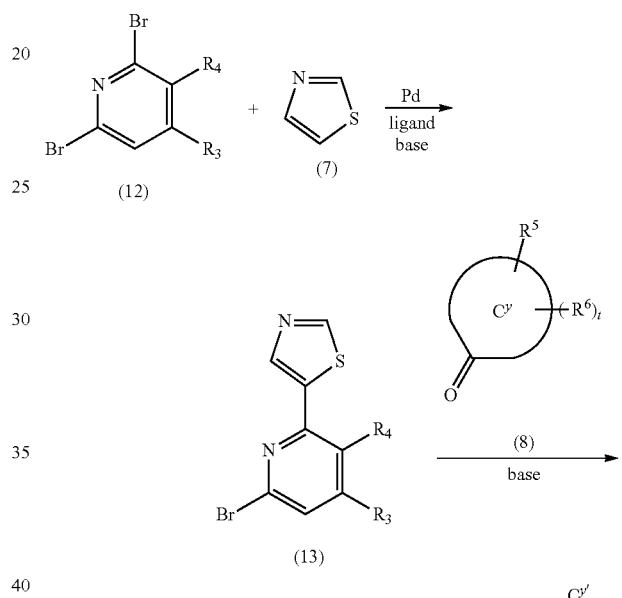

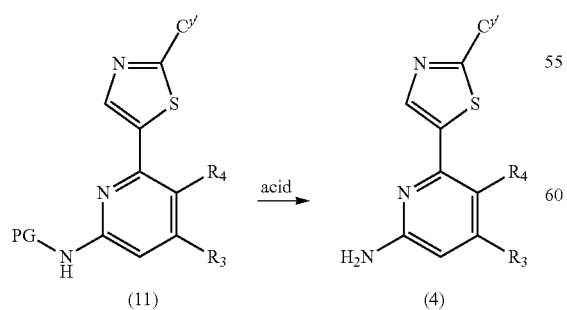

Compounds of Formula (2) are prepared by first coupling a bis-bromopyridine of type (12) with thiazole using a palladium catalyst, as shown in Scheme 4. The pyridyl thiazole (13) are deprotonated with a strong base, such as LDA, and reacted with an electrophile such as the ketone (8) to provide compounds of formula (2).

Scheme 5
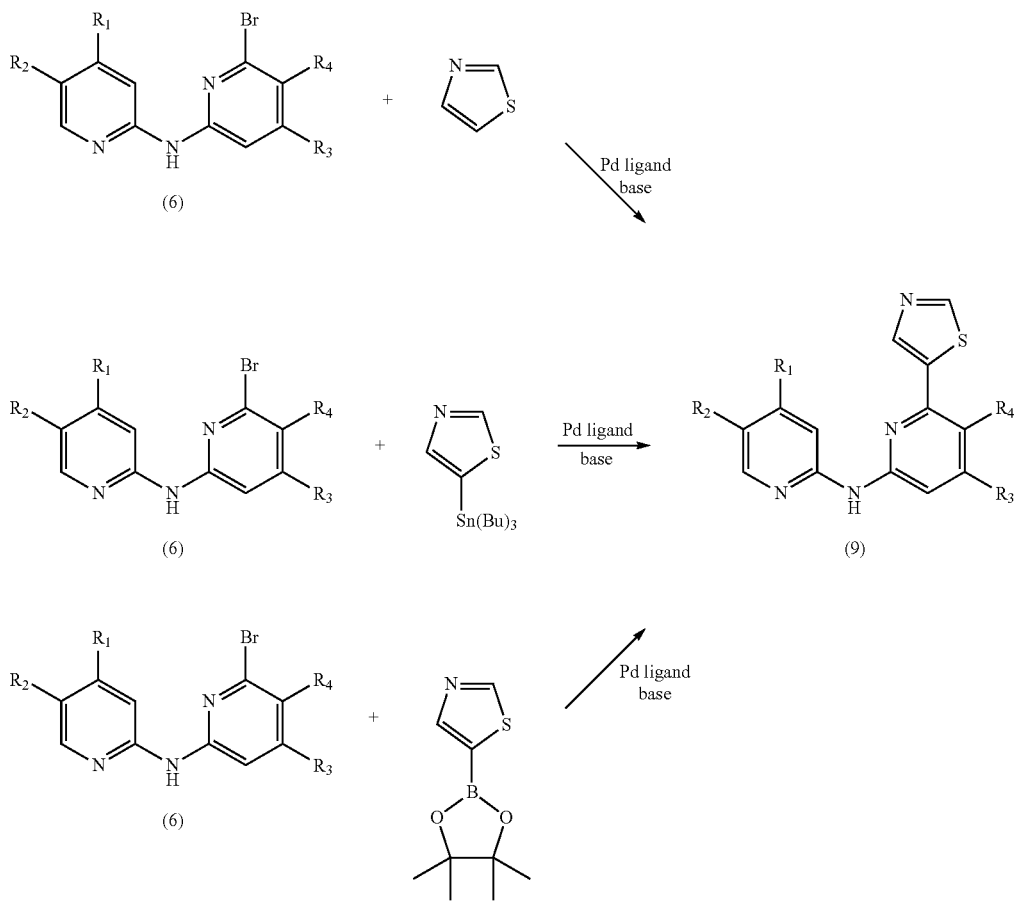
As depicted in Scheme 5, compounds of formula (9) are prepared by palladium-mediated coupling of aminobispyridines (6) with thiazole, 5-(tributylstannyl)thiazole, or 5-(4,4,5,5-tetramethyl-1,3,2-dioxaborolan-2-yl)thiazole.
Scheme 6
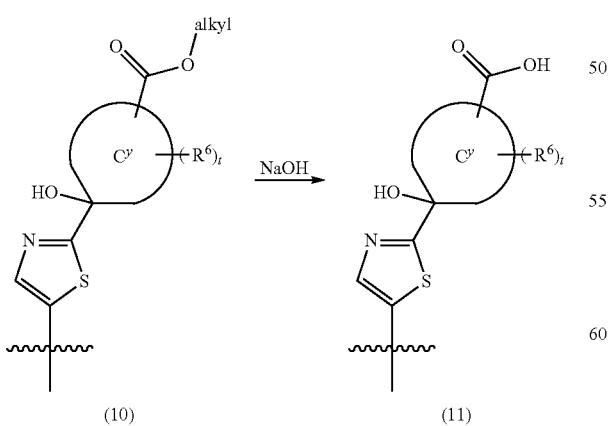
As shown in Scheme 6, carboxylic acids (11) are prepared by hydrolysis of alkyl esters (10).

Scheme 7
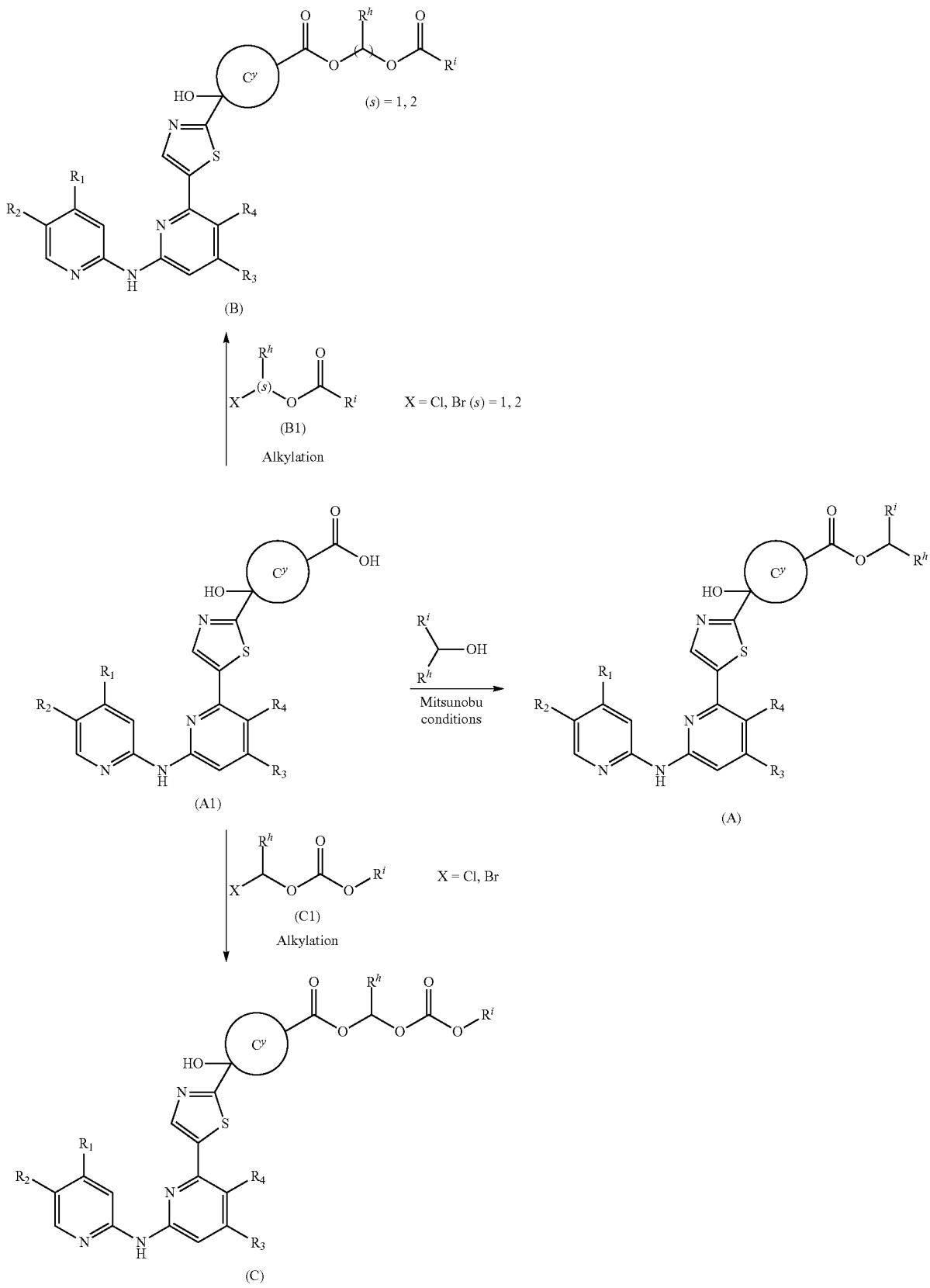

As shown in Scheme 7, compounds of structural subtype (A) are prepared from the carboxylic acid (A1) by a Mitsunobu reaction with various primary and secondary alcohols. Compounds of structural subtype (B) are prepared by the alkylation of the carboxylic acid (A1) by alkyl halides of formula (B1). Compounds of structural subtype (C) are prepared by the alkylation of the carboxylic acid (A1) by alkyl halides of formula (C1).

Scheme 8

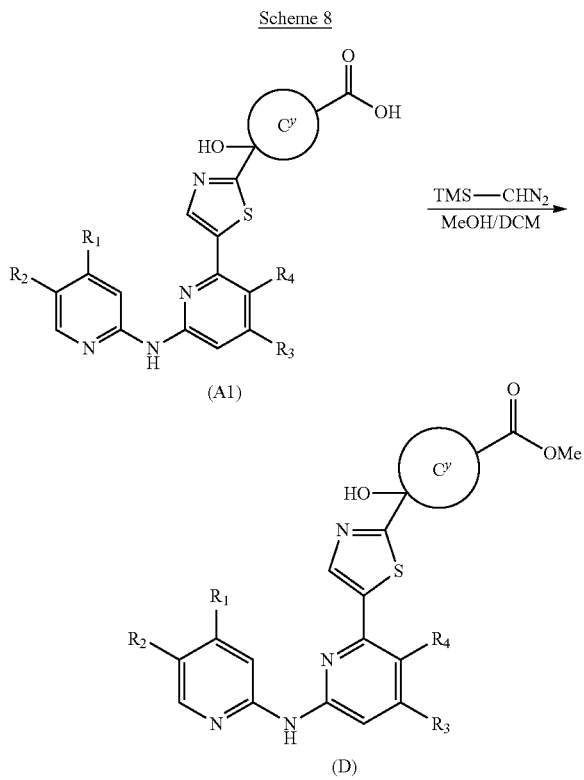

As shown in Scheme 8, compounds of structural subtype (D) are prepared by the reaction of the carboxylic acid (A1) with trimethylsilyldiazomethane and methanol.

For ease of reference, various intermediates are referred in the Examples below as precursors of various moieties of Compounds of the Formula (I). These moieties are illustrated in the structural formula below.

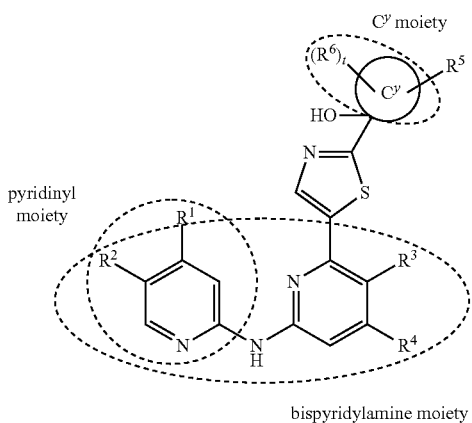

The starting materials and reagents used in preparing compounds described are either available from commercial suppliers or were prepared by literature methods known to those skilled in the art.

These examples are being provided to further illustrate the present invention. The examples provided below are for illustrative purposes only; the scope of the invention is not to be considered limited in any way thereby.

Where compounds in the examples include the designations "(R) or (S)" or "(R or S)" for a given chiral center in the molecule such designations mean that the compounds were isolated as single enantiomers and the stereochemical configurations of such compounds were not determined. Similarly, when a compound includes the designation "1R, 4S or 1S,4R", this designation means that the compound has been isolated as a single diastereomer of unknown absolute configuration.

Where mass spectral (MS) data are presented in the examples below, analysis was performed using an Agilent Technologies 6120 quadrupole LC/MS. Resolution of enantiomers was typically performed using supercritical fluid chromatography utilizing a Chiral Technologies stationary phase such as OJ-H or OJ column (stationary phase with particle size of 5 or 10 micron) with a mobile phase of $CO_2$ and a lower alcohol such as methanol or isopropanol.

EXAMPLES

Preparative Example 1

Preparation of Bispyridylamine Precursors Suitable for Coupling with $C^y$ Precursors Preparative Example 1.1

6-Bromo-4-methyl-N-[4-(trifluoromethyl)pyridine-2-yl]pyridine-2-amine

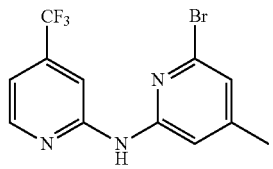

To a flask containing 2,6-dibromo-4-methyl pyridine (13.9 g, 55.5 mmol) and 2-amino-4-trifluoromethyl pyridine (9.0 g, 55.5 mmol) was added nitrogen sparged dioxane (180 mL). Sodium tert-butoxide (5.87 g, 61.1 mmol) and 1,1'-bis(di-tert-butylphosphino)ferrocene palladium dichloride (0.905 g, 1.4 mmol) were then added, and the slurry was evacuated and refilled with nitrogen. The mixture was stirred at 25° C. for 15 minutes and then heated to 75° C. for 12 hours. The reaction was cooled to 25° C., water (20 mL) was added, and the mixture was extracted with ethyl acetate (2×200 mL). The combined extracts were dried over sodium sulfate, filtered, and concentrated under reduced pressure. The residue was purified via chromatography on silica gel to afford 6-bromo-4-methyl-N-[4-(trifluoromethyl)pyridine-2-yl]pyridine-2-amine. MS ESI calcd. for $C_{12}H_{10}BrF_3N_3$ [M+H]$^+$ 332 and 334. found 332 and 334. $^1$H NMR (600 MHz, DMSO-$d_6$) δ 10.40 (s, 1H), 8.46 (d, J=6.0 Hz, 1H), 7.90 (s, 1H), 7.60 (s, 1H), 7.18 (d, J=6.0 Hz, 1H), 7.00 (s, 1H), 2.25 (s, 3H).

The intermediates in the following table were prepared according to the method described for Preparative Example 1.1.

| Prep. Ex. | Structure | Chemical Name | Exact Mass [M + H]+ | [M + H]+ Obsv'd |
|---|---|---|---|---|
| 1.2 | 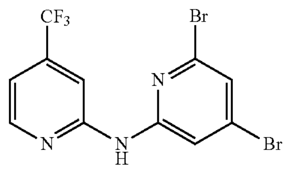 [SMILES: FC(F)(F)c1ccnc(Nc2cc(Br)cc(Br)n2)c1] | 4,6-dibromo-N-(4-(trifluoromethyl)pyridin-2-yl)pyridin-2-amine | 398 | 398 |
| 1.3 | 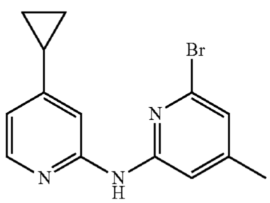 [SMILES: Cc1cc(Br)nc(Nc2cc(C3CC3)ccn2)c1] | 6-bromo-N-(4-cyclopropylpyridin-2-yl)-4-methylpyridin-2-amine | 304, 306 | 304, 306 |
| 1.4 | 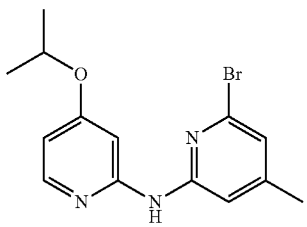 [SMILES: Cc1cc(Br)nc(Nc2cc(OC(C)C)ccn2)c1] | 6-bromo-N-(4-isopropoxypyridin-2-yl)-4-methylpyridin-2-amine | 322, 324 | * see $^1$H NMR below |

* $^1$H NMR (600 MHz, DMSO-$d_6$) δ 9.77 (s, 1H), 8.00 (d, J = 6.0 Hz, 1H), 7.58 (s, 1H), 7.13 (s, 1H), 6.88 (s, 1H), 6.47 (d, J = 6.0 Hz, 1H), 4.62-4.58 (m, 1H), 2.21 (s, 3H), 1.27 (s, 6H).

Preparative Example 1.5

6-Bromo-4-(methoxymethyl)-N-(4-(trifluoromethyl)pyridin-2-yl)pyridin-2-amine

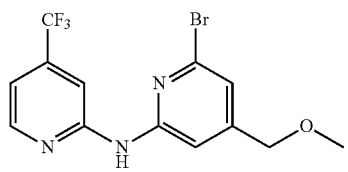

PrepEx-1.5

Step 1: To a solution of 6-bromo-4-methyl-N-(4-(trifluoromethyl)pyridin-2-yl)pyridin-2-amine (410 mg, 1.23 mmol) in anhydrous carbon tetrachloride (5 mL) was added NBS (242 mg, 1.36 mmol) and catalytic benzoyl peroxide (59.8 mg, 0.25 mmol). The resulting mixture was stirred at reflux for 1.5 hours, then cooled and allowed to stir at 23° C. for 16 hours. The dark brown mixture was partitioned between ethyl acetate (2×75 mL) and saturated aqueous sodium bicarbonate (90 mL). The combined organic layers were dried over sodium sulfate, filtered and concentrated under reduced pressure. The residue was purified by chromatography on silica (0-40% EtOAc/hexanes) to afford 6-bromo-4-(bromomethyl)-N-(4-(trifluoromethyl)pyridin-2-yl)pyridin-2-amine. MS ESI calcd. for $C_{12}H_9Br_2F_3N_3$ [M+H]+ 411. found 411. $^1$H NMR (500 MHz, CDCl$_3$) δ 8.41 (m, 1H), 7.85 (m, 1H), 7.68 (s, 1H), 7.47 (s, 1H), 7.11 (m, 1H), 2.46 (s, 2H).

Step 2: To a flask containing sodium methoxide (85 mg, 1.58 mmol) was added a solution of (6-bromo-4-(bromomethyl)-N-[4-(trifluoromethyl)pyridin-2-yl]pyridin-2-amine (100 mg, 0.24 mmol) in methanol (5 mL). The resulting yellow solution was stirred at 75° C. for 20 hours. Additional sodium methoxide (85 mg, 1.58 mmol) and methanol (5 mL) were added and the reaction was stirred at 75° C. for 3 days. The reaction was partitioned between ethyl acetate (2×55 mL) and water (65 mL). The combined organic layers were dried over sodium sulfate, filtered and concentrated under reduced pressure. The residue was purified by chromatography on silica (0-40% EtOAc/hexanes) to afford 6-bromo-4-(methoxymethyl)-N-(4-(trifluoromethyl)pyridin-2-yl)pyridin-2-amine. MS ESI calcd. for $C_{13}H_{12}BrF_3N_3O$ [M+H]+ 362 and 364. found 362 and 364.

Preparative Example 2

Preparation of Pyridinyl Precursors

Preparative Example 2.1

2-Bromo-4-(1-(4-methoxybenzyl)-1H-1,2,3-triazol-4-yl)pyridine

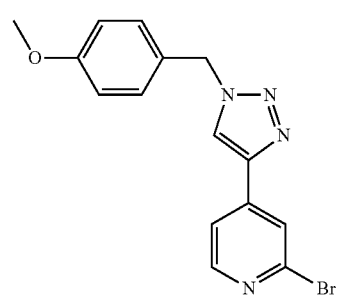

PrepEx-2.1

To a flask was added 2-bromo-4-ethynylpyridine (1 g, 5.49 mmol), 1-(azidomethyl)-4-methoxybenzene (*Chem. Eur. J.,* 2011, 17, 14727-14730) (0.90 g, 5.49 mmol), copper(II) sulfate pentahydrate (0.14 g, 0.55 mmol), sodium ascorbate (0.54 g, 2.75 mmol), water (13.7 mL) and t-BuOH (13.73 mL) and the mixture was stirred at room temperature for 16 hours. The mixture was poured into EtOAc and saturated aqueous sodium bicarbonate solution. The layers were separated, and the organic phase was washed with brine, dried over anhydrous magnesium sulfate, filtered and concentrated under reduced pressure. The residue was purified by chromatography on silica (30-70% EtOAc/hexanes) to afford 2-bromo-4-(1-(4-methoxybenzyl)-1H-1,2,3-triazol-4-yl)pyridine. MS ESI calcd. for $C_{15}H_{14}BrN_4O$ [M+H]$^+$ 345. found 345. $^1$H NMR (600 MHz, DMSO-d$_6$) δ 8.86 (s, 1H), 8.38 (d, J=5.2 Hz, 1H), 8.02 (s, 1H), 7.84 (dd, J=5.2, 1.4 Hz, 1H), 7.31 (t, J=5.8 Hz, 2H), 6.92 (dd, J=9.2, 2.5 Hz, 2H), 5.56 (s, 2H), 3.70 (s, 3H).

Preparative Example 2.2

2-Bromo-4-(2-methyl-2H-1,2,3-triazol-4-yl)pyridine and 2-Bromo-4-(1-methyl-1H-1,2,3-triazol-4-yl) pyridine

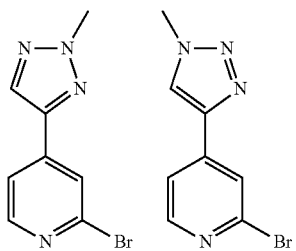

PrepEx-2.2

Step 1: To a flask was added 2-bromo-4-(1-(4-methoxybenzyl)-1H-1,2,3-triazol-4-yl)pyridine (300 mg, 0.87 mmol) and TFA (4.35 mL) and the mixture was heated to 60 OC for 6 hours. After cooling to room temperature, the mixture was concentrated under reduced pressure. The crude oil was dissolved in EtOAc and washed with saturated aqueous sodium bicarbonate and then brine, then dried over anhydrous magnesium sulfate, filtered and concentrated under reduced pressure. The residue was purified by chromatography on silica (30-60% EtOAc/hexanes) to afford 2-bromo-4-(1H-1,2,3-triazol-4-yl)pyridine. MS ESI calcd. for $C_7H_6BrN_4$ [M+H]$^+$ 225 found 225.

Step 2: To a flask was added sodium hydride (21 mg, 0.53 mmol) and the vessel was cooled to 0° C. A solution of 2-bromo-4-(1H-1,2,3-triazol-4-yl)pyridine (100 mg, 0.44 mmol) in DMF (2.2 mL) was then added dropwise. After 20 minutes, methyl iodide (28 μL, 0.44 mmol) was added, and the mixture was stirred at 0° C. for 10 minutes. The reaction was then poured into a mixture of EtOAc and pH 3 buffer, and the layers were separated. The aqueous layer was extracted with EtOAc, and then the combined organic layers were washed with saturated aqueous sodium chloride, dried over anhydrous magnesium sulfate, filtered, and concentrated under reduced pressure. The residue was purified by chromatography on silica (10-70% EtOAc/hexanes) to afford 2-bromo-4-(2-methyl-2H-1,2,3-triazol-4-yl)pyridine (Isomer 1, first eluting) MS ESI calcd. for $C_8H_8BrN_4$ [M+H]$^+$ 239 found 239. $^1$H NMR (600 MHz, DMSO-d$_6$) δ 8.48 (s, 1H), 8.42 (dd, J=5.1, 0.4 Hz, 1H), 8.03 (d, J=0.8 Hz, 1H), 7.82 (dd, J=5.1, 1.4 Hz, 1H), 4.20 (d, J=5.2 Hz, 3H) and 2-bromo-4-(1-methyl-1H-1,2,3-triazol-4-yl)pyridine (Isomer 2, second eluting). MS ESI calcd. for $C_8H_8BrN_4$ [M+H]$^+$ 239 found 239. $^1$H NMR (600 MHz, DMSO-d$_6$) δ 8.80 (s, 1H), 8.40 (d, J=5.1 Hz, 1H), 8.01 (d, J=0.8 Hz, 1H), 7.84 (dd, J=5.1, 1.4 Hz, 1H), 4.09 (s, 3H).

Preparative Example 2.3 tert-Butyl (3-((2-chloropyridin-4-yl)oxy)propyl) carbamate

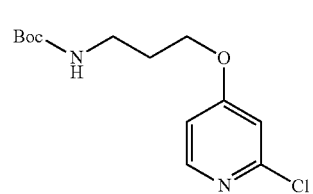

PrepEx-2.3

To a solution of tert-butyl(3-hydroxypropyl)carbamate (0.26 mL, 1.52 mmol) and 2-chloro-4-fluoropyridine (0.15 mL, 1.52 mmol) in DMF (3 mL) at 0° C. under N$_2$ was added sodium hydroxide (182 mg, 4.56 mmol) and the mixture was stirred at 0° C. for 10 minutes. The reaction mixture was quenched with saturated aqueous ammonium chloride solution, diluted with EtOAc, washed with brine, dried over anhydrous sodium sulfate, filtered and concentrated under reduced pressure. The residue was purified by column chromatography on silica gel (EtOAc/hexanes) to afford tert-butyl (3-((2-chloropyridin-4-yl)oxy)propyl)carbamate. MS ESI calcd. for $C_{13}H_{20}ClN_2O_3$ [M+H]$^+$ 287. found 287. $^1$H NMR (600 MHz, CDCl$_3$) δ 8.16 (d, J=6.0 Hz, 1H), 6.81 (d, J=2.4 Hz, 1H), 6.72 (dd, J=6.0, 2.4 Hz, 1H), 4.62 (br s, 1H), 4.05 (t, J=6.0 Hz, 2H), 3.32-3.27 (m, 2H), 2.01-1.96 (m, 2H), 1.42 (s, 9H).

Preparative Example 3

Preparation of Ketone C$^y$ Precursors

Preparative Example 3.1

Methyl 2,2-dimethyl-4-oxocyclohexanecarboxylate

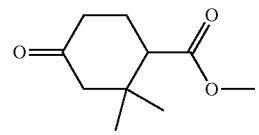

PrepEx-3.1

Step 1: Methyl 3-oxobutanoate (232 g, 2.00 mol) and paraformaldehyde (30 g, 999 mmol) were combined and piperidine (10 g, 117.44 mmol) was added. The resulting solution was stirred for 2 hours at 0° C. The solution was then heated to 60° C. for 2 hours. The mixture was extracted with Et$_2$O (3×), and the organic layers were combined and dried over anhydrous sodium sulfate, filtered, and concentrated under reduced pressure to afford dimethyl 2-methyl- 6-oxocyclohex-1-ene-1,3-dicarboxylate as a brown oil. MS ESI calcd. for $C_{11}H_{15}O_5$ [M+H]$^+$ 227. found 227.

Step 2: To a solution of sodium methanolate (90 g, 1.67 mol) in methanol (300 mL) was added dimethyl 2-methyl-6-oxocyclohex-1-ene-1,3-dicarboxylate (150 g, 663.04 mmol) in methanol (150 mL) dropwise with stirring over 30 minutes. The resulting solution was heated to 80° C. for 30 minutes, and the mixture was concentrated under reduced pressure. The reaction mixture was diluted with water/ice (120 mL), then diluted further with acetic acid (130 mL). The resulting solution was extracted with Et$_2$O (3×), and the organic layers were combined and dried over anhydrous sodium sulfate, filtered, and concentrated under reduced pressure. The residue was purified by distillation under reduced pressure (5 mm Hg), and the fraction was collected at 110-120° C. Methyl 2-methyl-4-oxocyclohex-2-enecarboxylate was obtained as a yellow oil. MS ESI calcd. for $C_9H_{13}O_3$ [M+H]$^+$ 169. found 169.

Step 3: Copper iodide (121.8 g, 639.54 mmol) was suspended in Et$_2$O (800 mL). Methyllithium (1.6 M in diethyl ether, 800 mL, 1.28 mol) was added dropwise at −40° C. over 3 hours. A solution of methyl 2-methyl-4-oxocyclohex-2-enecarboxylate (53.8 g, 319.88 mmol) in Et$_2$O (400 mL) was added at −40° C. over 2 minutes. The resulting solution was stirred for 5 hours at −20° C. The mixture was diluted with saturated aqueous ammonium chloride (2.5 L) and extracted with EtOAc (3×2 L). The combined organic extracts were dried over anhydrous sodium sulfate, filtered, and concentrated under reduced pressure. The residue was purified by silica gel column chromatography (EtOAc/petroleum ether) to afford methyl 2,2-dimethyl-4-oxocyclohexanecarboxylate as a yellow oil. MS ESI calcd. for $C_{10}H_{17}O_3$ [M+H]$^+$ 185. found 185. $^1$H NMR (600 MHz, CDCl$_3$) δ 3.49 (s, 3H), 2.43-2.40 (m, 1H), 2.35-2.29 (m, 1H), 2.21-2.17 (m, 1H), 2.11-2.04 (m, 1H), 2.00-1.96 (m, 1H), 1.91-1.85 (m, 2H), 0.85 (s, 3H), 0.77 (s, 3H).

Preparative Example 4

Preparation of Thiazole-C$^y$ Precursors

Preparative Example 4.1

Ethyl cis-4-hydroxy-4-(1,3-thiazol-2-yl)cyclohexanecarboxylate

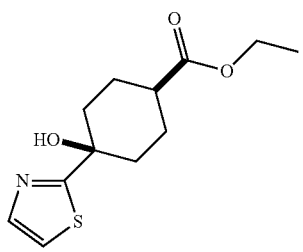

PrepEx-4.1

Thiazole (5.25 g, 61.7 mmol) was added dropwise to a flask containing i-PrMgCl.LiCl (1.3 M in THF, 47.5 mL, 61.7 mmol) at 0° C., ensuring the temperature throughout the addition did not exceed 10° C. The resulting suspension was stirred for 30 minutes and then cooled to −10° C. and ethyl 4-oxocyclohexanecarboxylate (10.0 g, 58.8 mmol) in THF (25 mL) was added dropwise and the suspension was allowed to warm to 25° C. over 2 hours. The vessel was cooled to 5° C. and then HCl (2M, 100 mL) and ethyl acetate (250 mL) were added. The aqueous layer was extracted with ethyl acetate (250 mL) and the combined organic layers washed with saturated aqueous sodium bicarbonate solution (100 mL), brine (100 mL), dried over magnesium sulfate, filtered and concentrated under reduced pressure. The residue was chromatographed on silica gel and then subjected to SFC separation (IC column, 30% acetonitrile) to afford ethyl cis-4-hydroxy-4-(1,3-thiazol-2-yl)cyclohexanecarboxylate (Isomer 2, slower eluting). $^1$H NMR (600 MHz, CDCl$_3$) δ 7.69 (d, J=3.6 Hz, 1H), 7.25 (d, J=3.6 Hz, 1H), 4.13 (q, J=7.12 Hz, 2H), 2.75 (s, 1H), 2.39 (m, 1H), 2.01-1.9 (m, 7H), 1.56 (s, 1H), 1.25 (t, J=7.12 Hz, 3H).

Preparative Example 4.2

Ethyl 2-hydroxy-2-(thiazol-2-yl)spiro[3.5]nonane-7-carboxylate

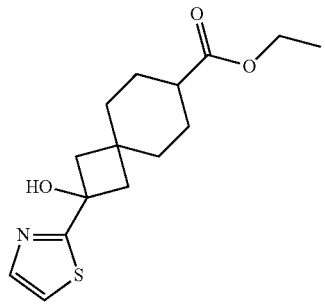

PrepEx-4.2

Step 1: To a solution of ethyl 4-methylenecyclohexanecarboxylate (2.3 g, 19 mmol) and Zn—Cu (3.6 g) in ether was added dropwise 2,2,2-trichloroacetyl chloride (4.5 mL, 39 mmol) in ether over a period of 20 minutes. The mixture was heated to 35° C. for 12 hours. Then the mixture was filtered through CELITE and washed with ether. The filtrate was concentrated under reduced pressure and the residue was purified by silica gel chromatography to afford ethyl 1,1-dichloro-2-oxospiro[3.5]nonane-7-carboxylate.

Step 2: To a solution of ethyl 1,1-dichloro-2-oxospiro[3.5]nonane-7-carboxylate (5 g, 18 mmol) in acetic acid was added Zn (5 g, 76 mmol). The mixture was stirred at 100° C. for 12 hours. Then the mixture was filtered and the filtrate was concentrated under reduced pressure. The residue was purified by silica gel chromatography to afford ethyl 2-oxospiro[3.5]nonane-7-carboxylate. $^1$H NMR (400 MHz, CD$_3$OD) δ 4.15 (s, 2H), 2.84 (s, 4H), 2.45 (s, 1H), 1.86 (s, 2H), 1.75-1.74 (m, 2H), 1.65 (d, J=7.2 Hz, 2H), 1.58 (d, J=6.8 Hz, 2H), 1.26 (s, 3H).

Step 3: To a solution of thiazole (1.1 g, 13 mmol) in THF (20 mL) was added i-PrMgCl (2 M, 7 mL) and the mixture was stirred at 0° C. under nitrogen for 1 hour. Ethyl 2-oxospiro[3.5]nonane-7-carboxylate (2.8 g, 13 mmol) in THF (20 mL) was added. The mixture was stirred at 20° C. for 2 hours. The mixture was diluted with saturated ammonium chloride solution and extracted with EtOAc. The EtOAc layer was dried over anhydrous sodium sulfate, filtered, and concentrated under reduced pressure. The residue was purified by silica gel chromatography to afford ethyl 2-hydroxy-2-(thiazol-2-yl)spiro[3.5]nonane-7-carboxylate. MS ESI calcd. for $C_{15}H_{22}NO_3S$ [M+H]$^+$ 296. found 296.

Preparative Example 4.3

Ethyl 3-hydroxy-3-(1,3-thiazol-2-yl)bicyclo[3.2.1]octane-8-carboxylate

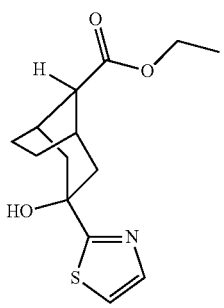

PrepEx-4.3

Step 1: To a cooled mixture of 2-(trimethylsilyoxy)-1,3-cyclohexadiene (1.82 g, 10.8 mmol) and ethyl propiolate (1.17 g, 11.88 mmol) in dichloromethane (20 mL) at 0° C. was added diethylaluminum chloride (1M in heptane, 2.2 mL, 2.2 mmol) and the mixture was maintained at 0° C. and then allowed to warm to room temperature for 2 hours. The mixture was then quenched with aqueous saturated sodium bicarbonate and then dichloromethane. The organic layer was separated, dried over magnesium sulfate, filtered, and concentrated under reduced pressure to afford ethyl 5-[(trimethylsilyl)oxy]bicyclo[2.2.2]octa-2,5-diene-2-carboxylate that was used without further purification.

Step 2: To a mixture of crude ethyl 5-[(trimethylsilyl)oxy]bicyclo[2.2.2]octa-2,5-diene-2-carboxylate (1.82 g, 6.83 mmol) in tetrahydrofuran (25 mL) was added acetic acid (0.43 mL, 7.51 mmol) and TBAF (1M in THF, 7.51 mL, 7.51 mmol) and the solution was maintained at room temperature for 15 minutes. The mixture was quenched with aqueous saturated sodium bicarbonate and extracted twice with diethyl ether. The combined organic layers were dried over magnesium sulfate, filtered, and concentrated under reduced pressure. The crude product was purified by silica gel chromatography to afford ethyl 5-oxobicyclo[2.2.2]oct-2-ene-2-carboxylate. $^1$H NMR (500 MHz, CDCl$_3$): δ 7.18 (d, J=6.8 Hz, 1H); 4.21-4.22 (m, 2H); 3.59 (s, 1H); 3.33 (dd, J=6.5, 3.0 Hz, 1H); 2.03-2.06 (m, 2H); 1.91-1.96 (m, 1H); 1.75-1.79 (m, 1H); 1.60-1.64 (m, 1H); 1.52-1.57 (m, 1H); 1.29-1.31 (m, 3H).

Step 3: A mixture of ethyl 5-oxobicyclo[2.2.2]oct-2-ene-2-carboxylate (3.32 g, 17.09 mmol) in acetone (230 mL) at 11° C. was irradiated with a photochemical lamp for 4 hours. The mixture was concentrated under reduced pressure and the resulting oil was purified by silica gel chromatography to afford ethyl 2-oxohexahydrocyclopropa[cd]pentalene-4b(1H)-carboxylate.

Step 4: To a mixture of ethyl 2-oxohexahydrocyclopropa[cd]pentalene-4b(1H)-carboxylate (260 mg, 1.34 mmol) in benzene (13 mL) was added tributyltin hydride (0.90 mL, 3.35 mmol) and 2,2'-azobis(2-methylpropionitrile) (66 mg, 0.40 mmol) and the mixture was degassed with argon and then heated to 80 OC for 16 h. The mixture was allowed to cool to room temperature and then concentrated in vacuo. The crude product was purified by silica gel chromatography to afford ethyl 3-oxobicyclo[3.2.1]octane-8-carboxylate. $^1$H NMR (500 MHz, CDCl$_3$): δ 4.22 (q, J=7.1 Hz, 2H), 2.80 (s, 1H), 2.74-2.78 (m, 4H), 2.26 (s, 1H), 2.22 (s, 1H), 1.86-1.89 (m, 2H), 1.58-1.59 (m, 2H), 1.29 (t, J=7.1 Hz, 3H).

Step 5: To a mixture of thiazole (500 mg, 5.87 mmol) in THF (59 mL) at −78° C. was added n-butyllithium (1.6 M in hexanes, 5.5 mL, 8.8 mmol) and the mixture was stirred for 30 minutes. A solution of ethyl 3-oxobicyclo[3.2.1]octane-8-carboxylate (1.38 g, 7.05 mmol) in THF (5 mL) was added in one portion and the mixture was stirred for 1 hour at −78° C. The reaction was quenched with water and then allowed to warm to room temperature. The mixture was diluted with water and ethyl acetate and the organic layer was separated, dried over magnesium sulfate, filtered and concentrated. The crude product was purified by silica gel chromatography (0-35% ethyl acetate gradient in hexanes) to afford ethyl 3-hydroxy-3-(1,3-thiazol-2-yl)bicyclo[3.2.1]octane-8-carboxylate. MS ESI calcd. for $C_{14}H_{20}NO_3S$ [M+H]$^+$ 282. found 282. $^1$H NMR (500 MHz, DMSO-d6): δ 7.63 (d, J=3.2 Hz, 1H); 7.47 (d, J=3.2 Hz, 1H); 5.78 (s, 1H); 4.12 (q, J=7.1 Hz, 2H); 2.38-2.41 (m, 5H); 2.07-2.08 (m, 2H); 1.68-1.71 (m, 2H); 1.63-1.66 (m, 2H); 1.19 (t, J=7.1 Hz, 3H).

Preparative Example 5

Preparation of Thiazole-C$^y$ Pyridylamine Precursors

Preparative Example 5.1

Ethyl cis-4-[5-(6-amino-4-methylpyridin-2-yl)thiazol-2-yl]-4-hydroxycyclohexanecarboxylate

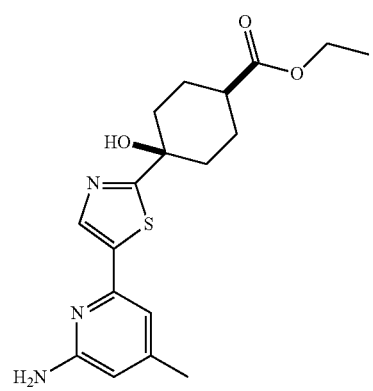

PrepEx-5.1

Step 1: Para-methoxy benzyl chloride (3.5 g, 22.5 mmol) was slowly added to a suspension of 6-bromo-4-methylpyridin-2-amine (2.0 g, 10.7 mmol) and potassium tert-butoxide (2.76 g, 22.3 mmol) in dimethyl acetamide (16 mL). After stirring for 12 hours, water (10 mL) was added and then the mixture extracted with ethyl acetate (2×200 mL) and dried over magnesium sulfate, and concentrated under reduced pressure. The residue was chromatographed on silica gel to afford 6-bromo-N,N-bis(4-methoxybenzyl)-4-methylpyridin-2-amine. MS ESI calcd. for $C_{22}H_{24}BrN_2O_2$ [M+H]$^+$ 428. found 428.

Step 2: Into a flask was added butyl diadamantyl phosphine (1.1 g, 3.1 mmol) and allyl palladium chloride dimer (0.287 g, 0.78 mmol) followed by nitrogen sparged dimethyl acetamide (16 mL). After 10 minutes of stirring, potassium carbonate (3.2 g, 23.5 mmol), pivalic acid (1.2 g, 11.8 mmol), ethyl cis-4-hydroxy-4-(thiazol-2-yl)cyclohexanecarboxylate (2.0 g, 7.83 mmol) and 6-bromo-N,N-bis(4-methoxybenzyl)-4-methylpyridin-2-amine (3.3 g, 7.80 mmol). The slurry was evacuated and refilled with nitrogen three times and then heated at 100° C. for 6 hours. The slurry was cooled to 35° C. and diluted with ethyl acetate (100 mL). The organic layer was then washed with brine (3×100 mL) and concentrated under reduced pressure. The residue was chromatographed on silica gel to afford ethyl cis-4-(5-(6-(bis(4-methoxybenzyl)amino)-4-methylpyridin-2-yl)thiazol-2-yl)-4-hydroxycyclohexanecarboxylate. $^1$H NMR (600 MHz, CDCl$_3$) δ 8.02 (s, 1H), 7.16 (d, J=9.0 Hz, 4H), 6.82 (d, J=9.0 Hz, 4H), 6.78 (s, 1H), 6.18 (s, 1H), 4.67 (s, 4H), 4.12 (q, J=7.2 Hz, 2H), 3.76 (s, 6H), 2.29 (s, 1H), 2.37 (m, 1H), 2.19 (s, 3H), 2.0-1.93 (m, 8H), 1.23 (t, J=4.9 Hz, 3H).

Step 3: Ethyl cis-4-(5-(6-(bis(4-methoxybenzyl)amino)-4-methylpyridin-2-yl)thiazol-2-yl)-4-hydroxycyclohexanecarboxylate (0.75 g, 1.2 mmol) in toluene (0.7 mL) was treated with TFA (1.4 g, 12.5 mmol) and heated to 40° C. for 2 hours. After cooling to room temperature, the solution was concentrated under reduced pressure. The residue was treated with 9:1 (dichloromethane:methanol) and then washed with saturated aqueous sodium bicarbonate solution (20 mL), and concentrated under reduced pressure. The residue was chromatographed on silica gel to afford ethyl cis-4-(5-(6-amino-4-methyalpyridin-2-yl)thiazol-2-yl)-4-hydroxycyclohexanecarboxylate. MS ESI calcd. for $C_{18}H_{24}N_3O_3S$ [M+H]$^+$ 362. found 362. $^1$H NMR (600 MHz, CDCl$_3$) δ 7.90 (s, 1H), 6.71 (s, 1H), 6.14 (s, 1H), 4.64 (s, 2H), 4.12 (s, 1H), 4.06 (d, J=6.6 Hz, 2H), 2.30 (m, 1H), 2.15 (s, 3H), 1.93-1.82 (m, 8H), 1.18 (t, J=7.8 Hz, 3H).

Preparative Example 5.2

Methyl (1R,4S or 1S,4R)-4-[5-(6-bromopyridin-2-yl)-1,3-thiazol-2-yl]-4-hydroxy-2,2-dimethylcyclohexanecarboxylate (Isomer 1) and Methyl (1R,4S or 1S,4R)-4-[5-(6-bromopyridin-2-yl)-1,3-thiazol-2-yl]-4-hydroxy-2,2-dimethylcyclohexanecarboxylate (Isomer 2)

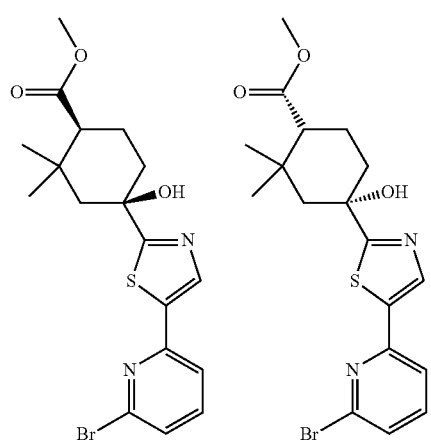

PrepEx-5.2

Step 1: A screw-cap high-pressure vial containing a suspension of 2,6-dibromopyridine (11.13 g, 47.0 mmol), pivalic acid (0.55 mL, 4.70 mmol), and potassium carbonate (6.49 g, 47.0 mmol) in N,N-dimethylacetamide (45 mL) was sparged with argon for 20 minutes. Thiazole (1.68 mL, 23.49 mmol) and tetrakis(triphenylphosphine)palladium(0) (1.09 g, 0.94 mmol) were added, the vial was sealed, and the reaction mixture was heated at 115° C. for 18 hours. The reaction mixture was diluted with water (50 mL), ethyl acetate (50 mL), and diethyl ether (50 mL) and the layers were separated. The organic layer was washed with water (2×50 mL), saturated aqueous sodium bicarbonate (25 mL), and brine (50 mL), dried over anhydrous sodium sulfate, filtered, and concentrated under reduced pressure. The residue was purified by chromatography on silica gel (10-60% ethyl acetate/hexanes) to afford 5-(6-bromopyridin-2-yl)thiazole. MS ESI calcd. for $C_8H_6BrN_2S$ [M+H]$^+$ 241 and 243. found 241 and 243. $^1$H NMR (500 MHz, DMSO-d6) δ 9.19 (s, 1H), 8.63 (s, 1H), 8.04 (d, J=7.6 Hz, 1H), 7.83 (t, J=7.9 Hz, 1H), 7.58 (d, J=7.8 Hz, 1H).

Step 2: To a solution of 5-(6-bromopyridin-2-yl)thiazole (2.43 g, 10.08 mmol) in THF (100 mL) was added lithium diisopropyl amide (1.8 M in THF/heptane/ethylbenzene, 5.9 mL, 10.6 mmol) over 5 min at −78° C. After 35 minutes, a solution of methyl 2,2-dimethyl-4-oxocyclohexanecarboxylate (1.95 g, 10.58 mmol) in THF (7 mL) was added in one portion. After 75 minutes, saturated aqueous ammonium chloride (10 mL) was added and the reaction mixture was warmed to room temperature and diluted with ethyl acetate (150 mL), water (4 mL), and saturated aqueous ammonium chloride (10 mL). The layers were separated and the organic layer was washed with saturated aqueous sodium bicarbonate and brine, dried over sodium sulfate, filtered, and concentrated under reduced pressure. The residue was purified by chromatography on silica gel (5-25% ethyl acetate/dichloromethane) to afford methyl 4-[5-(6-bromopyridin-2-yl)-1,3-thiazol-2-yl]-4-hydroxy-2,2-dimethylcyclohexanecarboxylate. The racemic material was purified by chiral SFC (40%/60% ethanol/CO$_2$) to afford methyl (1R,4S or 1S,4R)-4-[5-(6-bromopyridin-2-yl)-1,3-thiazol-2-yl]-4-hydroxy-2,2-dimethylcyclohexanecarboxylate (Isomer 1, first eluting): $^1$H NMR (500 MHz, DMSO$_{d-6}$) δ 8.35 (s, 1H), 7.95 (d, J=7.9 Hz, 1H), 7.79 (t, J=7.8 Hz, 1H), 7.54 (d, J=7.8 Hz, 1H), 5.96 (s, 1H), 3.59 (s, 3H), 2.29 (dd, J=12.8, 2.9 Hz, 1H), 2.06 (m, 1H), 1.90-1.80 (m, 3H), 1.63 (d, J=13.4 Hz, 1H), 1.58 (dd, J=13.6, 3.1 Hz, 1H), 1.08 (s, 3H), 0.96 (s, 3H).) and methyl (1R,4S or 1S,4R)-4-[5-(6-bromopyridin-2-yl)-1,3-thiazol-2-yl]-4-hydroxy-2,2-dimethylcyclohexanecarboxylate (Isomer 2, second eluting): $^1$H NMR (500 MHz, DMSO$_{d-6}$) δ 8.35 (s, 1H), 7.95 (d, J=7.6 Hz, 1H), 7.79 (t, J=8.0 Hz, 1H), 7.54 (d, J=7.8 Hz, 1H), 5.96 (s, 1H), 3.59 (s, 3H), 2.30 (dd, J=12.7, 3.0 Hz, 1H), 2.06 (m, 1H), 1.90-1.80 (m, 3H), 1.61 (d, J=13.0 Hz, 1H), 1.59 (dd, J=13.6, 3.0 Hz, 1H), 1.08 (s, 3H), 0.96 (s, 3H).

The intermediates in the following table were prepared according to the method described for Preparative Example 5.2.

| Prep. Ex. | Structure | Chemical Name | Exact Mass [M + H]+ | [M + H]+ Obsv'd |
|---|---|---|---|---|
| 5.3 | 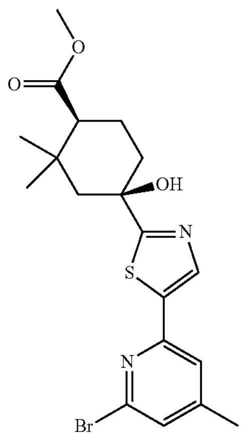 [SMILES: COC(=O)[C@H]1CC[C@](O)(c2ncc(-c3cc(C)cc(Br)n3)s2)CC1(C)C] | methyl (1R,4S or 1S,4R)-4-(5-(6-bromo-4-methylpyridin-2-yl)thiazol-2-yl)-4-hydroxy-2,2-dimethylcyclohexanecarboxylate | 439 and 441 | 439 and 441 |

Preparative Example 6

Preparation of Bispyridylamine Thiazole Precursors

Preparative Example 6.1

4-Methyl-6-(1,3-thiazol-5-yl)-N-[4-(trifluoromethyl)pyridin-2-yl]pyridin-2-amine

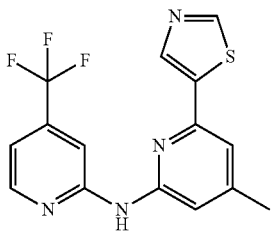

PrepEx-6.1

To a flask containing 6-bromo-4-methyl-N-[4-(trifluoromethyl)pyridin-2-yl]pyridin-2-amine (1.50 g, 4.52 mmol), 5-(4,4,5,5-tetramethyl-1,3,2-dioxaborolan-2-yl)-1,3-thiazole (1.90 g, 9.03 mmol) potassium carbonate (1.87 g, 13.55 mmol) and 1,1'-bis(diphenylphosphino)ferrocenedichloro palladium(II) dichloromethane complex (165 mg, 0.226 mmol) was added previously degassed DMF (9 mL). The flask was evacuated/purged with argon 5 times and then heated to 80 OC for 16 hours. The mixture was allowed to cool to room temperature, diluted with ethyl acetate and water and the organic layer was separated, dried over magnesium sulfate, filtered and concentrated. The crude product was purified by silica gel chromatography to afford 4-methyl-6-(1,3-thiazol-5-yl)-N-[4-(trifluoromethyl)pyridin-2-yl]pyridin-2-amine. MS ESI calcd. for $C_{15}H_{12}F_3N_4S$ [M+H]+ 337. found 337. $^1$H NMR (500 MHz, DMSO-d$_6$) δ 10.23 (s, 1H), 9.16 (s, 1H), 8.61 (s, 1H), 8.53 (s, 1H), 8.48 (d, J=5.0 Hz, 1H), 7.45 (s, 1H), 7.21 (d, J=5.0 Hz, 1H), 7.12 (s, 1H), 2.32 (s, 3H).

Preparative Example 6.2

N-(4-cyclopropylpyridin-2-yl)-4-methyl-6-(thiazol-5-yl)pyridin-2-amine

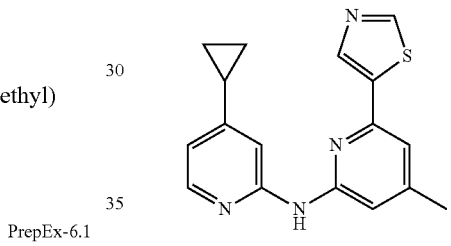

PrepEx-6.2

A flask containing 6-bromo-N-(4-cyclopropylpyridin-2-yl)-4-methylpyridin-2-amine (300 mg, 0.99 mmol) and 5-(tributylstannyl)thiazole (369 mg, 0.99 mmol) was purged with argon (3×). Palladium tetrakis (29 mg, 0.03 mmol) was added followed by toluene (3 mL) and the reaction mixture was heated to 110° C. for 18 hours. The reaction mixture was diluted with chloroform and washed with brine. The organic layer was dried over sodium sulfate and concentrated under reduced pressure. The residue was purified by silica gel chromatography to afford N-(4-cyclopropylpyridin-2-yl)-4-methyl-6-(thiazol-5-yl)pyridin-2-amine as a white solid. MS ESI calcd. for $C_{17}H_{17}N_4S$ [M+H]+ 309. found 309. $^1$H NMR (500 MHz, DMSO-d6) δ 9.56 (s, 1H), 9.13 (s, 1H), 8.51 (s, 1H), 8.04 (d, J=5.5 Hz, 1H), 7.81 (s, 1H), 7.35 (s, 1H), 7.19 (s, 1H), 6.63 (d, J=5.5 Hz, 1H), 2.29 (s, 3H), 1.95-1.85 (m, 1H), 1.09-1.05 (m, 2H), 0.90-0.80 (m, 2H).

Preparative Example 6.3

6-(Thiazol-5-yl)-N²-(4-(trifluoromethyl)pyridin-2-yl)pyridine-2,4-diamine

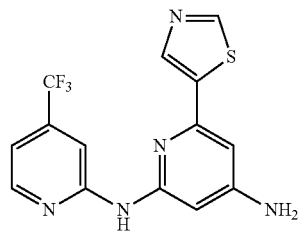

PrepEx-6.3

Step 1: A flask was charged with 2,6-dibromo-4-nitropyridine (869 mg, 3.08 mmol), 4-(trifluoromethyl)pyridin-2-amine (500 mg, 3.08 mmol), xantphos (535 mg, 0.93 mmol), cesium carbonate (2.0 g, 6.2 mmol), palladium(II) acetate (138 mg, 0.62 mmol) and dioxane (20 mL). The vial was sealed and placed under an argon atmosphere then stirred at 110° C. for one hour. The reaction mixture was cooled to room temperature and diluted with EtOAc. The resulting mixture was washed with saturated sodium bicarbonate then brine. The organic layer was dried over anhydrous sodium sulfate, filtered and concentrated under reduced pressure. The residue was purified by column chromatography on silica (3-25% EtOAc/hexanes) to afford 6-bromo-4-nitro-N-(4-(trifluoromethyl)pyridin-2-yl)pyridin-2-amine as a yellow solid. MS ESI calcd. for $C_{11}H_6BrF_3N_4O_2$ [M+H]$^+$ 363 and 365. found 363 and 365.

Step 2: 6-Bromo-4-nitro-N-(4-(trifluoromethyl)pyridin-2-yl)pyridin-2-amine (100 mg, 0.28 mmol), ammonium hydroxide (1.5 mL, 10.8 mmol) and dioxane (1.5 mL) were combined and then stirred at 100° C. for 35 minutes. The reaction mixture was cooled to room temperature and diluted with EtOAc. The resulting mixture was washed with saturated sodium bicarbonate, then brine. The organic layer was dried over anhydrous sodium sulfate, filtered and concentrated under reduced pressure. To remove residual ammonium hydroxide the residue was once again diluted with EtOAc, washed with saturated sodium bicarbonate, then brine, dried over anhydrous sodium sulfate, filtered and concentrated under reduced pressure to afford 6-bromo-$N^2$-(4-(trifluoromethyl)pyridin-2-yl)pyridine-2,4-diamine as a yellow solid. MS ESI calcd. for $C_1H_9BrF_3N_4$ [M+H]$^+$ 333 and 335. found 333 and 335.

Step 3: 6-Bromo-$N^2$-(4-(trifluoromethyl)pyridin-2-yl)pyridine-2,4-diamine (190 mg, 0.57 mmol), 5-(tributylstannyl)thiazole (213 mg, 0.57 mmol), Pd(Ph$_3$P)$_4$ (8 mg, 6.9 mol) and toluene (2.3 mL) were combined, placed under an argon atmosphere and then stirred at 100° C. for 3 days. The reaction mixture was cooled to room temperature and diluted with EtOAc. The resulting mixture was washed with saturated sodium bicarbonate and then brine. The organic layer was dried over anhydrous sodium sulfate, filtered and concentrated under reduced pressure. The residue was purified by column chromatography on silica (10-100% EtOAc/hexanes) to afford 6-(thiazol-5-yl)-$N^2$-(4-(trifluoromethyl)pyridin-2-yl)pyridine-2,4-diamine. MS ESI calcd. for $C_{14}H_1F_3N_5S$ [M+H]$^+$ 338. found 338. $^1$H NMR (500 MHz, DMSO-d$^6$) δ 9.86 (s, 1H), 9.10 (s, 1H), 8.61 (s, 1H), 8.42 (d, J=5.2 Hz, 1H), 8.28 (s, 1H), 7.12 (d, J=5.2 Hz, 1H), 6.70 (s, 1H), 6.44 (s, 1H), 6.17 (s, 2H).

Preparative Example 6.4

N-(2-(thiazol-5-yl)-6-((4-(trifluoromethyl)pyridin-2-yl)amino)pyridin-4-yl)acetamide

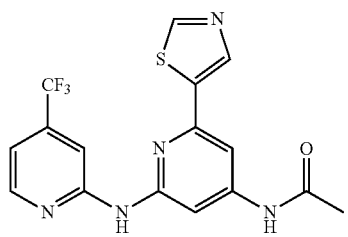

PrepEx-6.4

Step 1: 4-(Trifluoromethyl)pyridin-2-amine (243 mg, 1.50 mmol), N-(2,6-dibromopyridin-4-yl)acetamide (400 mg, 1.36 mmol), xantphos (118 mg, 0.20 mmol), cesium carbonate (887 mg, 2.7 mmol), palladium(II) acetate (118 mg, 0.20 mmol) and dioxane (3 mL) were combined, placed under an argon atmosphere and then stirred at 100° C. for 3 hours. The reaction mixture was diluted with DCM, filtered through CELITE, and the filtrate was concentrated under reduced pressure. The residue was purified by column chromatography on silica (0-100% EtOAc/hexanes) to afford N-(2-bromo-6-((4-(trifluoromethyl)pyridin-2-yl)amino)pyridin-4-yl)acetamide as white solid. MS ESI calcd. for $C_{13}H_{11}BrF_3N_4O$ [M+H]$^+$ 375. found 375.

Step 2: N-(2-bromo-6-((4-(trifluoromethyl)pyridin-2-yl)amino)pyridin-4-yl)acetamide (100 mg, 0.27 mmol), thiazole (0.1 mL, 1.33 mmol), palladium(II) acetate (12 mg, 0.05 mmol), cataCXium (38 mg, 0.11 mmol), cesium fluoride (121 mg, 0.80 mmol), pivalic acid (41 mg, 0.40 mmol) and dioxane (1 mL) were combined, placed under an argon atmosphere and then stirred at 100° C. for overnight. The reaction mixture was diluted with DCM, filtered through CELITE, and the filtrate was concentrated under reduced pressure. The residue was purified by column chromatography on silica (0-100% EtOAc/hexanes) to afford N-(2-(thiazol-5-yl)-6-((4-(trifluoromethyl)pyridin-2-yl)amino)pyridin-4-yl)acetamide as a white solid. MS ESI calcd. for $C_{16}H_{13}F_3N_5OS$ [M+H]$^+$ 380. found 380. $^1$H NMR (600 MHz, DMSO-d$^6$) δ 10.39 (s, 1H), 10.27 (s, 1H), 9.15 (s, 1H), 8.54 (s, 1H), 8.45 (d, J=5.1 Hz, 1H), 8.31 (s, 1H), 7.63 (s, 1H), 7.59 (s, 1H), 7.19 (d, J=4.3 Hz, 1H), 2.07 (s, 3H).

Example 1

Preparation of Compounds of Formula (I) Using the Methods Illustrated in Scheme 2

Example 1.1

(1S,4R or 1R,4S)-4-(5-(6-((4-Cyclopropylpyridin-2-yl)amino)-4-methylpyridin-2-yl)thiazol-2-yl)-4-hydroxy-2,2-dimethylcyclohexanecarboxylic acid

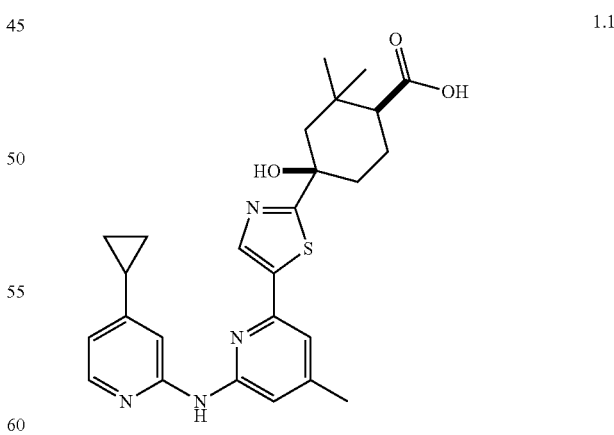

1.1

Step 1: A flask containing THF (1.0 ml) was cooled to −78° C. LDA (0.79 mL, 1.42 mmol) was added and allowed to equilibrate to −78° C. N-(4-cyclopropylpyridin-2-yl)-4-methyl-6-(thiazol-5-yl)pyridin-2-amine (125 mg, 0.41 mmol) was dissolved in THF (0.5 mL) and added to the flask and allowed to stir for 30 minutes at −78° C. Methyl 2,2-dimethyl-4-oxocyclohexanecarboxylate (112 mg, 0.61 mmol) was dissolved in THF (0.5 mL) and added dropwise to the flask. The reaction was stirred for 1 hour, allowing it to warm to room temperature. The mixture was then quenched with aqueous ammonium chloride and diluted with ethyl acetate. The organic layer was separated, dried over magnesium sulfate, filtered and concentrated. The residue was purified by silica gel chromatography (10-100% EtOAc in hexanes, linear gradient) to afford methyl 4-(5-(6-((4-cyclopropylpyridin-2-yl)amino)-4-methylpyridin-2-yl)thiazol-2-yl)-4-hydroxy-2,2-dimethylcyclohexanecarboxylate. The racemic compound, thus obtained, was resolved by chiral super critical fluid chromatography (IC column, 1:2 methanol/$CO_2$) to afford methyl (1R,4S or 1S,4R)-4-(5-(6-((4-cyclopropylpyridin-2-yl)amino)-4-methylpyridin-2-yl)thiazol-2-yl)-4-hydroxy-2,2-dimethyl-cyclohexanecarboxylate (Isomer 1, early eluting enantiomer): MS ESI calcd. for $C_{27}H_{33}N_4O_3S$ $[M+H]^+$ 493. found 493. $^1$H NMR (500 MHz, $CD_3OD$) δ 8.17 (s, 1H), 8.05-7.90 (m, 2H), 7.20 (s, 1H), 6.98 (s, 1H), 6.65 (s, 1H), 3.68 (s, 3H), 2.40 (d, J=13.0, 1H), 2.35 (s, 3H), 2.30-2.20 (m, 1H), 2.03 (d, J=14.0, 1H), 1.99 (br s, 3H), 1.80 (d, J=14.0, 1H), 1.70 (d, J=13.5, 1H), 1.19 (s, 3H), 1.15 (d, J=7.0, 2H), 1.06 (s, 3H), 0.932 (s, 2H) and methyl (1S,4R or 1R,4S)-4-(5-(6-((4-cyclopropylpyridin-2-yl)amino)-4-methylpyridin-2-yl)thiazol-2-yl)-4-hydroxy-2,2-dimethyl-cyclohexanecarboxylate (Isomer 2, late eluting enantiomer), MS ESI calcd. for $C_{27}H_{33}N_4O_3S$ $[M+H]^+$ 493. found 493. $^1$H NMR (500 MHz, $CD_3OD$) δ 8.17 (s, 1H), 8.05-7.90 (m, 2H), 7.20 (s, 1H), 6.98 (s, 1H), 6.65 (s, 1H), 3.68 (s, 3H), 2.40 (d, J=13.0 Hz, 1H), 2.35 (s, 3H), 2.30-2.20 (m, 1H), 2.03 (d, J=14.0 Hz, 1H), 1.99 (br s, 3H), 1.80 (d, J=14.5 Hz, 1H), 1.70 (d, J=11.5 Hz, 1H), 1.19 (s, 3H), 1.15 (d, J=7.5 Hz, 2H), 1.06 (s, 3H), 0.932 (s, 2H).

Step 2: To a flask containing methyl (1S,4R or 1R,4S)-4-(5-(6-((4-cyclopropylpyridin-2-yl)amino)-4-methylpyridin-2-yl)thiazol-2-yl)-4-hydroxy-2,2-dimethylcyclohexanecarboxylate (Isomer 2, late eluting enantiomer), (60 mg, 0.12 mmol) was added THF (0.5 mL) and methanol (0.5 mL). Lithium hydroxide (1.0 M in water, 0.24 mL, 0.61 mmol) was added and the reaction mixture was heated for 45 minutes at 110 OC in the microwave. Aqueous HCl (2N) was added dropwise until the reaction mixture was an acidic pH. The reaction mixture was filtered and the filtrate was purified by reverse phase HPLC (ACN/water with 0.1% TFA modifier) to afford (1S,4R or 1R,4S)-4-(5-(6-((4-Cyclopropylpyridin-2-yl)amino)-4-methylpyridin-2-yl)thiazol-2-yl)-4-hydroxy-2,2-dimethylcyclohexanecarboxylic acid. MS ESI calcd. for $C_{26}H_{31}N_4O_3S$ $[M+H]^+$ 479. found 479. $^1$H NMR (500 MHz, $CD_3OD$) δ 8.33 (s, 1H), 8.24 (d, J=6.0 Hz, 1H), 7.57 (s, 1H), 7.07 (s, 1H), 7.03 (d, J=6.0 Hz, 1H), 6.88 (s, 1H), 2.47 (s, 3H), 2.39-2.31 (m, 1H), 2.28-2.16 (m, 2H), 2.08-1.94 (m, 3H), 1.80-1.70 (m, 2H), 1.38 (d, J=8.5 Hz, 2H), 1.24 (s, 3H), 1.12 (s, 3H), 1.09 (s, 2H).

The examples in the following table were prepared in an analogous manner to that described for Example 1.1, step 1, and where appropriate, step 2 as well.

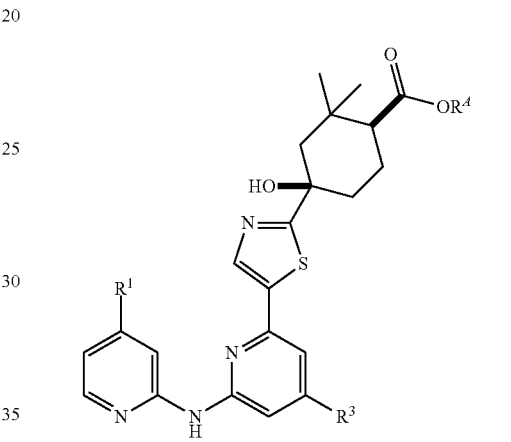

Illustration above shows relative stereochemistry.

| Ex. No. | $R^1$ | $R^3$ | $R^4$ | Chemical Name | $[M + H]^+$ Calc'd | $[M + H]^+$ Obsv'd | Form(s) |
|---|---|---|---|---|---|---|---|
| 1.2 | cyclopropyl | —$CH_3$ | —H | (1R,4S or 1S,4R)-4-(5-{6-[(4-cyclopropylpyridin-2-yl)amino]-4-methylpyridin-2-yl}-1,3-thiazol-2-yl)-4-hydroxy-2,2-dimethylcyclohexanecarboxylic acid | 479 | 479 | Chloride Salt |
| 1.3 | cyclopropyl | —$CH_3$ | —$CH_3$ | methyl (1R,4S or 1S,4R)-4-(5-{6-[(4-cyclopropylpyridin-2-yl)amino]-4-methylpyridin-2-yl}-1,3-thiazol-2-yl)-4-hydroxy-2,2-dimethylcyclohexanecarboxylate | 493 | 493 | Free Base |
| 1.4 | —$CF_3$ | —$CH_3$ | —H | 4-hydroxy-2,2-dimethyl-4-[5-(4-methyl-6-{[4-(trifluoromethyl)pyridin-2-yl]amino}pyridin-2-yl)-1,3-thiazol-2-yl]cyclohexanecarboxylic acid (racemic) | 507 | 507 | Free Base |
| 1.5 | —$CF_3$ | —$NH_2$ | —H | (1R,4S or 1S,4R)-4-[5-(4-amino-6-{[4-(trifluoromethyl)pyridin-2-yl]amino}pyridin-2-yl)-1,3-thiazol-2-yl]-4-hydroxy-2,2-dimethylcyclohexanecarboxylic acid | 508 | 508 | Free Base |
| 1.6 | —$CF_3$ | —$NH_2$ | —H | (1R,4S or 1S,4R)-4-[5-(4-amino-6-{[4- | 508 | 508 | Free Base |

| Ex. No. | R[1] | R[3] | R[4] | Chemical Name | [M + H]+ Calc'd | [M + H]+ Obsv'd | Form(s) |
|---|---|---|---|---|---|---|---|
| | | | | (trifluoromethyl)pyridin-2-yl]amino}pyridin-2-yl)-1,3-thiazol-2-yl]-4-hydroxy-2,2-dimethylcyclohexanecarboxylic acid | | | |
| 1.7 | —CF$_3$ | ⸺NH(C=O)CH$_3$ | —CH$_3$ | methyl 4-{5-[4-(acetylamino)-6-{[4-(trifluoromethyl)pyridin-2-yl]amino}pyridin-2-yl]-1,3-thiazol-2-yl}-4-hydroxy-2,2-dimethylcyclohexanecarboxylate (racemic) | 564 | 564 | Free Base |
| 1.8 | —CF$_3$ | —NH$_2$ | —H | 4-[5-(4-amino-6-{[4-(trifluoromethyl)pyridin-2-yl]amino}pyridin-2-yl)-1,3-thiazol-2-yl]-4-hydroxy-2,2-dimethylcyclohexanecarboxylic acid (racemic) | 508 | 508 | TFA Salt |
| 1.9 | —CF$_3$ | —NH$_2$ | —CH$_3$ | methyl 4-[5-(4-amino-6-{[4-(trifluoromethyl)pyridin-2-yl]amino}pyridin-2-yl)-1,3-thiazol-2-yl]-4-hydroxy-2,2-dimethylcyclohexanecarboxylate (racemic) | 522 | 522 | Free Base |

Example 2

Preparation of Compounds of Formula (I) Using the Methods Illustrated in Scheme 1

Example 2.1

Cis-4-(5-(6-((4-(1H-1,2,3-triazol-4-yl)pyridin-2-yl)amino)-4-methylpyridin-2-yl)thiazol-2-yl)-4-hydroxycyclohexanecarboxylic acid

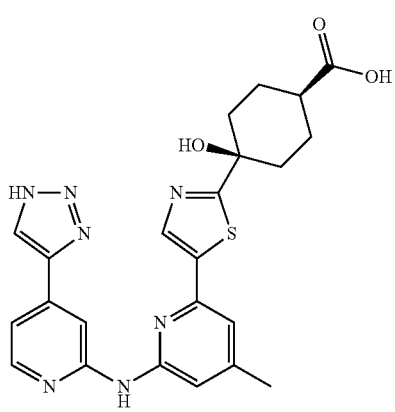

2.1

Step 1: To a microwave vial was added 2-bromo-4-(1-(4-methoxybenzyl)-1H-1,2,3-triazol-4-yl)pyridine (191 mg, 0.55 mmol), ethyl cis-4-(5-(6-amino-4-methylpyridin-2-yl)thiazol-2-yl)-4-hydroxycyclohexanecarboxylate (200 mg, 0.55 mmol), Pd(OAc)$_2$ (12.42 mg, 0.06 mmol), Xantphos (48.0 mg, 0.08 mmol), and cesium carbonate (361 mg, 1.11 mmol), and the reaction was vacuum purged 3× with argon. Degassed 1,4-dioxane (2.2 mL) was added, and then the reaction was heated to 100° C. for 30 minutes. After cooling to room temperature, the reaction was diluted with EtOAc, filtered through CELITE, and the filtrate was concentrated under reduced pressure. The residue was dissolved in DMSO (6 mL), MeOH (2 mL), and TFA (0.2 mL), and filtered, then purified by reverse phase HPLC using a gradient solvent system of 10-100% MeCN/water modified with 0.1% TFA. The product containing fractions were collected and poured into a mixture of EtOAc and saturated aqueous sodium bicarbonate. The layers were separated, and the organic phase was washed with saturated aqueous sodium chloride, dried over anhydrous magnesium sulfate, filtered and concentrated under reduced pressure to afford ethyl cis-4-hydroxy-4-(5-(6-((4-(1-(4-methoxybenzyl)-1H-1,2,3-triazol-4-yl)pyridin-2-yl)amino)-4-methylpyridin-2-yl)thiazol-2-yl)cyclohexanecarboxylate. MS ESI calcd. for C$_{33}$H$_{36}$N$_7$O$_4$S [M+H]+ 626 found 626.

Step 2: To a flask containing ethyl cis-4-(5-(6-((4-(1H-1,2,3-triazol-4-yl)pyridin-2-yl)amino)-4-methylpyridin-2-yl)thiazol-2-yl)-4-hydroxycyclohexanecarboxylate (200 mg, 0.32 mmol) was added THF (1.5 mL), MeOH (145 L) and KOH (40% in water, 136 µL, 1.28 mmol) and the mixture was heated to 50° C. for 2 hours. After cooling to room temperature, the thick slurry was acidified with TFA until the pH was 4. Water (10 mL) was added, and the mixture was stirred vigorously. The product was isolated by filtration, and the wet cake was washed with water and dried under reduced pressure to afford cis-4-hydroxy-4-(5-(6-((4-(1-(4-methoxybenzyl)-1H-1,2,3-triazol-4-yl)pyridin-2-yl)amino)-4-methylpyridin-2-yl)thiazol-2-yl)cyclohexanecarboxylic acid. MS ESI calcd. for C$_{31}$H$_{32}$N$_7$O$_4$S [M+H]+ 598 found 598.

Step 3: To microwave vial was added cis-4-hydroxy-4-(5-(6-((4-(1-(4-methoxybenzyl)-1H-1,2,3-triazol-4-yl)pyridin-2-yl)amino)-4-methylpyridin-2-yl)thiazol-2-yl)cyclohexanecarboxylic acid (35 mg, 0.06 mmol) and TFA (1 mL) and the reaction was sealed and heated to 60 OC for 4 hours. After cooling to room temperature, the reaction was concentrated under reduced pressure. The residue was dissolved in DMSO and purified by reverse phase HPLC using a gradient solvent system of acetonitrile/water modified with 0.1% TFA. The product containing fractions were concentrated under reduced pressure to afford cis-4-(5-(6-((4-(1H-1,2,3-triazol-4-yl)pyridin-2-yl)amino)-4-methylpyridin-2-yl)thiazol-2-yl)-4-hydroxycyclohexanecarboxylic acid. MS ESI calcd. for $C_{23}H_{24}N_7O_3S$ [M+H]$^+$ 478 found 478. $^1$H NMR (600 MHz, DMSO-d$_6$) δ 12.07 (br s, 1H), 10.38 (br s, 1H), 8.75 (br s, 1H), 8.35 (d, J=5.5 Hz, 1H), 8.33 (s, 1H), 8.28 (s, 1H), 7.49 (s, 1H), 7.36 (s, 1H), 7.12 (s, 1H), 5.91 (s, 1H), 2.33 (s, 3H), 2.30-2.22 (m, 1H), 1.95-1.86 (m, 2H), 1.82 (d, J=14.0 Hz, 2H), 1.80-1.73 (m, 4H).

The following examples in the table below were prepared in an analogous manner to that described for Example 2.1, step 1, and where appropriate, step 2 and/or step 3 as well.

| Ex. No. | R$^1$ | R$^A$ | Chemical Name | [M + H]$^+$ Calc'd | [M + H]$^+$ Obsv'd | Form(s) |
|---|---|---|---|---|---|---|
| 2.2 | (4-methoxybenzyl-triazolyl group) | —H | cis-4-hydroxy-4-{5-[6-({4-[1-(4-methoxybenzyl)-1H-1,2,3-triazol-4-yl]pyridin-2-yl}amino)-4-methylpyridin-2-yl]-1,3-thiazol-2-yl}cyclohexanecarboxylic acid | 598 | 598 | Free Base |
| 2.3 | (tert-butoxycarbonylamino-propoxy group) | —H | cis-4-(5-{6-[(4-{3-[(tert-butoxycarbonyl)amino]propoxy}pyridin-2-yl)amino]-4-methylpyridin-2-yl}-1,3-thiazol-2-yl)-4-hydroxycyclohexane-carboxylic acid | 584 | 584 | TFA Salt |
| 2.4 | (1-methyl-triazolyl group) | —H | cis-4-hydroxy-4-[5-(4-methyl-6-{[4-(1-methyl-1H-1,2,3-triazol-4-yl)pyridin-2-yl]amino}pyridin-2-yl)-1,3-thiazol-2-yl]cyclohexanecarboxylic acid | 492 | 492 | Free Base |

-continued

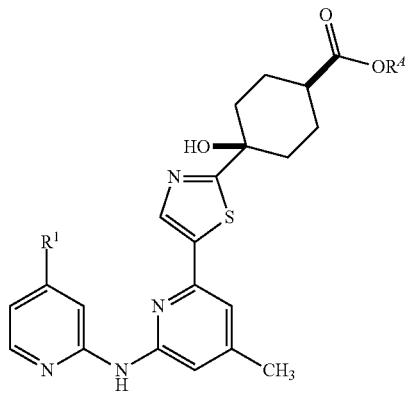

| Ex. No. | R¹ | R⁴ | Chemical Name | [M + H]⁺ Calc'd | [M + H]⁺ Obsv'd | Form(s) |
|---|---|---|---|---|---|---|
| 2.5 | 1-methyl-1,2,3-triazol-4-yl (H₃C on N1) | —CH₂CH₃ | ethyl cis-4-hydroxy-4-[5-(4-methyl-6-{[4-(1-methyl-1H-1,2,3-triazol-4-yl)pyridin-2-yl]amino}pyridin-2-yl)-1,3-thiazol-2-yl]cyclohexanecarboxylate | 520 | 520 | Free Base |
| 2.6 | 2-methyl-2H-1,2,3-triazol-4-yl | —CH₂CH₃ | ethyl cis-4-hydroxy-4-[5-(4-methyl-6-{[4-(2-methyl-2H-1,2,3-triazol-4-yl)pyridin-2-yl]amino}pyridin-2-yl)-1,3-thiazol-2-yl]cyclohexanecarboxylate | 520 | 520 | Free Base |
| 2.7 | —CH₂CO₂H | —H | cis-4-[5-(6-{[4-(carboxymethyl)pyridin-2-yl]amino}-4-methylpyridin-2-yl)-1,3-thiazol-2-yl]-4-hydroxycyclohexane-carboxylic acid | 469 | 469 | Free Base |
| 2.8 | —CO₂H | —H | 2-({6-[2-(cis-4-carboxy-1-hydroxycyclohexyl)-1,3-thiazol-5-yl]-4-methylpyridin-2-yl}amino)pyridine-4-carboxylic acid | 455 | 455 | Free Base |
| 2.9 | —CH₂CO₂CH₃ | —CH₂CH₃ | ethyl cis-4-hydroxy-4-[5-(6-{[4-(2-methoxy-2-oxoethyl)pyridin-2-yl]amino}-4-methylpyridin-2-yl)-1,3-thiazol-2-yl]cyclohexanecarboxylate | 511 | 511 | Free Base |
| 2.10 | —CO₂CH₃ | —CH₂CH₃ | methyl 2-[(6-{2-[cis-4-(ethoxycarbonyl)-1-hydroxycyclohexyl]-1,3-thiazol-5-yl}-4-methylpyridin-2-yl)amino]pyridine-4-carboxylate | 497 | 497 | Free Base |

-continued

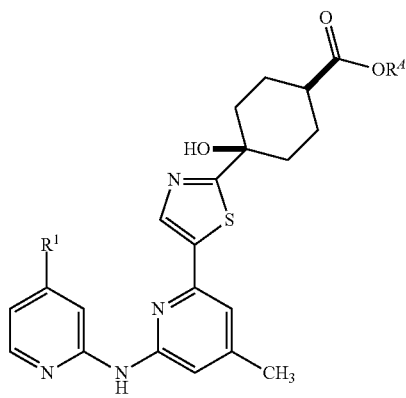

| Ex. No. | R¹ | R⁴ | Chemical Name | [M + H]⁺ Calc'd | [M + H]⁺ Obsv'd | Form(s) |
|---|---|---|---|---|---|---|
| 2.11 | 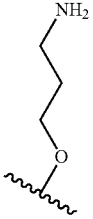 | —H | cis-4-[5-(6-{[4-(3-aminopropoxy)pyridin-2-yl]amino}-4-methylpyridin-2-yl)-1,3-thiazol-2-yl]-4-hydroxycyclohexane-carboxylic acid | 484 | 484 | TFA Salt |
| 2.12 | 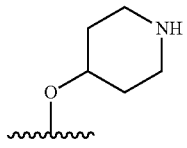 [SMILES: *OC1CCNCC1] | —H | cis-4-hydroxy-4-[5-(4-methyl-6-{[4-(piperidin-4-yloxy)pyridin-2-yl]amino}pyridin-2-yl)-1,3-thiazol-2-yl]cyclohexanecarboxylic acid | 510 | 510 | TFA Salt |
| 2.13 | 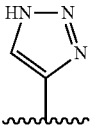 | —CH₂CH₃ | ethyl cis-4-hydroxy-4-[5-(4-methyl-6-{[4-(1H-1,2,3-triazol-4-yl)pyridin-2-yl]amino}pyridin-2-yl)-1,3-thiazol-2-yl]cyclohexanecarboxylate | 506 | 506 | Free Base |
| 2.14 | 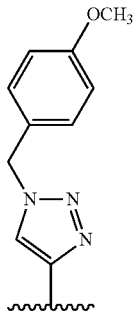 [SMILES: *c1cn(Cc2ccc(OC)cc2)nn1] | —CH₂CH₃ | ethyl cis-4-hydroxy-4-{5-[6-({4-[1-(4-methoxybenzyl)-1H-1,2,3-triazol-4-yl]pyridin-2-yl}amino)-4-methylpyridin-2-yl]-1,3-thiazol-2-yl}cyclohexanecarboxylate | 626 | 626 | Free Base |

Example 3

Preparation of Compounds of Formula (I) Using the Methods Illustrated in Scheme 1

Example 3.1

(1S,4R or 1R,4S)-4-hydroxy-2,2-dimethyl-4-[5-(4-methyl-6-{[4-(trifluoromethyl)pyridin-2-yl]amino}pyridin-2-yl)-1,3-thiazol-2-yl]cyclohexanecarboxylic acid

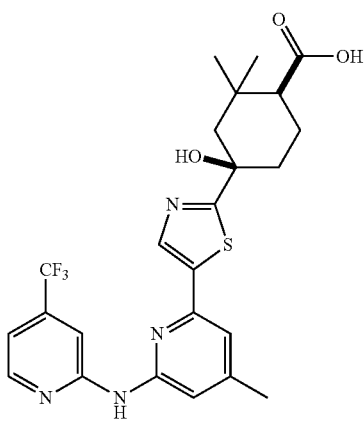

Step 1: Sodium tert-butoxide (124 mg, 1.3 mmol), 2-amino-4-(trifluoromethyl)pyridine (191 mg, 1.2 mmol), methyl (1S,4R or 1R,4S)-4-[5-(6-bromo-4-methylpyridin-2-yl)-1,3-thiazol-2-yl]-4-hydroxy-2,2-dimethylcyclohexanecarboxylate, (471 mg, 1.1 mmol), and 1,1'-bis(di-tert-butylphosphino)ferrocene palladium dichloride (70 mg, 0.11 mmol) were combined in an oven-dried, $N_2$ cooled vial. Added dioxane (7.1 mL), and the reaction was stirred at 80° C. for 2 hours. Upon cooling to room temperature, the mixture was filtered through CELITE and purified by reverse phase (C-18) preparative HPLC (55:45 to 90:10 acetonitrile:water: 0.1% v/v trifluoroacetic acid modifier) to afford (4S)-5,5-dimethyl-1-[5-(4-methyl-6-{[4-(trifluoromethyl)pyridin-2-yl]amino}pyridin-2-yl)-1,3-thiazol-2-yl]-2-oxabicyclo[2.2.2]octan-3-one. MS ESI calcd. for $C_{24}H_{24}F_3N_4O_2S$ $[M+H]^+$ 489. found 489.

Step 2: Sodium hydroxide (1.0 M in water, 0.1 mL, 0.1 mmol) was added to (4S)-5,5-dimethyl-1-[5-(4-methyl-6-{[4-(trifluoromethyl)pyridin-2-yl]amino}pyridin-2-yl)-1,3-thiazol-2-yl]-2-oxabicyclo[2.2.2]octan-3-one (10 mg, 0.02 mmol) dissolved in tetrahydrofuran (0.2 mL), methanol (0.05 mL), and water (0.05 mL). The mixture was stirred at 65° C. for 5 hours. The reaction was cooled to room temperature, quenched with hydrochloric acid (1.0 M in water, 0.1 mL), and filtered. The filter caked was dried to afford (1S,4R or 1R,4S)-4-hydroxy-2,2-dimethyl-4-[5-(4-methyl-6-{[4-(trifluoromethyl)pyridin-2-yl]amino}pyridin-2-yl)-1,3-thiazol-2-yl]cyclohexanecarboxylic acid. MS ESI calcd. for $C_{24}H_{26}F_3N_4O_3S$ $[M+H]^+$ 507. found 507. $^1$H NMR (500 MHz, DMSO-$d_6$) δ 10.18 (s, 1H), 8.61 (s, 1H), 8.48 (d, J=5.1 Hz, 1H), 8.25 (s, 1H), 7.34 (s, 1H), 7.21 (d, J=5.4 Hz, 1H), 7.11 (s, 1H), 5.80 (s, 1H), 2.30 (s, 3H), 2.15-2.12 (m, 1H), 2.07-1.97 (m, 1H), 1.86-1.82 (m, 4H), 1.68-1.65 (m, 1H), 1.58-1.55 (m, 1H), 1.12 (s, 3H), 1.00 (s, 3H).

The examples in the following table were prepared in an analogous manner to that described for Example 3.1, step 1, and where appropriate, step 2 as well.

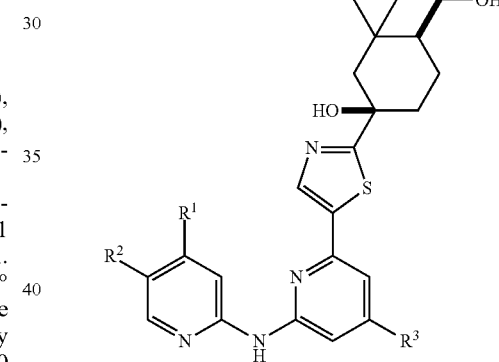

Illustration above indicates relative stereochemistry only.

| Ex. No. | $R^1$ | $R^2$ | $R^3$ | Chemical Name | $[M + H]^+$ Calc'd | $[M + H]^+$ Obsv'd | Form(s) |
|---|---|---|---|---|---|---|---|
| 3.2 | —C(CH$_3$)$_3$ | —H | —H | (1R,4S or 1S,4R)-4-(5-{6-[(4-tert-butylpyridin-2-yl)amino]pyridin-2-yl}-1,3-thiazol-2-yl)-4-hydroxy-2,2-dimethylcyclohexanecarboxylic acid | 481 | 481 | Formate Salt |
| 3.3 | —CF$_3$ | —H | —H | (1R,4S or 1S,4R)-4-hydroxy-2,2-dimethyl-4-[5-(6-{[4-(trifluoromethyl)pyridin-2-yl]amino}pyridin-2-yl)-1,3-thiazol-2-yl]cyclohexanecarboxylic acid | 493 | 493 | Formate Salt |
| 3.4 | —CH$_3$ | —F | —H | (1R,4S or 1S,4R)-4-(5-{6-[(5-fluoro-4-methylpyridin-2-yl)amino]pyridin-2-yl}-1,3-thiazol-2-yl)-4-hydroxy-2,2-dimethylcyclohexanecarboxylic acid | 457 | 457 | Formate Salt |
| 3.5 | —Cl | —H | —H | (1R,4S or 1S,4R)-4-(5-{6-[(4-chloropyridin-2-yl)amino]pyridin-2-yl}-1,3- | 459 | 459 | Formate Salt |

-continued

| Ex. No. | R¹ | R² | R³ | Chemical Name | [M + H]⁺ Calc'd | [M + H]⁺ Obsv'd | Form(s) |
|---|---|---|---|---|---|---|---|
| | | | | thiazol-2-yl)-4-hydroxy-2,2-dimethylcyclohexanecarboxylic acid | | | |
| 3.6 | —C(CH₃)₃ | —H | —H | (1R,4S or 1S,4R)-4-(5-{6-[(4-tert-butylpyridin-2-yl)amino]pyridin-2-yl}-1,3-thiazol-2-yl)-4-hydroxy-2,2-dimethylcyclohexanecarboxylic acid | 481 | 481 | Formate Salt |
| 3.7 | —CF₃ | —H | —H | (1R,4S or 1S,4R)-4-hydroxy-2,2-dimethyl-4-[5-(6-{[4-(trifluoromethyl)pyridin-2-yl]amino}pyridin-2-yl)-1,3-thiazol-2-yl]cyclohexanecarboxylic acid | 493 | 493 | Formate Salt |
| 3.8 | —CH₃ | —F | —H | (1R,4S or 1S,4R)-4-(5-{6-[(5-fluoro-4-methylpyridin-2-yl)amino]pyridin-2-yl}-1,3-thiazol-2-yl)-4-hydroxy-2,2-dimethylcyclohexanecarboxylic acid | 457 | 457 | Formate Salt |
| 3.9 | —Cl | —H | —H | (1R,4S or 1S,4R)-4-(5-{6-[(4-chloropyridin-2-yl)amino]pyridin-2-yl}-1,3-thiazol-2-yl)-4-hydroxy-2,2-dimethylcyclohexanecarboxylic acid | 459 | 459 | Formate Salt |
| 3.10 | —H | —F | —H | (1R,4S or 1S,4R)-4-(5-{6-[(5-fluoropyridin-2-yl)amino]pyridin-2-yl}-1,3-thiazol-2-yl)-4-hydroxy-2,2-dimethylcyclohexanecarboxylic acid | 443 | 443 | Formate Salt |
| 3.11 | —CH₃ | —Cl | —H | (1R,4S or 1S,4R)-4-(5-{6-[(5-chloro-4-methylpyridin-2-yl)amino]pyridin-2-yl}-1,3-thiazol-2-yl)-4-hydroxy-2,2-dimethylcyclohexanecarboxylic acid | 473 | 473 | Formate Salt |
| 3.12 | —CH₃ | —H | —H | (1R,4S or 1S,4R)-4-hydroxy-2,2-dimethyl-4-(5-{6-[(4-methylpyridin-2-yl)amino]pyridin-2-yl}-1,3-thiazol-2-yl)cyclohexanecarboxylic acid | 439 | 439 | Formate Salt |
| 3.13 | —CH₃ | —Cl | —CH₃ | (1R,4S or 1S,4R)-4-(5-{6-[(5-chloro-4-methylpyridin-2-yl)amino]-4-methylpyridin-2-yl}-1,3-thiazol-2-yl)-4-hydroxy-2,2-dimethylcyclohexanecarboxylic acid | 487 | 487 | Chloride Salt |
| 3.14 | —OCH₃ | —H | —CH₃ | (1R,4S or 1S,4R)-4-hydroxy-4-(5-{6-[(4-methoxypyridin-2-yl)amino]-4-methylpyridin-2-yl}-1,3-thiazol-2-yl)-2,2-dimethylcyclohexanecarboxylic acid | 469 | 469 | TFA Salt |
| 3.15 | —CH₃ | —F | —CH₃ | (1R,4S or 1S,4R)-4-(5-{6-[(5-fluoro-4-methylpyridin-2-yl)amino]-4-methylpyridin-2-yl}-1,3-thiazol-2-yl)-4-hydroxy-2,2-dimethylcyclohexanecarboxylic acid | 471 | 471 | Free Base |
| 3.16 | —C(CH₃)₃ | —H | —CH₃ | (1R,4S or 1S,4R)-4-(5-{6-[(4-tert-butylpyridin-2-yl)amino]-4-methylpyridin-2-yl}-1,3-thiazol-2-yl)-4-hydroxy-2,2-dimethylcyclohexanecarboxylic acid | 495 | 495 | Free Base |

-continued

| Ex. No. | $R^1$ | $R^2$ | $R^3$ | Chemical Name | $[M+H]^+$ Calc'd | $[M+H]^+$ Obsv'd | Form(s) |
|---|---|---|---|---|---|---|---|
| 3.17 | —CH$_3$ | —H | —CH$_3$ | (1R,4S or 1S,4R)-4-hydroxy-2,2-dimethyl-4-(5-{4-methyl-6-[(4-methylpyridin-2-yl)amino]pyridin-2-yl}-1,3-thiazol-2-yl)cyclohexanecarboxylic acid | 453 | 453 | TFA Salt |
| 3.18 | —CF$_3$ | —H | —CH$_3$ | (1R,4S or 1S,4R)-4-hydroxy-2,2-dimethyl-4-[5-(4-methyl-6-{[4-(trifluoromethyl)pyridin-2-yl]amino}pyridin-2-yl)-1,3-thiazol-2-yl]cyclohexanecarboxylic acid | 507 | 507 | Free Base |

Example 4

Preparation of Compounds of Formula (I) Using the Methods Illustrated in Scheme 2

Examples 4.1 and 4.2

Cis- or trans-2-Hydroxy-2-(5-(4-methyl-6-((4-(trifluoromethyl)pyridin-2-yl)amino)pyridin-2-yl)thiazol-2-yl)spiro[3.5]nonane-carboxylic acid (Isomer 1) and cis- or trans-2-Hydroxy-2-(5-(4-methyl-6-((4-(trifluoromethyl)pyridin-2-yl)amino)pyridin-2-yl)thiazol-2-yl)spiro[3.5]nonane-carboxylic acid (Isomer 2)

4.1/4.2

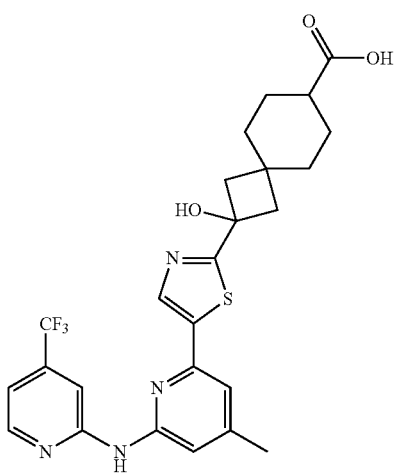

Step 1: To a flask containing butyldi-1-adamantylphosphine (700 mg, 1.9 mmol) and Pd(OAc)$_2$ (215 mg, 0.98 mmol) was added dioxane (60 mL) and the mixture was stirred at 25° C. for 20 minutes. To the reaction mixture was added ethyl 2-hydroxy-2-(thiazol-2-yl)spiro[3.5]nonane-7-carboxylate (1.5 g, 5.0 mmol), 6-bromo-4-methyl-N-(4-(trifluoromethyl)pyridin-2-yl)pyridin-2-amine (2.4 g, 7.3 mmol), pivalic acid (754 mg, 7.4 mmol) and cesium fluoride (2.3 g, 15 mmol) and the mixture was stirred at 120 OC for 3 days.

After cooling to room temperature, the mixture was diluted with water and extracted with EtOAc. The organic layer was dried over anhydrous sodium sulfate, filtered, and concentrated under reduced pressure. The residue was purified by silica gel chromatography (petroleum ether: EtOAc=10:1) and subsequently was resolved by chiral supercritical fluid chromatography (OD column, CO$_2$/MeOH+0.05% ammonia) to afford cis- or trans-ethyl 2-hydroxy-2-(5-(4-methyl-6-((4-(trifluoromethyl)pyridin-2-yl)amino)pyridin-2-yl)thiazol-2-yl)spiro[3.5]nonane-7-carboxylate (Isomer 1, first eluting): MS ESI calcd. for C$_{27}$H$_{29}$F$_3$N$_4$O$_3$S [M+H]$^+$ 547. found 547 and cis- or trans-ethyl 2-hydroxy-2-(5-(4-methyl-6-((4-(trifluoromethyl)pyridin-2-yl)amino)pyridin-2-yl)thiazol-2-yl)spiro[3.5]nonane-7-carboxylate (Isomer 2, second eluting): MS ESI calcd. for C$_{27}$H$_{30}$F$_3$N$_4$O$_3$S [M+H]$^+$ 547. found 547.

Step 2: To a flask was added cis- or trans-ethyl 2-hydroxy-2-(5-(4-methyl-6-((4-(trifluoromethyl)pyridin-2-yl)amino)pyridin-2-yl)thiazol-2-yl)spiro[3.5]nonane-7-carboxylate (Isomer 1, first eluting) (80 mg, 0.15 mmol) and lithium hydroxide (11 mg, 0.44 mmol) in THF/water (2 mL/2 mL) and the mixture was stirred at 60° C. for 30 minutes. After cooling to room temperature, the pH was adjusted to around 6 by dropwise addition of HCl (2 M). The mixture was diluted with water and extracted with EtOAc. The organic layer was dried over anhydrous sodium sulfate, filtered, and concentrated under reduced pressure. The residue was purified by HPLC to afford cis- or trans-2-hydroxy-2-(5-(4-methyl-6-((4-(trifluoromethyl)pyridin-2-yl)amino)pyridin-2-yl)thiazol-2-yl)spiro[3.5]nonane-7-carboxylic acid (Isomer 1). MS ESI calcd. for C$_{25}$H$_{25}$F$_3$N$_4$O$_3$S [M+H]$^+$ 519. found 519. $^1$H NMR (400 MHz, CD$_3$OD) δ 8.58 (d, J=5.4 Hz, 1H), 8.36 (s, 1H), 8.11 (s, 1H), 7.45 (s, 1H), 7.35 (d, J=5.2 Hz, 1H), 7.04 (s, 1H), 2.55-2.61 (m, 2H), 2.44-2.58 (m, 3H), 2.20-2.29 (m, 3H), 2.03-2.14 (m, 2H), 1.83-1.87 (m, 2H), 1.46-1.59 (m, 4H).

The following examples in the tables below were prepared in an analogous manner to that described for Example 4.1, step 1, and where appropriate, step 2 as well.

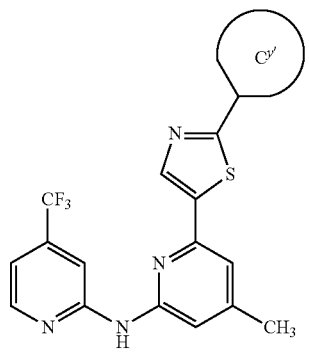 [SMILES: Cc1cc(Nc2cc(C(F)(F)F)ccn2)nc(-c2cnc(C(C)C)s2)c1]

| Ex. No. | C$^{y'}$ | Chemical Name | [M + H]$^+$ Calc'd | [M + H]$^+$ Obsv'd | Form(s) |
|---|---|---|---|---|---|
| 4.2 | 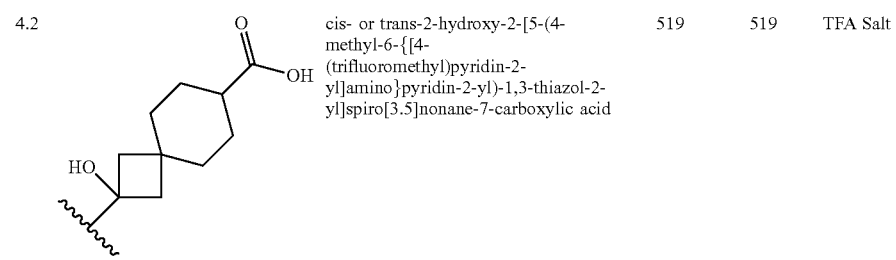  Isomer 2 | cis- or trans-2-hydroxy-2-[5-(4-methyl-6-{[4-(trifluoromethyl)pyridin-2-yl]amino}pyridin-2-yl)-1,3-thiazol-2-yl]spiro[3.5]nonane-7-carboxylic acid | 519 | 519 | TFA Salt |
| 4.3 | 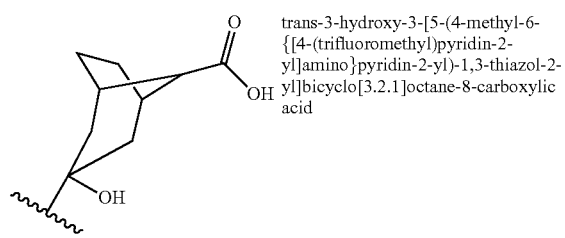 | trans-3-hydroxy-3-[5-(4-methyl-6-{[4-(trifluoromethyl)pyridin-2-yl]amino}pyridin-2-yl)-1,3-thiazol-2-yl]bicyclo[3.2.1]octane-8-carboxylic acid | 505 | 505 | Free Base |
| 4.4 | 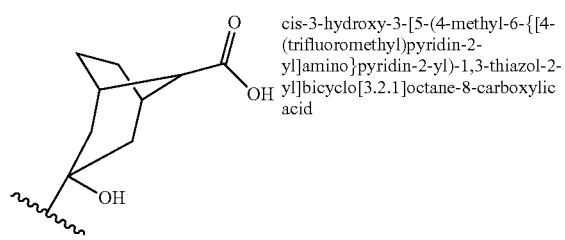 | cis-3-hydroxy-3-[5-(4-methyl-6-{[4-(trifluoromethyl)pyridin-2-yl]amino}pyridin-2-yl)-1,3-thiazol-2-yl]bicyclo[3.2.1]octane-8-carboxylic acid | 505 | 505 | Free Base |

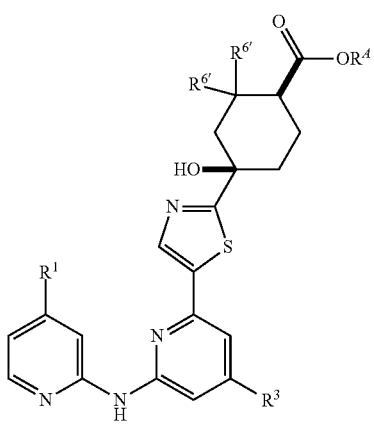

Illustration shows relative stereochemistry only.

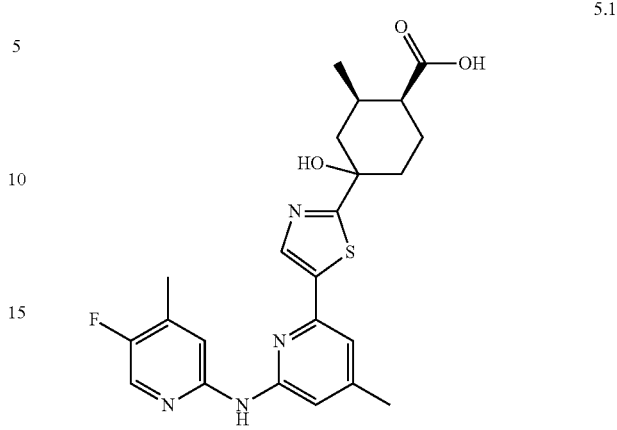

| Ex. No. | $R^1$ | $R^3$ | $R^{6'}$ | $R^4$ | Chemical Name | $[M + H]^+$ Calc'd | $[M + H]^+$ Obsv'd | Form |
|---|---|---|---|---|---|---|---|---|
| 4.5 | —OC(H)(CH$_3$)$_2$ | —CH$_3$ | —H | —H | cis-4-hydroxy-4-[5-(4-methyl-6-{[4-(1-methylethoxy)pyridin-2-yl]amino}pyridin-2-yl)-1,3-thiazol-2-yl]cyclohexanecarboxylic acid | 469 | 469 | Free Base |
| 4.6 | —CF$_3$ | —CH$_3$ | —H | —H | cis-4-hydroxy-4-[5-(4-methyl-6-{[4-(trifluoromethyl)pyridin-2-yl]amino}pyridin-2-yl)-1,3-thiazol-2-yl]cyclohexanecarboxylic acid | 479 | 479 | Free Base |
| 4.7 | —CF$_3$ | —CH$_2$OCH$_3$ | —CH$_3$ | —H | (1R,4S or 1S,4R)-4-hydroxy-4-{5-[4-(methoxymethyl)-6-{[4-(trifluoromethyl)pyridin-2-yl]amino}pyridin-2-yl]-1,3-thiazol-2-yl}-2,2-dimethylcyclohexanecarboxylic acid | 537 | 537 | Free Base |
| 4.8 | —CF$_3$ | —CH$_2$OCH$_3$ | —CH$_3$ | —CH$_3$ | methyl (1R,4S or 1S,4R)-4-hydroxy-4-{5-[4-(methoxymethyl)-6-{[4-(trifluoromethyl)pyridin-2-yl]amino}pyridin-2-yl]-1,3-thiazol-2-yl}-2,2-dimethylcyclohexanecarboxylate | 551 | 551 | Free Base |

Example 5

Preparation of Compounds of Formula (I) Using the Methods Illustrated in Scheme 4

Example 5.1

Rel-(1S,2R,4R or S)-4-(5-(6-((5-Fluoro-4-methyl-pyridin-2-yl)amino)-4-methylpyridin-2-yl)thiazol-2-yl)-4-hydroxy-2-methylcyclohexanecarboxylic acid (Isomer 1)

Step 1: 2,6-Dibromo-4-methylpyridine (39 mg, 0.16 mmol), potassium carbonate (79 mg, 0.57 mmol) and 1,1'-bis(diphenylphosphino)ferroncene palladium dichloride (6.9 mg, 9.5 µmol) were combined in a vial and purged with argon (5×). In a separate vial, a solution of 5-(4,4,5,5-tetramethyl-1,3,2-dioxaborolan-2-yl)thiazole (40 mg, 0.19 mmol) in DMF (1.3 mL) was degassed by bubbling through a nitrogen stream for 10 minutes. The latter solution was then added to the reaction vial and the reaction mixture was stirred at 80° C. overnight. After cooling to room temperature, the reaction mixture was diluted with EtOAc and washed with brine. The organic layer was dried over anhydrous sodium sulfate and concentrated under reduced pressure. The residue was purified by column chromatography on silica (7-60% EtOAc/hexanes) to afford 5-(6-bromo-4-methylpyridin-2-yl)thiazole as a pale yellow solid. MS ESI calcd. for $C_9H_7BrN_2S$ [M+H]$^+$ 256. found 256.

Step 2: 5-(6-Bromo-4-methylpyridin-2-yl)thiazole (0.52 g, 2.019 mmol) in THF (20 mL) was placed under an argon atmosphere and cooled to −78° C. LDA (1.35 mL, 2.42 mmol) was added and the solution was stirred for 30 minutes at −78° C. Ethyl rel-(1S,2R)-2-methyl-4-oxocyclohexanecarboxylate (Tetrahedron Letters, 1994, 35(46), 8649-8650.) (0.39 g, 2.12 mmol) in THF (5 mL) was added and the solution was stirred for one hour at −78° C. The reaction mixture was quenched with saturated ammonium chloride, warmed to room temperature and diluted with EtOAc. The organic layer was washed with saturated sodium bicarbonate, then brine, dried over anhydrous sodium sulfate, filtered and concentrated under reduced pressure. The residue was purified by column chromatography on silica (5-40% EtOAc/hexanes) to afford ethyl rel-(1S,2R)-4-(5-(6-bromo-4-methylpyridin-2-yl)thiazol-2-yl)-4-hydroxy-2-methylcyclohexanecarboxylate as a pale yellow foam. The racemic mixture was purified by chiral SFC (40-60% methanol/$CO_2$) to afford ethyl rel-(1S,2R,4R or S)-4-(5-(6-bromo-4-methylpyridin-2-yl)thiazol-2-yl)-4-hydroxy-2-methylcyclohexanecarboxylate (Isomer 1, first eluting): MS ESI calcd. for $C_{19}H_{24}BrN_2O_3S$ [M+H]$^+$ 441. found 441 and ethyl rel-(1S,2R,4R or S)-4-(5-(6-bromo-4-methylpyridin-2-yl)thiazol-2-yl)-4-hydroxy-2-methylcyclohexanecarboxylate (Isomer 2, second eluting): MS ESI calcd. for $C_{19}H_{24}BrN_2O_3S$ [M+H]$^+$ 441. found 441.

Step 3: 5-Fluoro-4-methylpyridin-2-amine (14.35 mg, 0.11 mmol), ethyl rel-(1S,2R,4R or S)-4-(5-(6-bromo-4-methylpyridin-2-yl)thiazol-2-yl)-4-hydroxy-2-methylcyclohexanecarboxylate (Isomer 1, first eluting) (50 mg, 0.11 mmol), xantphos (9.88 mg, 0.02 mmol), cesium carbonate (74.2 mg, 0.23 mmol), palladium(II) acetate (2.55 mg, 0.01 mmol) and dioxane (1.1 mL) were combined, placed under an argon atmosphere and then stirred at 100° C. for 90 minutes. The reaction mixture was diluted with EtOAc, filtered by CELITE, and the filtrate was concentrated under reduced pressure. The reside was purified by column chromatography on silica (0-100% EtOAc/hexanes) to afford ethyl rel-(1S,2R,4R or S)-4-(5-(6-((5-fluoro-4-methylpyridin-2-yl)amino)-4-methylpyridin-2-yl)thiazol-2-yl)-4-hydroxy-2-methylcyclohexanecarboxylate as a pale yellow foam. MS ESI calcd. for $C_{25}H_{34}O_3S$ [M+H]$^+$ 485. found 485.

Step 4: A vial was charged with ethyl rel-(1S,2R,4R or S)-4-(5-(6-((5-fluoro-4-methylpyridin-2-yl)amino)-4-methylpyridin-2-yl)thiazol-2-yl)-4-hydroxy-2-methylcyclohexanecarboxylate (31 mg, 0.06 mmol), MeOH (3.0 mL) and NaOH (1M, 500 μL, 0.50 mmol). The mixture was heated to 100 OC in a microwave for 15 minutes. Additional sodium hydroxide (IM in water, 250 uL) was added and the mixture was then heated to 100° C. in a microwave for 15 minutes. The pH was adjusted to 3-4 with HCl (1 M) and the resulting mixture was diluted with water and 10% IPA/$CHCl_3$. The mixture was extracted with 10% IPA/CHCl3 and the combined organics were washed with water, dried over anhydrous sodium sulfate, filtered and concentrated under reduced pressure to afford rel-(1S,2R,4R or S)-4-(5- (6-((5-fluoro-4-methylpyridin-2-yl)amino)-4-methylpyridin-2-yl)thiazol-2-yl)-4-hydroxy-2-methylcyclohexanecarboxylic acid (Isomer 1) as a yellow solid. MS ESI calcd. for $C_{23}H_{26}FN_4O_3S$ [M+H]$^+$ 457. found 457. $^1$H NMR (500 MHz, DMSO-d$^6$) δ 9.68 (s, 1H), 8.23 (s, 1H), 8.16-8.06 (m, 2H), 7.26 (s, 1H), 7.07 (s, 1H), 2.32 (s, 3H), 2.28 (s, 3H), 2.18-2.05 (m, 1H), 1.99-1.82 (m, 5H), 1.73-1.59 (m, 1H), 1.01 (m, 6H).

Example 5.2

Rel-(1S,2R,4R or S)-4-(5-(6-((5-Fluoro-4-methylpyridin-2-yl)amino)-4-methylpyridin-2-yl)thiazol-2-yl)-4-hydroxy-2-methylcyclohexanecarboxylic acid (Isomer 2)

The same procedures described in steps 3 and 4 were repeated using Isomer 2 from step 2 to afford rel-(1S,2R,4R or S)-4-(5-(6-((5-Fluoro-4-methylpyridin-2-yl)amino)-4-methylpyridin-2-yl)thiazol-2-yl)-4-hydroxy-2-methylcyclohexanecarboxylic acid (Isomer 2). ESI calcd. for $C_{23}H_{26}FN_4O_3S$ [M+H]$^+$ 457. found 457.

Example 6

Preparation of Compounds of Formula (I) Using the Methods Illustrated in Scheme 3

Example 6.1

Rel-(1S,2R)-4-Hydroxy-4-(5-(6-((4-hydroxypyridin-2-yl)amino)-4-methylpyridin-2-yl)thiazol-2-yl)-2-methylcyclohexanecarboxylic acid

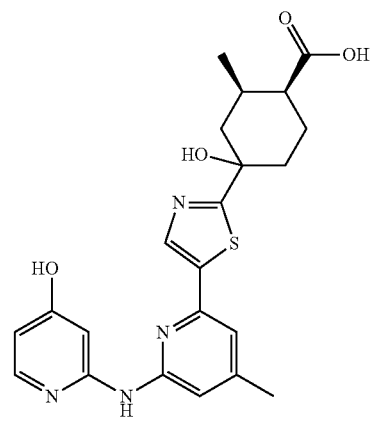

6.1

Step 1a: To a flask was added ethyl rel-(1S,2R)-2-methyl-4-oxocyclohexanecarboxylate (Tetrahedron Letters, 1994, 35(46), 8649-8650.) (80.0 g, 434 mmol) and thiazole (50.8 mL, 716 mmol) followed by THF (560 mL). The mixture was cooled in a dry ice/acetone bath. n-Butyl lithium was added dropwise and the internal temperature of the reaction was kept below −65° C. After an addition time of one hour the reaction was maintained below −65° C. for one hour. The reaction was then quenched at low temperature by addition of methanol (18 mL). The reaction was diluted with water and transferred to a separatory funnel. Ethyl acetate was added and the organic phase was separated, the aqueous phase was washed with a second portion of ethyl acetate. The combined organic layers were dried over anhydrous magnesium sulfate, filtered and concentrated under reduced pressure. The residue was purified by silica gel chromatography (EtOAc/hexanes) to afford ethyl rel-(1S,2R)-4-hydroxy-2-methyl-4-(thiazol-2-yl)cyclohexanecarboxylate. MS ESI calcd for $C_{13}H_{20}NO_3S$ [M+H]$^+$ 270. found 270. $^1$H NMR (600 MHz, CDCl$_3$) δ 7.66 (d, J=3.5 Hz, 1H), 7.24 (d, J=3.5 Hz, 1H), 4.17-4.08 (m, 2H), 2.79 (s, 1H), 2.54-2.60 (m, 1H), 2.32-2.38 (m, 1H), 2.20 (dd, J=5.0, 13.8 Hz, 1H), 1.98-2.10 (m, 4H), 1.25 (t, J=7.0 Hz, 3H), 1.08 (d, J=7.3 Hz, 3H).

Step 1b: A solution of pivalic anhydride (235 mg, 1.26 mmol) in DCM (1.2 mL) was treated with 4-dimethylaminopyridine (14.0 mg, 0.12 mmol), triethylamine (0.21 mL, 1.49 mmol) and 4-hydroxy-2-bromo-pyridine (200 mg, 1.15 mmol). The resulting solution was stirred for 16 hours at room temperature. The reaction mixture was loaded onto a silica gel column and purified by silica gel chromatography (0-40% EtOAc/hexanes) to afford 2-bromopyridin-4-yl pivalate. MS ESI calcd for $C_{10}H_{13}BrNO_2$ [M+H]$^+$ 258. found 258. $^1$H NMR (500 MHz, d$_6$DMSO) δ 8.42 (dd, J=1.3, 5.4 Hz, 1H), 7.61 (s, 1H), 7.32 (dd, J=1.3, 5.4 Hz, 1H), 1.28 (s, 9H).

Step 1c: A round bottom flask was charged with tert-butyl carbamate (5.60 g, 47.8 mmol), 1,1'-bis(di-tert-butylphosphino)ferrocene (1.51 g, 3.19 mmol), sodium tert-butoxide (4.60 g, 47.8 mmol), 2,6-dibromo-4-methylpyridine (10.0 g, 39.9 mmol) and tris(dibenzylideneacetone)dipalladium(0) (1.46 g, 1.59 mmol). 2-Methyl-tetrahydrofuran (100 mL) was added and the reaction was heated to 70 OC for 5 hours. The reaction was transferred to a separatory funnel and diluted with brine and ethyl acetate. The organic layer was separated, dried over anhydrous magnesium sulfate, filtered and concentrated under reduced pressure. The reaction mixture was loaded onto a silica gel column and purified by silica gel chromatography (10-100% EtOAc/hexanes) to afford tert-butyl (6-bromo-4-methylpyridin-2-yl)carbamate. MS ESI calcd for $C_{11}H_{16}BrN_2O_2$ [M+H]$^+$ 287. found 287. $^1$H NMR (600 MHz, CDCl$_3$) δ 7.69 (s, 1H), 7.16 (s, 1H), 6.95 (s, 1H), 2.29 (s, 3H), 1.48 (s, 9H).

Step 2: A microwave vial was charged with tert-butyl (6-bromo-4-methylpyridin-2-yl)carbamate (535 mg, 1.86 mmol), ethyl rel-(1S,2R)-4-hydroxy-2-methyl-4-(thiazol-2-yl)cyclohexanecarboxylate (400 mg, 1.48 mmol), potassium carbonate (616 mg, 4.46 mmol), pivalic acid (0.26 mL, 2.23 mmol), allylpalladium(II)chloride dimer (54.3 mg, 0.15 mmol) and n-butyldi-1-adamantylphosphine (213 mg, 0.59 mmol). Dimethylacetamide (2.97 mL) was added and the reaction was heated to 100° C. for 3 hours. The reaction mixture was diluted with ethyl acetate and filtered through CELITE with ethyl acetate eluent. The combined filtrate was concentrated under reduced pressure. The residue was purified by reversed phase chromatography (Gilson, 10-100% ACN/H$_2$O) to afford ethyl rel-(1S,2R)-4-(5-(6-((tert-butoxycarbonyl)amino)-4-methylpyridin-2-yl)thiazol-2-yl)-4-hydroxy-2-methylcyclohexanecarboxylate. MS ESI calcd for $C_{24}H_{34}N_3O_5$ [M+H]$^+$ 476. found 476 $^1$H NMR (500 MHz, d$_6$DMSO) δ 9.62 (s, 1H), 8.19 (s, 1H), 7.51 (s, 1H), 7.36 (s, 1H), 5.86 (s, 1H), 4.10-4.00 (m, 2H), 2.53-2.59 (m, 1H), 2.22-2.37 (m, 3H), 2.02-2.14 (m, 2H), 1.82-1.92 (m, 4H), 1.68-1.74 (m, 1H), 1.44 (s, 9H), 1.16 (t, J=7.3 Hz, 3H), 0.97 (d, J=7.3 Hz, 3H).

Step 3: To a solution of ethyl rel-(1S,2R)-4-(5-(6-((tert-butoxycarbonyl)amino)-4-methylpyridin-2-yl)thiazol-2-yl)-4-hydroxy-2-methylcyclohexanecarboxylate (380 mg, 0.80 mmol) in DCM (3 mL) was added trifluoroacetic acid (1 mL, 12.98 mmol). The reaction was stirred at room temperature for 6 hours. The reaction was concentrated under reduced pressure. The residue was taken up in methanol (10 mL) and aqueous potassium hydroxide (2 mL, 40% by weight, 14.26 mmol) was added. The reaction was heated to reflux for 90 minutes. The reaction mixture was transferred to a separatory funnel and diluted with ethyl acetate and water. The aqueous phase was brought to a pH of approximately 2 by addition of pH 3 phosphate buffer (30 mL) and 2N hydrochloric acid (5 mL). The aqueous phase was washed with ethyl acetate (3×). The combined organic layers were dried over anhydrous magnesium sulfate, filtered and concentrated under reduced pressure to afford ethyl rel-(1S,2R)-4-(5-(6-amino-4-methylpyridin-2-yl)thiazol-2-yl)-4-hydroxy-2-methylcyclohexanecarboxylate.

Step 4: To a flask was added ethyl rel-(1S,2R)-4-(5-(6-amino-4-methylpyridin-2-yl)thiazol-2-yl)-4-hydroxy-2-methylcyclohexanecarboxylate (180 mg, 0.52 mmol), 2-bromopyridin-4-yl pivalate (201 mg, 0.78 mmoles), potassium phosphate tribasic (220 mg, 1.04 mmol), tris(dibenzylideneacetone)dipalladium(0) (24 mg, 0.03 mmol) and 2-dicyclohexylphosphino-2',2',6'-triisopropylbiphenyl (49 mg, 0.10 mmol). Degassed dioxane (1.7 mL) was added and the reaction was heated to 80° C. for two hours. After cooling to room temperature, the reaction was filtered through CELITE and the cake was washed with methanol. The filtrate was concentrated under reduced pressure. The residue was purified by reversed phase HPLC (water/ACN, 10-65%) to afford rel-(1S,2R)-2-((4-methyl-6-(2-(5-methyl-3-oxo-2-oxabicyclo[2.2.2]octan-1-yl)thiazol-5-yl)pyridin-2-yl)amino) pyridin-4-yl pivalate 2,2,2-trifluoroacetate. MS ESI calcd for $C_{20}H_{31}N_4O_4S$ [M+H]$^+$ 507. found 507. $^1$H NMR (500 MHz, CD$_3$OD) δ 8.47 (d, J=4.9 Hz, 1H), 8.34 (s, 1H), 7.60 (s, 1H), 7.37 (s, 1H), 7.21 (d, J=6.8 Hz, 1H), 6.92 (s, 1H), 2.62-2.68 (m, 2H), 2.49 (s, 3H), 2.45 (s, 1H), 2.27 (dd, J=5.2, 14.2 Hz, 1H), 2.00-2.14 (m, 4H), 1.82-1.92 (m, 1H), 1.40 (s, 9H), 1.17 (d, J=7.1 Hz, 3H).

Step 5: A solution of rel-(1S,2R)-2-((4-methyl-6-(2-(5-methyl-3-oxo-2-oxabicyclo[2.2.2]octan-1-yl)thiazol-5-yl) pyridin-2-yl)amino)pyridin-4-yl pivalate 2,2,2-trifluoroacetate (33 mg, 0.06 mmol) in methanol (2 mL) was treated with aqueous potassium hydroxide (0.40 mL, 40% by weight, 2.85 mmol). The reaction was heated to 85° C. for 60 minutes. After cooling to room temperature, the reaction was acidified with trifluoroacetic acid (0.15 mL, 3.91 mmol). The solution was filtered and the filtrate was concentrated under reduced pressure. The residue was purified by reversed phase HPLC (Gilson, ACN/water, 0-50%) to afford rel-(1S,2R)-4-hydroxy-4-(5-(6-((4-hydroxypyridin-2-yl)amino)-4-methylpyridin-2-yl)thiazol-2-yl)-2-methylcyclohexanecarboxylic acid. MS ESI calcd for $C_{22}H_{25}N_4O_4S$ [M+H]$^+$ 441. found 441. $^1$H NMR (500 MHz, d$_6$DMSO) δ 11.31 (s, 1H), 8.38 (s, 1H), 8.21 (d, J=6.8 Hz, 1H), 7.49 (s, 1H), 6.77-6.82 (m, 2H), 6.75 (d, J=6.9 Hz, 1H), 2.37 (s, 3H), 2.28-2.34 (m, 1H), 2.06-2.20 (m, 2H), 1.86-1.96 (m, 4H), 1.68-1.76 (m, 2H), 1.04 (d, J=7.1 Hz, 3H).

Example 7

Compounds of Formula (I) Using the General Methods Illustrated in Scheme 7

The description provided in Example 7 is a prophetic example.

Procedure A

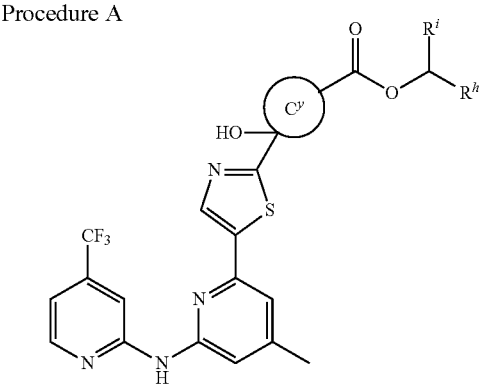

This general procedure describes the procedure for conversion of (A1) to (A) as shown in Scheme 7. To a mixture of compound of formula (A1) (1 mmol), 1° or 2° alcohol (5 mmol), and triphenylphosphine (resin-bound, 1.6 mmol/g loading, 2 mmol) in tetrahydrofuran is added di-tert-butyl azodicarboxylate (2 mmol) at 20° C. The reaction mixture is stirred at 20° C. for 16 hours. The reaction mixture is diluted with TFA (1 mL) and water (1 drop). The mixture is stirred for 30 minutes. The mixture is then filtered through CELITE, washing with dichloromethane (3×). The filtrate is concentrated under reduced pressure to afford the crude residue TFA salt. The residue is diluted carefully with saturated aqueous sodium bicarbonate solution and ethyl acetate. The organic layer is separated, washed with brine, dried over magnesium sulfate, filtered, and concentrated under reduced pressure to afford the crude residue free base. The residue is purified by silica gel chromatography to afford the product residue. The residue is lyophilized from acetonitrile and water to afford a compound of structural subtype (A).

The following compounds could be prepared according to procedures which are analogous to those described in Example 7, Procedure A.

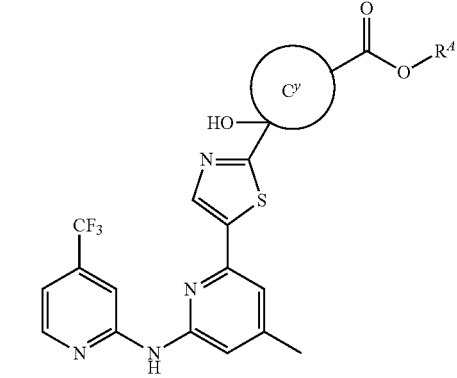

| Ex. No. | $R^A$ |
|---|---|
| 7.1 | 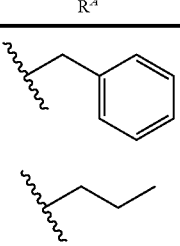 |
| 7.2 | 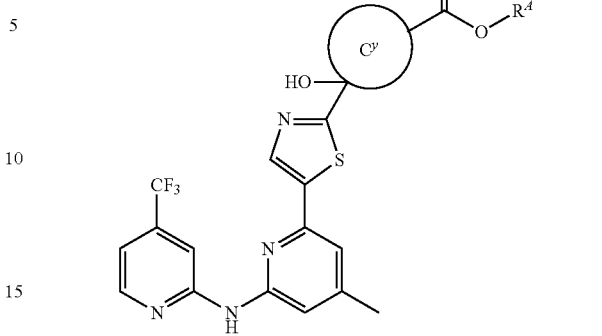 |

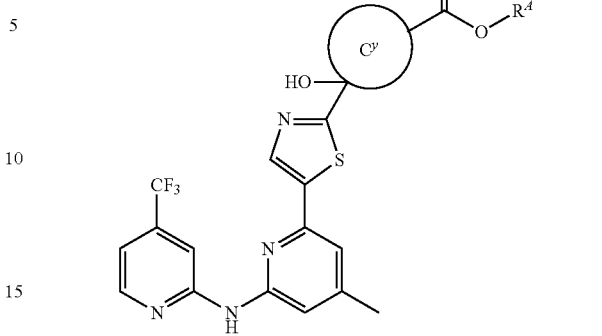

| Ex. No. | $R^A$ |
|---|---|
| 7.3 | 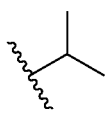 [SMILES: *C(C)C] |
| 7.4 | 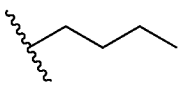 [SMILES: *CCCC] |
| 7.5 | 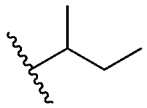 [SMILES: *C(C)CC] |
| 7.6 | 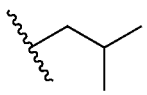 [SMILES: *CC(C)C] |
| 7.7 | 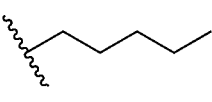 [SMILES: *CCCCC] |
| 7.8 | 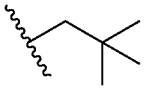 [SMILES: *CC(C)(C)C] |
| 7.9 | 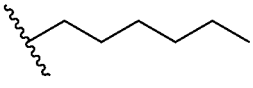 [SMILES: *CCCCCC] |
| 7.10 | 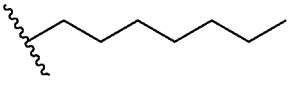 [SMILES: *CCCCCCC] |
| 7.11 | 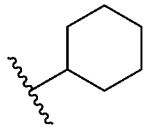 |
| 7.12 | 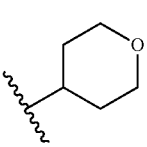 |

-continued

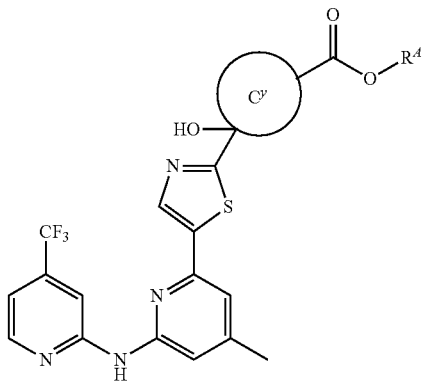

| Ex. No. | $R^A$ |
|---|---|
| 7.13 | 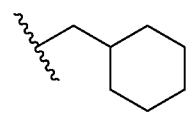 [SMILES: *CC1CCCCC1] |
| 7.14 | 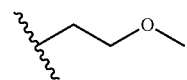 [SMILES: *CCOC] |
| 7.15 | 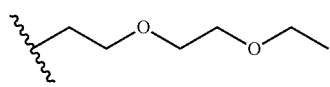 [SMILES: *CCOCCOCC] |
| 7.16 | 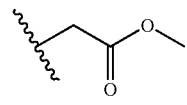 [SMILES: *CC(=O)OC] |
| 7.17 | 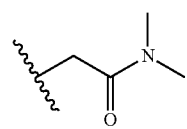 [SMILES: *CC(=O)N(C)C] |
| 7.18 | 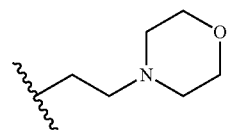 [SMILES: *CCN1CCOCC1] |
| 7.19 | 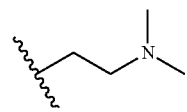 [SMILES: *CCN(C)C] |
| 7.20 | 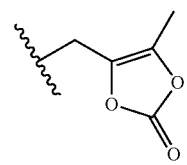 [SMILES: *Cc1oc(=O)oc1C] |

Procedure B

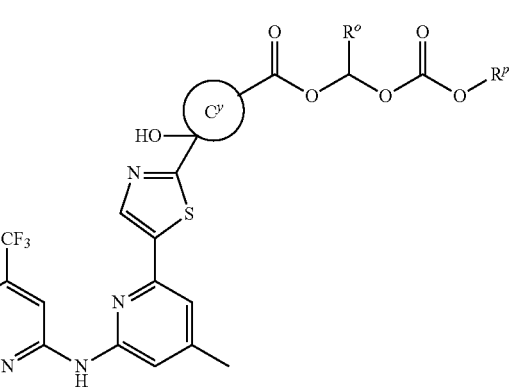

This general procedure describes the procedure for conversion of (A1) to (C) as shown in Scheme 7. A mixture of compound of formula (A1) (1.0 mmol), potassium carbonate (2.0 mmol), and sodium iodide (0.50 mmol) in DMF is stirred at 20° C. After 30 minutes, alkyl halide of formula (Cl) (0.95 mmol) is added and the reaction mixture is stirred at 20° C. After 16 hours, the reaction mixture is diluted with ethyl acetate and washed with water (4×). The organic layer is separated, washed with brine, dried over magnesium sulfate, filtered, and concentrated under reduced pressure to afford the crude residue. The residue is purified by silica gel chromatography (ethyl acetate/hexanes, linear gradient) to afford the product residue. The residue is lyophilized from acetonitrile and water to afford a compound of formula (C).

The following compounds could be prepared according to procedures which are analogous to those described in Example 7, Procedure B.

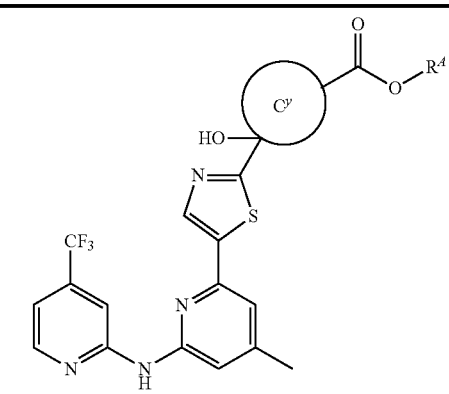

| Ex. No. | $R^A$ |
|---|---|
| 7.21 | 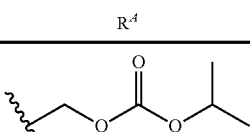 |
| 7.22 | 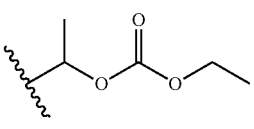 [SMILES: *C(C)OC(=O)OCC] |

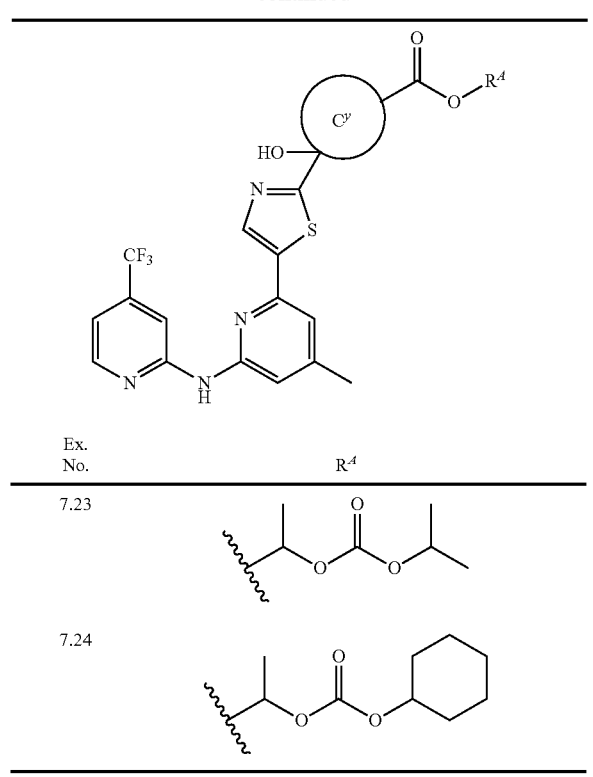

| Ex. No. | R^A |
|---|---|
| 7.23 | |
| 7.24 | |

Procedure C

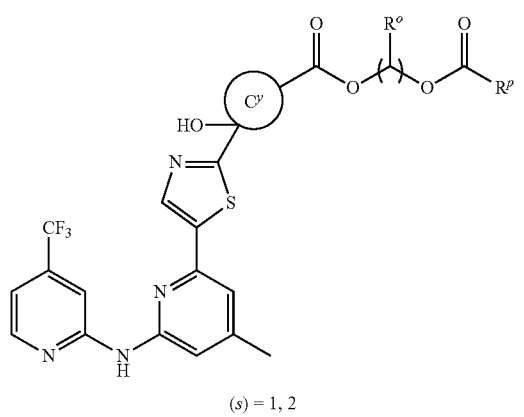

$(s) = 1, 2$

This general procedure describes the procedure for conversion of (A1) to (B) as shown in Scheme 7. To a solution of compound of formula (A1) (1.0 mmol) in DMF is added potassium carbonate (2.0 mmol) and sodium iodide (0.20 mmol). After 75 minutes, alkyl halide of formula (B1) (1.0 mmol) is added and the reaction mixture is stirred for an additional 4 hours. The reaction mixture is then partitioned between ethyl acetate and aqueous saturated sodium bicarbonate. The layers are separated, and then the organic layer is washed with water (3×) and brine, dried over sodium sulfate, filtered, and concentrated under reduced pressure. The resulting residue is purified by silica gel chromatography (ethyl acetate/hexanes, linear gradient) to afford the product residue. The residue is lyophilized from acetonitrile and water to afford a compound of formula (B).

The following compounds could be prepared according to procedures which were analogous to those described in Example 7, Procedure C.

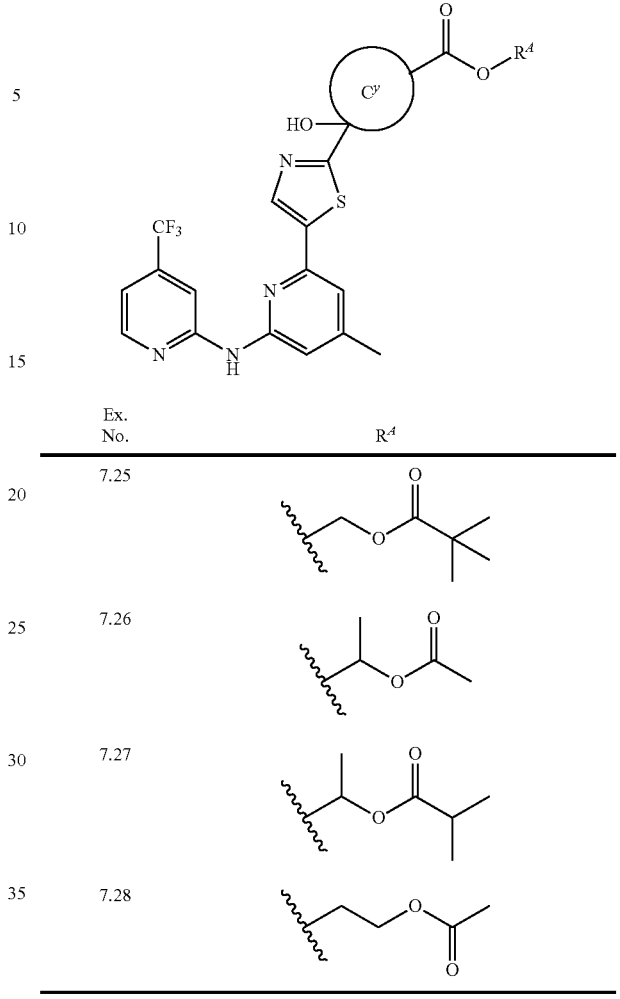

| Ex. No. | R^A |
|---|---|
| 7.25 | |
| 7.26 | |
| 7.27 | |
| 7.28 | |

Example 8

Compounds of Formula (I) Using the General Methods Illustrated in Scheme 8

The description provided in Example 8 is a prophetic example.

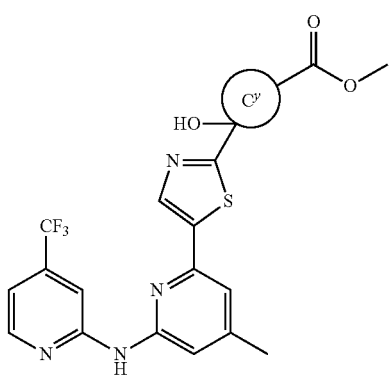

(D)

This general procedure describes the procedure for conversion of (A1) to (D) as shown in Scheme 8. To a suspension of compound of formula (A1) (1.0 mmol) in 1:1 methanol:dichloromethane is added trimethylsilyldiazomethane (2.0 M in diethyl ether, 1.0 mmol) at 0° C. The reaction mixture is stirred at 0° C. until all gas evolution ceases. The reaction mixture is allowed to warm to ambient temperature and quenched by the addition of several drops of acetic acid. The reaction mixture is concentrated under reduced pressure and the residue is purified by silica gel chromatography (ethyl acetate/hexanes, linear gradient) to afford the product residue. The residue is lyophilized from acetonitrile and water to afford a compound of formula (D).

Example 9

Preparation of Hydroxyalkyl Esters

The description provided in Example 9 is a prophetic example.

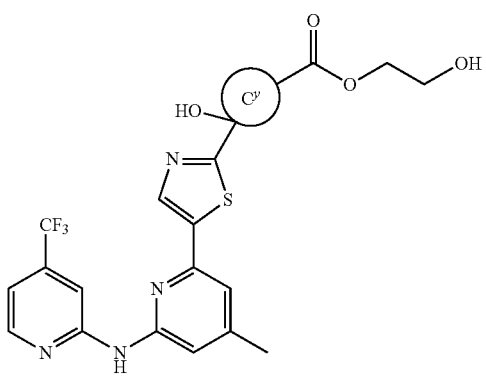

(E)

A mixture of compounds of formula (A1) (1.0 mmol), potassium carbonate (6.0 mmol) and sodium iodide (1.0 mmol) in DMF is stirred for 10 minutes at ambient temperature. To this mixture is added 2-chloroethanol (4.0 mmol) and the reaction mixture is heated at 60° C. for 16 hours. After 16 hours, additional 2-chloroethanol (1.0 mmol) is added and the reaction mixture is heated to 65° C. for an additional 2 hours. The reaction mixture is then diluted with ethyl acetate and washed sequentially with water (3×), aqueous sodium carbonate solution (2×), additional water (3×), and brine (2×). The organic layer is dried over magnesium sulfate, filtered, and concentrated under reduced pressure to afford the crude product residue. The residue is purified by silica gel chromatography ([3% (1.0 M ammonia in dioxane) in ethyl acetate]/[3% (1.0M ammonia in dioxane) in dichloromethane], linear gradient) to afford a compound of formula (E).

The suitability of the compounds of Formula (I) as prodrugs of Syk inhibitors can be tested as described below.

Hydrolysis Assay:
Analysis of Hydrolysis of Prodrug To Parent Species

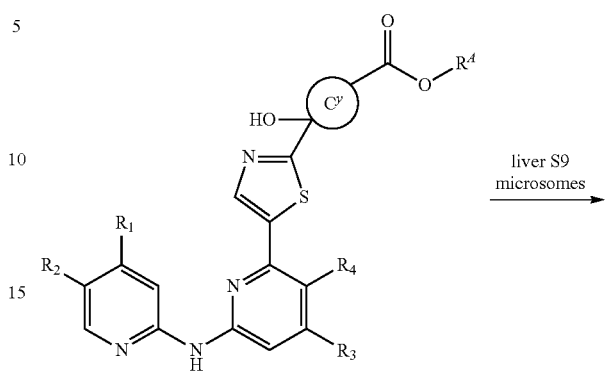

liver S9 microsomes

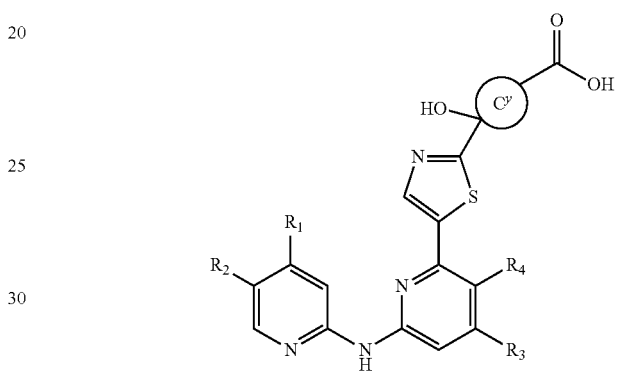

The stability of prodrugs is investigated in human liver S9 microsomes. Incubations of prodrugs (10 μM) with liver S9 (1 mg protein/mL) are carried out at 37° C. in a phosphate buffer, pH 7.4, containing 1 mM NADPH. Control incubations contain BSA (1.1 mg/mL) instead of liver S9 microsomes. Aliquots are removed at 0, 5, 15, 30, 60 and 120 min, treat with 4 volumes of acetonitrile containing 2% formic acid and an internal standard, and centrifuge. The supernatants are analyzed by LC-MS/MS for prodrug disappearance and appearance of active drug. The half-life of the prodrug is calculated from the % prodrug remaining at different time points calculated from on the peak area ratio relative to t=0. The amount of active drug generated at the different time points is determined using a standard curve.

Biological Assay
Homogeneous Time-Resolved Fluorescence (HTRF) Assay for the Recombinant Human Syk Enzyme A recombinant GST-hSYK fusion protein was used to measure potency of compounds to inhibit human Syk activity. The recombinant human GST-SYK (Carna Biosciences #08-176) (5 μM final concentration) was incubated with various concentrations of the inhibitor diluted in DMSO (0.1% final concentration) for 10 minutes at room temperature in 15 mM Tris-HCl (pH 7.5), 0.01% tween 20, 2 mM DTT in 384 well plate format. To initiate the reaction the biotinylated substrate peptide (250 nM final concentration) that contains the phosphorylation site for Syk was added with magnesium (5 mM final concentration) and ATP (25 M final concentration). Final volume of the reaction was 10 μL. Phosphorylation of the peptide was allowed to proceed for 45' at room temperature. To quench the reaction and detect the phosphorylated product, 2 nM of a Europium-antiphosphotyrosine antibody (Perkin Elmer #AD0161) and 70 nM SA-APC (Perkin-Elmer #CR130-100) were added together in 15 mM Tris pH 7.5, 40 mM EDTA, 0.01% tween 20. Final volume of the quenching solution was 10 L. The resulting HTRF signal was measured after 30 minutes on an EnVision (Perkin-Elmer) reader using a time-resolved fluorescence protocol. Table A below lists activities as $IC_{50}$ values (nM) for representative compounds of the invention.

TABLE A

| Ex. No. | $IC_{50}$ (nM) |
|---|---|
| 1.1 | 0.5808 |
| 1.2 | 0.1031 |
| 1.3 | 1.31 |
| 1.4 | 0.1635 |
| 1.5 | 0.5159 |
| 1.6 | 0.07093 |
| 1.7 | 6.285 |
| 1.8 | 0.1192 |
| 1.9 | 5.205 |
| 2.1 | 0.0718 |
| 2.2 | 1.189 |
| 2.3 | 23.85 |
| 2.4 | 0.8084 |
| 2.5 | 0.3158 |
| 2.6 | 1.474 |
| 2.7 | 1.007 |
| 2.8 | 339 |
| 2.9 | 2.179 |
| 2.10 | 1.836 |
| 2.11 | 0.9113 |
| 2.12 | 0.1516 |
| 2.13 | 0.3328 |
| 2.14 | 141.8 |
| 3.1 | 0.07295 |
| 3.2 | 1.716 |
| 3.3 | 0.5742 |
| 3.4 | 2.224 |
| 3.5 | 2.17 |
| 3.6 | 0.1577 |
| 3.7 | 0.092 |
| 3.8 | 0.7841 |
| 3.9 | 0.7331 |
| 3.10 | 5.398 |
| 3.11 | 0.2078 |
| 3.12 | 0.66 |
| 3.13 | 0.097 |
| 3.14 | 0.1037 |
| 3.15 | 0.127 |
| 3.16 | 1.31 |
| 3.17 | 0.1127 |
| 3.18 | 0.1604 |
| 4.1 | 0.5081 |
| 4.2 | 0.086 |
| 4.3 | 0.898 |
| 4.4 | 0.2282 |
| 4.5 | 0.8624 |
| 4.6 | 0.3919 |
| 4.7 | 71.16 |
| 4.8 | 1169 |
| 5.1 | 0.1607 |
| 5.2 | 0.5802 |
| 6.1 | 154.3 |

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:
1. A compound of the Formula (I)

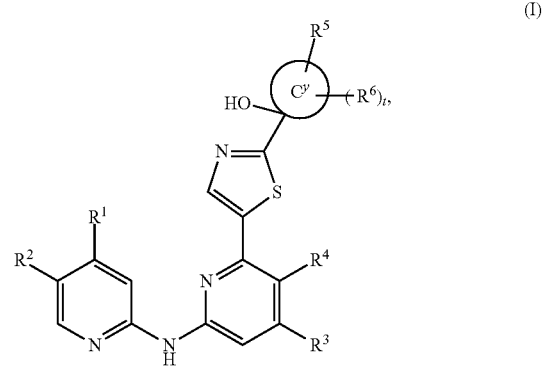

or a pharmaceutically acceptable salt thereof, wherein
$R^1$ is selected from the group consisting of:
(a) $C_1$-$C_6$ alkyl;
(b) $C_1$-$C_3$ alkoxy;
(c) $C_1$-$C_3$ fluoroalkyl;
(d) —$(CH_2)_rCO_2R^b$,
(e) —$O(CH_2)_sN(R^c)_2$,
(f) hydroxyl;
(g) halo;
(h) H;
(i) —C(O)—$C_1$-$C_6$ alkyl; and
(j) $C_3$-$C_6$ cycloalkyl;
$R^2$ is selected from the group consisting of H and halo;
$R^3$ is selected from the group consisting of
(a) H;
(b) $C_1$-$C_3$ alkyl;
(c) —$N(R^c)_2$;
(d) —N(H)C(O)—$C_1$-$C_4$ alkyl;
(e) —$CH_2$—O—$C_1$-$C_3$ alkyl;
$R^4$ is selected from the group consisting of H or halo;
$R^5$ is selected from the group consisting of
(a) —C(O)$OR^d$; and
(b) —C(O)$N(R^c)_2$;
each $R^6$ is a moiety independently selected from the group consisting of fluoro and $C_1$-$C_3$ alkyl;
ring $C^y$ is a saturated, mono- or bicyclic carbocyclic ring system consisting of 4 to 12 carbon atoms;
$R^b$ is H or $C_1$-$C_3$ alkyl;
each $R^c$ is independently H, $C_1$-$C_3$ alkyl, or —C(O)—O—$C_1$-$C_6$ alkyl;
$R^d$ is H or —C(O)—O—$C_1$-$C_6$ alkyl;
the subscript r is 0, 1, or 2;
the subscript s is 1, 2, 3, or 4;
the subscript t is 0, 1, 2, 3, 4, or 5;
$R^A$ is H or $C_1$-$C_3$ alkyl.
2. The compound of claim 1 or a pharmaceutically acceptable salt thereof, wherein $R^1$ is selected from the group consisting of —$CF_3$, —$CH_3$, —$C(CH_3)_3$, —$OCH_3$, —OC(H)$(CH_3)_2$, —$OCH_2CH_2CH_2NH_2$, —$OCH_2CH_2CH_2N(H)C(O)OC(CH_3)_3$, H, —$CO_2H$, —$CO_2CH_3$, —$CH_2CO_2H$, —$CH_2CO_2CH_3$, —OH, F, Cl, —O—C(O)$C(CH_3)_3$, and

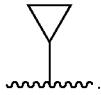

3. The compound of claim 1 or a pharmaceutically acceptable salt thereof, wherein $R^2$ is H, F, or Cl.

4. The compound of claim 1 or a pharmaceutically acceptable salt thereof, wherein $R^3$ is H, —CH$_3$, —CH$_2$OCH$_3$, —NH$_2$, or —N(H)—C(O)CH$_3$.

5. The compound of claim 1 or a pharmaceutically acceptable salt thereof, wherein $R^4$ is H.

6. The compound of claim 1 or a pharmaceutically acceptable salt thereof, wherein the moiety

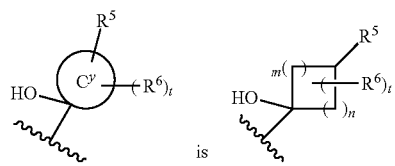

is and the subscripts m and n are independently 0, 1, 2, or 3, with the proviso that m and n are not both 0.

7. The compound of claim 1 or a pharmaceutically acceptable salt thereof, wherein the moiety

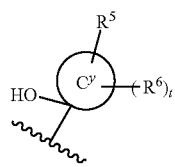

is selected from the group consisting of

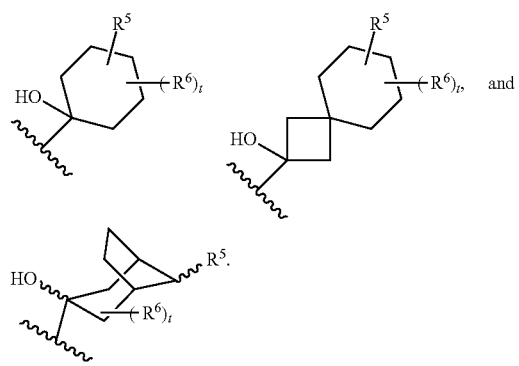

8. The compound of claim 1 or a pharmaceutically acceptable salt thereof, wherein the moiety

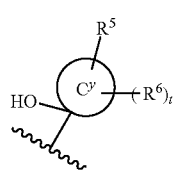

is selected from the group consisting of:

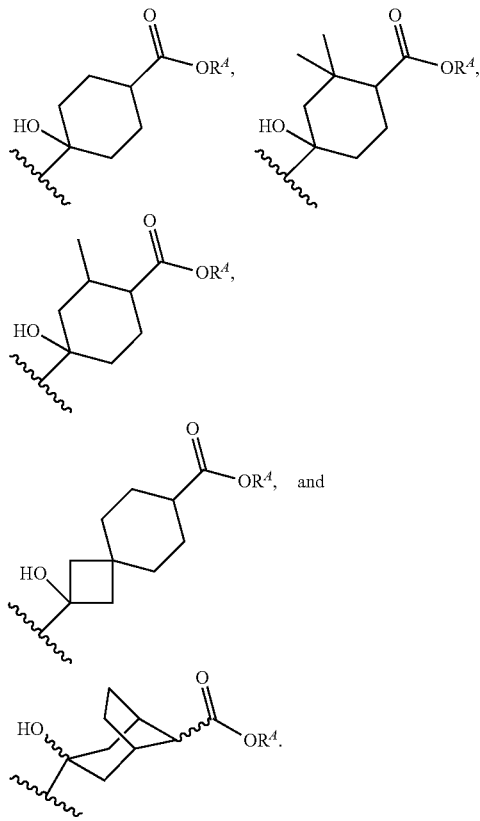

9. The compound of claim 1 or a pharmaceutically acceptable salt thereof, wherein the compound has the Formula (IA)

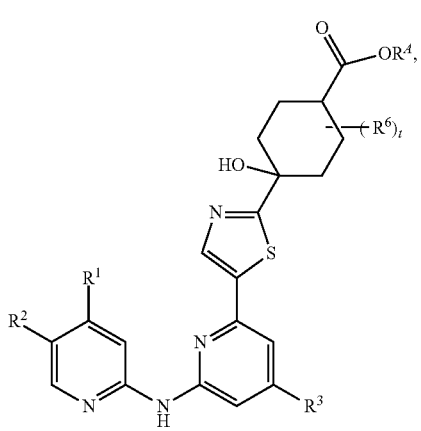

(IA)

wherein $R^1$ is —CH$_3$, —CF$_3$, or

;

$R^2$ is H or F;

$R^3$ is H or —CH$_3$;

$R^4$ is H or $C_1$-$C_3$ alkyl;
$R^6$ is —$CH_3$; and
the subscript t is 0, 1, or 2.

10. The compound of claim 1 or a pharmaceutically acceptable salt thereof, wherein $R^4$ is H.

11. The compound of claim 1 selected from the group consisting of:
- 4-(5-(6-(4-cyclopropylpyridin-2-yl)amino)-4-methylpyridin-2-yl)thiazol-2-yl)-4-hydroxy-2,2-dimethylcyclohexanecarboxylic acid;
- methyl 4-(5-{6-[(4-cyclopropylpyridin-2-yl)amino]-4-methylpyridin-2-yl}-1,3-thiazol-2-yl)-4-hydroxy-2,2-dimethylcyclohexanecarboxylate;
- 4-hydroxy-2,2-dimethyl-4-[5-(4-methyl-6-{[4-(trifluoromethyl)pyridin-2-yl]amino}pyridin-2-yl)-1,3-thiazol-2-yl]cyclohexanecarboxylic acid;
- 4-[5-(4-amino-6-{[4-(trifluoromethyl)pyridin-2-yl]amino}pyridin-2-yl)-1,3-thiazol-2-yl]-4-hydroxy-2,2-dimethylcyclohexanecarboxylic acid;
- methyl 4-{5-[4-(acetylamino)-6-{[4-(trifluoromethyl)pyridin-2-yl]amino}pyridin-2-yl]-1,3-thiazol-2-yl}-4-hydroxy-2,2-dimethylcyclohexanecarboxylate;
- methyl 4-[5-(4-amino-6-{[4-(trifluoromethyl)pyridin-2-yl]amino}pyridin-2-yl)-1,3-thiazol-2-yl]-4-hydroxy-2,2-dimethylcyclohexanecarboxylate;
- cis-4-(5-{6-[(4-{3-[(tert-butoxycarbonyl)amino]propoxy}pyridin-2-yl)amino]-4-methylpyridin-2-yl}-1,3-thiazol-2-yl)-4-hydroxycyclohexanecarboxylic acid;
- cis-4-[5-(6-{[4-(carboxymethyl)pyridin-2-yl]amino}-4-methylpyridin-2-yl)-1,3-thiazol-2-yl]-4-hydroxycyclohexanecarboxylic acid;
- 2-({6-[2-(cis-4-carboxy-1-hydroxycyclohexyl)-1,3-thiazol-5-yl]-4-methylpyridin-2-yl}amino)pyridine-4-carboxylic acid;
- ethyl cis-4-hydroxy-4-[5-(6-{[4-(2-methoxy-2-oxoethyl)pyridin-2-yl]amino}-4-methylpyridin-2-yl)-1,3-thiazol-2-yl]cyclohexanecarboxylate;
- methyl 2-[(6-{2-[cis-4-(ethoxycarbonyl)-1-hydroxycyclohexyl]-1,3-thiazol-5-yl}-4-methylpyridin-2-yl)amino]pyridine-4-carboxylate;
- cis-4-[5-(6-{[4-(3-aminopropoxy)pyridin-2-yl]amino}-4-methylpyridin-2-yl)-1,3-thiazol-2-yl]-4-hydroxycyclohexanecarboxylic acid;
- 4-hydroxy-2,2-dimethyl-4-[5-(4-methyl-6-{[4-(trifluoromethyl)pyridin-2-yl]amino}pyridin-2-yl)-1,3-thiazol-2-yl]cyclohexanecarboxylic acid;
- 4-(5-{6-[(4-tert-butylpyridin-2-yl)amino]pyridin-2-yl}-1,3-thiazol-2-yl)-4-hydroxy-2,2-dimethylcyclohexanecarboxylic acid;
- 4-hydroxy-2,2-dimethyl-4-[5-(6-{[4-(trifluoromethyl)pyridin-2-yl]amino}pyridin-2-yl)-1,3-thiazol-2-yl]cyclohexanecarboxylic acid;
- 4-(5-{6-[(5-fluoro-4-methylpyridin-2-yl)amino]pyridin-2-yl}-1,3-thiazol-2-yl)-4-hydroxy-2,2-dimethylcyclohexanecarboxylic acid;
- 4-(5-{6-[(4-chloropyridin-2-yl)amino]pyridin-2-yl}-1,3-thiazol-2-yl)-4-hydroxy-2,2-dimethylcyclohexanecarboxylic acid;
- 4-(5-{6-[(5-fluoropyridin-2-yl)amino]pyridin-2-yl}-1,3-thiazol-2-yl)-4-hydroxy-2,2-dimethylcyclohexanecarboxylic acid;
- 4-(5-{6-[(5-chloro-4-methylpyridin-2-yl)amino]pyridin-2-yl}-1,3-thiazol-2-yl)-4-hydroxy-2,2-dimethylcyclohexanecarboxylic acid;
- 4-hydroxy-2,2-dimethyl-4-(5-{6-[(4-methylpyridin-2-yl)amino]pyridin-2-yl}-1,3-thiazol-2-yl)cyclohexanecarboxylic acid;
- 4-(5-{6-[(5-chloro-4-methylpyridin-2-yl)amino]-4-methylpyridin-2-yl}-1,3-thiazol-2-yl)-4-hydroxy-2,2-dimethylcyclohexanecarboxylic acid;
- 4-hydroxy-4-(5-{6-[(4-methoxypyridin-2-yl)amino]-4-methylpyridin-2-yl}-1,3-thiazol-2-yl)-2,2-dimethylcyclohexanecarboxylic acid;
- 4-(5-{6-[(5-fluoro-4-methylpyridin-2-yl)amino]-4-methylpyridin-2-yl}-1,3-thiazol-2-yl)-4-hydroxy-2,2-dimethylcyclohexanecarboxylic acid;
- 4-(5-{6-[(4-tert-butylpyridin-2-yl)amino]-4-methylpyridin-2-yl}-1,3-thiazol-2-yl)-4-hydroxy-2,2-dimethylcyclohexanecarboxylic acid;
- 4-hydroxy-2,2-dimethyl-4-(5-{4-methyl-6-[(4-methylpyridin-2-yl)amino]pyridin-2-yl}-1,3-thiazol-2-yl)cyclohexanecarboxylic acid;
- cis-2-hydroxy-2-(5-(4-methyl-6-((4-(trifluoromethyl)pyridin-2-yl)amino)pyridin-2-yl)thiazol-2-yl)spiro[3.5]nonane-carboxylic acid;
- trans-2-hydroxy-2-[5-(4-methyl-6-{[4-(trifluoromethyl)pyridin-2-yl]amino}pyridin-2-yl)-1,3-thiazol-2-yl]spiro[3.5]nonane-7-carboxylic acid;
- trans-3-hydroxy-3-[5-(4-methyl-6-{[4-(trifluoromethyl)pyridin-2-yl]amino}pyridin-2-yl)-1,3-thiazol-2-yl]bicyclo[3.2.1]octane-8-carboxylic acid;
- cis-3-hydroxy-3-[5-(4-methyl-6-{[4-(trifluoromethyl)pyridin-2-yl]amino}pyridin-2-yl)-1,3-thiazol-2-yl]bicyclo[3.2.1]octane-8-carboxylic acid;
- cis-4-hydroxy-4-[5-(4-methyl-6-{[4-(1-methylethoxy)pyridin-2-yl]amino}pyridin-2-yl)-1,3-thiazol-2-yl]cyclohexanecarboxylic acid;
- cis-4-hydroxy-4-[5-(4-methyl-6-{[4-(trifluoromethyl)pyridin-2-yl]amino}pyridin-2-yl)-1,3-thiazol-2-yl]cyclohexanecarboxylic acid;
- 4-hydroxy-4-{5-[4-(methoxymethyl)-6-{[4-(trifluoromethyl)pyridin-2-yl]amino}pyridin-2-yl]-1,3-thiazol-2-yl}-2,2-dimethylcyclohexanecarboxylic acid;
- methyl 4-hydroxy-4-{5-[4-(methoxymethyl)-6-{[4-(trifluoromethyl)pyridin-2-yl]amino}pyridin-2-yl]-1,3-thiazol-2-yl}-2,2-dimethylcyclohexanecarboxylate;
- 4-(5-(6-((5-fluoro-4-methylpyridin-2-yl)amino)-4-methylpyridin-2-yl)thiazol-2-yl)-4-hydroxy-2-methylcyclohexanecarboxylic acid; and
- 4-hydroxy-4-(5-(6-((4-hydroxypyridin-2-yl)amino)-4-methylpyridin-2-yl)thiazol-2-yl)-2-methylcyclohexanecarboxylic acid;

or a pharmaceutically acceptable salt thereof.

12. A pharmaceutical composition comprising a therapeutically effective amount of the compound of claim 1 or a pharmaceutically acceptable salt thereof and a pharmaceutically acceptable carrier.

13. The compound of claim 9 or a pharmaceutically acceptable salt thereof, wherein $R^4$ is H.

14. The compound of claim 1 or a pharmaceutically acceptable salt thereof, wherein the compound is 4-(5-(6-((4-cyclopropylpyridin-2-yl)amino)-4-methylpyridin-2-yl)thiazol-2-yl)-4-hydroxy-2,2-dimethylcyclohexanecarboxylic acid.

* * * * *